United States Patent [19]

Ort et al.

[11] Patent Number: 5,186,736
[45] Date of Patent: Feb. 16, 1993

[54] HETEROCYCLIC N-ACYLSULFONAMIDES AND THEIR USE AS HERBICIDES OR GROWTH REGULATORS

[75] Inventors: Oswald Ort, Kelkheim; Lothar Willms, Hillscheid; Klaus Bauer, Hanau; Hermann Bieringer, Eppstein/Taunus; Arno Schulz, Hattersheim am Main, all of Fed. Rep. of Germany

[73] Assignee: Hoechst Aktiengesellschaft, Frankfurt am Main, Fed. Rep. of Germany

[21] Appl. No.: 728,632

[22] Filed: Jul. 11, 1991

Related U.S. Application Data

[62] Division of Ser. No. 387,531, Jul. 31, 1989, Pat. No. 5,053,072.

[30] Foreign Application Priority Data

Aug. 2, 1988 [DE] Fed. Rep. of Germany ....... 3826230

[51] Int. Cl.$^5$ ................ C07D 251/16; C07D 251/20; C07D 251/18; A01N 43/66
[52] U.S. Cl. .................................. 504/225; 544/113; 544/211; 544/212; 544/206; 544/207; 544/217; 544/218; 544/219; 544/216; 504/193; 504/219; 504/230; 504/227; 504/231; 504/233; 504/234
[58] Field of Search ................ 71/93; 544/113, 211, 544/212, 206, 207, 217, 218, 219, 216

[56] References Cited

FOREIGN PATENT DOCUMENTS 0244166 11/1987 European Pat. Off. .

OTHER PUBLICATIONS

Chemical Abstracts, 108:167298p, vol. 108, (1988) p. 632.
Chemical Abstracts, 108:131590p, vol. 108, (1988) p. 734.
Heinz Eilingsfeld, Manfred Patsch und Horst Scheuermann, "Synthese von Pyrimidinen aus Malondiimidsäureestern", Chem. Ber. 101, (1968) pp. 2426-2434.
Takao Sakamoto, Hiroshi Yoshizawa and Hiroshi Yamanaka, "Studies on Pyrimidine Derivatives. XXXVI.[1]) Reaction of 6-Substituted 2,4-Dimethylpyrimidines with Benzaldehyde in the Presence of Zinc Chloride", Chem. Pharm. Bull, vol. 32, (1984), pp. 2005-2010.
Takeji Sakasai, Takao Sakamoto and Hiroshi Yamanaka, "Studies on Pyrimidine Derivatives. XVII[1]). Synthesis of Pyrimidine-4-Carboxylic Esters", Heterocycles, vol. 13, (1979), pp. 235-238.
D. J. Brown and P. Waring, "Simple Pyrimidines. XV* The Synthesis, Piperidinolysis and Hydrolysis of Simple 2- and 4-(Halogenomethyl)pyrimidines", Aust. J. Chem., vol. 27, (1974), pp. 2251-2259.
Desmond J. Brown and Paul Waring, "Simple Pyrimidines. XVI* A Synthetic Route To Some 2-(-Pyrimidin-2'-yl)acetic Acids and Esters", Aust. J. Chem., vol. 30, (1977), pp. 621-627.
Hiroshi Yamanaka, Setsuko Niitsuma, Takao Sakamoto and Michinao Mizugaki, "1,3-Dipolar Cycloaddition of 4-Alkoxy-6-Methylpyrimidine N-Oxides", Heterocycles, vol. 5, (1976), pp. 255-260.
Hiroshi Yamanaka, Setsuko Niitsuma, Takao Sakamoto and Michinao Mizugaki, "Studies on Pyrimidine Derivatives. XII.[1]) Reaction of 4,6-Disubstituted Pyrimidine N-Oxides with Dimethyl Acetylenedicarboxylate", Chem. Pharm. Bull. vol. 27, No. 10 (1979), pp. 2291-2294.
Desmond J. Brown and Paul Waring, "Simple Pyrimidines. XVII* The Effect of 4'(6')-Substituents on the Ionization of 2-(Pyrimidin-2'-yl)Acetic Acid", Aust. J. Chem., vol. 31, (1978), pp. 649-659.
Hiroshi Yamanaka, Masayuki An-Naka, Yoshinori Kondo and Takao Sakamoto, "Studies on Pyrimidine Derivatives. XXXVIII.[1]) Cross-Coupling Reaction of N-Heteroaryl Iodides with Ethoxycarbonylmethylzinc Bromide in the Presence of Palladium Catalyst", Chem. Pharm. Bull, vol. 33, (1985), pp. 4309-4313.
Hiroshi Yamanaka, Shoetsu Konno, Takao Sakamoto, Setsuko Niitsuma and Sayo Noji, "Studies on Pyrimidine Derivatives. XXIII.[1]) Synthesis of Acylmethylpyrimidines and Related Compounds via Imidoyl-Substituted Oxosulfonium Ylides", Chem. Pharm. Bull, vol. 29, (1981), pp. 2837-2843.
Takao Sakamoto, Ken-Ichi Tanji, Setsuko Niitsuma, Takayasu Ono and Hiroshi Yamanaka, "Studies on (List continued on next page.)

*Primary Examiner*—John M. Ford
*Attorney, Agent, or Firm*—Curtis, Morris & Safford

[57] ABSTRACT

Compounds of the formula I or salts thereof

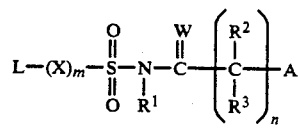

where $R^1$ is H or an aliphatic radical; $R^2$ and $R^3$ are H, alkyl or phenyl; W is O, S, $NR^4$ or $NOR^4$; X is $CHR^2$, O or $NR^4$; L is a (substituted) phenyl, naphthyl or monocyclic heteroaryl radical, A is a (substituted) pyrimidyl, triazinyl, triazolyl or bicyclic heteroaryl radical, and m and n are 0 or 1, have advantageously herbicidal or plant growth-regulating properties.

13 Claims, No Drawings

OTHER PUBLICATIONS

Pyrimidine Derivatives. XX.[1] Synthetic Utility of Hydroxymethylpyrimidines and Related Compounds", Chem. Pharm. Bull, vol. 28, (1980), pp. 3362–3368.

Setsuko Niitsuma, Takao Sakamoto and Hiroshi Yamanaka, "Synthesis of 2-Acylmethylpyrimidines for 2-Chloro-4,6-Dimethylpyrimidine", Heterocycles, vol. 10, (1978), pp. 171–176.

A. N. Kost, R. S. Sagitullin and G. G. Danagulyan, "Action of Nucleophilic Agents on the Pyrimidine Ring", Khimiya Geterotsiklicheskikh Soedinenni, No. 10, (1978) pp. 1400–1405 (translation thereof).

G. M. Vakhatova and L. N. Yakhontov, "s-Triazine Derivatives. 3.* Investigation of the Reaction of Chloromethoxy-s-Triazines with CH Acids", Khimiya Geterotsiklicheskikh Sodeinenni, No. 2, (1981) pp. 264–267 (translation thereof).

E. L. Zaitseva, A. Ya. Yakubovich, G. I. Braz and V. P. Bazov, "Syntheses in the s-Triazine Series. III. (Benzoyloxyalkyl)-s-Triazines", Zhurnal Obshchei Khimii, vol. 34, No. 9, Sep. 1964, pp. 2976–2979 (translation thereof).

Fred C. Schaefer, "Synthesis of the s-Triazine System. VI.[1] Preparation of Unsymmetrically Substituted s--Triazines by Reaction of Amidine Salts with Imidates", J. Org. Chem., vol. 27, Oct. 1962, pp. 3608–3613.

Ehrenfried Kober, "The Reaction of Ketene Diethyl Acetal with Cyanuric Chloride", J. Org. Chem., vol. 26, (1961), pp. 4705–4706.

Hans Meerwein, Gerhard Dittmar, Rudolf Göllner, Klaus Hafner, Fritz Mensch and Otto Steinfort, "Verfahren zur Herstellung Aromatischer Sulfonsäurechloride, Eine Neue Modifikation der Sandmeyerschen Reaktion", Chemische Berichte, vol. 90, No. 6, (1957), pp. 841–852.

HETEROCYCLIC N-ACYLSULFONAMIDES AND THEIR USE AS HERBICIDES OR GROWTH REGULATORS

This application is a division of application Ser. No. 07/387,531, filed Jul. 31, 1989, now U.S. Pat. No. 5,053,072.

DESCRIPTION

It is already known that certain sulfonylated bi- or tricyclic heteroaromatic carboxamides have herbicidal and growth-regulating properties (EP-A-244,166). Sulfonylated monocyclic pyridinecarboxamides are described as fungicides and microbiocides in agriculture (Chem. Abstr. 108 (19): 167298p; Chem. Abstr. 108 (15): 131590p). A herbicidal action of these compounds has not been disclosed.

It has been found that heterocyclic N-acylsulfonamides have advantageous herbicidal and growth-regulating properties.

The present invention therefore relates to compounds of the formula I or their salts

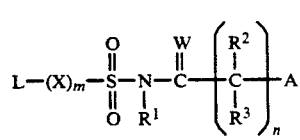

I where

R$^1$ is hydrogen, (C$_1$–C$_4$)-alkyl, (C$_2$–C$_6$)-alkenyl or (C$_2$–C$_6$)-alkynyl;

R$^2$ and R$^3$ independently of one another are hydrogen, (C$_1$–C$_3$)-alkyl or phenyl;

W is O, S, NR$^4$ or NOR$^4$,

R$^4$ is hydrogen, (C$_1$–C$_3$)-alkyl, (C$_1$–C$_3$)-haloalkyl or phenyl;

X is CHR$^2$, O, NR$^4$ or NOR$^4$,

L is a heterocyclic or isocyclic radical of the formulae (L1)–(L5),

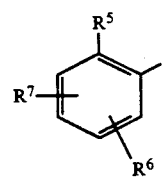

(L1)

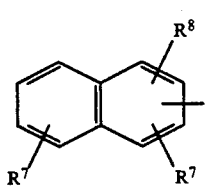

(L2)

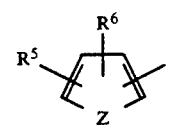

(L3)

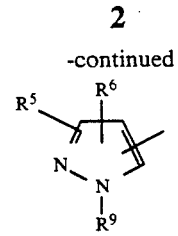

(L4)

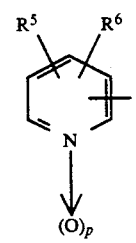

(L5)

A is a heterocyclic radical of the formulae (A1)–(A8)

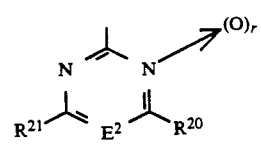

(A1)

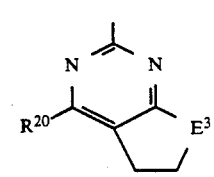

(A2)

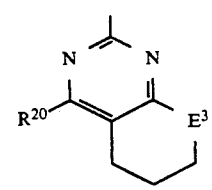

(A3)

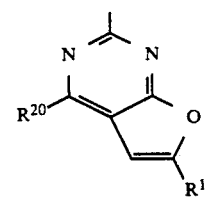

(A4)

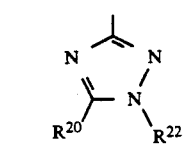

(A5)

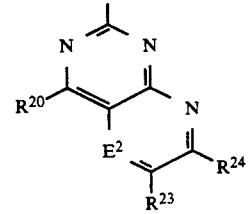

(A6)

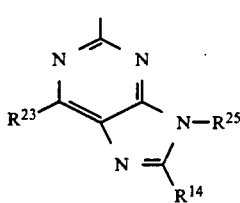

(A7)

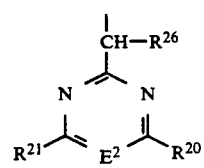

(A8)

Z is O or S(O)$_q$,
E$^1$ is O or S(O)$_b$,
E$^2$ is CH or N,
E$^3$ is O or CH$_2$,
a, m, n, p, r and s independently of one another are 0 or 1,
b and q independently of one another are 0, 1 or 2,
R$^5$ is hydrogen, halogen, NO$_2$, CN, (C$_1$–C$_4$)-alkyl which is unsubstituted or monosubstituted or polysubstituted by F, Cl or Br or monosubstituted by CN, OCH$_3$ or SCH$_3$, or is (C$_2$–C$_4$)-alkenyl which is unsubstituted or monosubstituted or polysubstituted by F, Cl or Br or monosubstituted by OCH$_3$; or is (C$_2$–C$_4$)-alkynyl which is unsubstituted or monosubstituted or polysubstituted by F, Cl or Br or monosubstituted by OCH$_3$ or Si(CH$_3$)$_3$; or is (C$_3$–C$_6$)-cycloalkyl which is unsubstituted or monosubstituted or polysubstituted by F, Cl or CH$_3$; or is —C(O)R$^{10}$, —OCH$_2$CH$_2$OR$^{10}$, —OH, —C(R$^{10}$)(OR$^{11}$)(OR$^{12}$); —CO$_2$R$^{13}$, —C(O)NR$^{14}$R$^{15}$, —N$_3$, —SO$_2$NR$^{14}$R$^{15}$, —SO$_3$R$^{16}$, —OSO$_2$R$^{17}$, phenyl which is unsubstituted or monosubstituted or polysubstituted by F, Cl, Br, CH$_3$ or OCH$_3$; or is —E$^1$R$^{18}$ or —(CH$_2$)$_s$G, R$^6$ is hydrogen or halogen; CN; NO$_2$; (C$_1$–C$_4$)-alkyl which is unsubstituted or monosubstituted or polysubstituted by halogen or monosubstituted to disubstituted by —CO$_2$R$^{13}$, —SO$_2$NR$^{14}$R$^{15}$, —NR$^{14}$R$^{15}$, (C$_1$–C$_2$)-alkoxy, —E$^1$R$^{19}$, (C$_1$–C$_2$)-haloalkoxy, (C$_1$–C$_2$)-alkylthio, (C$_1$–C$_2$)-haloalkylthio, CN, OH or SH; or is —CO$_2$R$^{13}$, —SO$_2$NR$^{14}$R$^{15}$, —NR$^{14}$R$^{15}$ or —E$^1$R$^{19}$;

R$^7$ radicals independently of one another are hydrogen, (C$_1$–C$_4$)-alkyl, (C$_1$–C$_4$)-haloalkyl, (C$_2$–C$_4$)-alkenyl, phenyl or phenyl which is monosubstituted or polysubstituted by halogen or —E$^1$R$^{19}$; or is —E$^1$R$^{19}$ or halogen, R$^8$ is hydrogen, (C$_1$–C$_4$)-alkyl, (C$_1$–C$_4$)-haloalkyl, halogen, —CO$_2$R$^{13}$, —SO$_2$NR$^{14}$R$^{15}$, —OSO$_2$R$^{17}$, —S(O)$_b$R$^{18}$, CN or NO$_2$, R$^9$ is hydrogen, (C$_1$–C$_4$)-alkyl which is unsubstituted or monosubstituted or polysubstituted by halogen or monosubstituted by phenyl; or is (C$_2$–C$_4$)-alkenyl; or is phenyl or phenyl which is monosubstituted or polysubstituted by halogen, (C$_1$–C$_4$)-alkyl, NO$_2$, CN or (C$_1$–C$_4$)-alkoxy, R$^{10}$ is hydrogen, (C$_1$–C$_4$)-alkyl, (C$_1$–C$_4$)-alkyl which is monosubstituted or polysubstituted by F, Cl, Br or OCH$_3$; or is (C$_3$–C$_6$)-cycloalkyl which is unsubstituted or monosubstituted or polysubstituted by F, Cl, Br or CH$_3$; or is (C$_2$–C$_4$)-alkenyl or (C$_2$–C$_4$)-alkynyl;

R$^{11}$ and R$^{12}$ independently of one another are (C$_1$–C$_4$)-alkyl, or R$^{11}$ and R$^{12}$ together are —CH$_2$CH$_2$—, —CH$_2$OCH$_2$— or —CH$_2$C(CH$_3$)$_2$CH$_2$—;

R$^{13}$ is hydrogen, (C$_1$–C$_4$)-alkyl which is unsubstituted or monosubstituted or polysubstituted by halogen or monosubstituted to disubstituted by CN, CO$_2$R$^{10}$, NR$^{14}$R$^{15}$, OR$^{10}$ or Si(CH$_3$)$_3$; or is (C$_3$–C$_4$)-alkynyl which is unsubstituted or substituted by CH$_3$ or Si(CH$_3$)$_3$; or is (C$_3$–C$_6$)-cycloalkyl, (C$_3$–C$_6$)cycloalkyl-(C$_1$–C$_4$)alkyl, (C$_1$–C$_4$)-alkoxy or Si(CH$_3$)$_3$, R$^{14}$ is hydrogen or (C$_1$–C$_4$)-alkyl, or R$^{14}$ and R$^{15}$ together are —(CH$_2$)$_2$(CH$_2$)$_a$(CH$_2$)$_2$— or —(CH$_2$)$_2$O(CH$_2$)$_2$—, R$^{15}$ is hydrogen, (C$_1$–C$_4$)-alkyl, (C$_1$–C$_4$)-alkoxy, (C$_2$–C$_4$)-alkenyl, or R$^{14}$ and R$^{15}$ together are —(CH$_2$)$_2$(CH$_2$)$_a$(CH$_2$)$_2$— or —(CH$_2$)$_2$O(CH$_2$)$_2$—, R$^{16}$ is (C$_1$–C$_4$)-alkyl or (C$_1$–C$_4$)-haloalkyl, R$^{17}$ is (C$_1$–C$_4$)-alkyl or NR$^{14}$R$^{15}$, R$^{18}$ is (C$_1$–C$_4$)-alkyl, (C$_1$–C$_4$)-haloalkyl, (C$_2$–C$_4$)-alkoxyalkyl, (C$_2$–C$_4$)alkenyl, (C$_3$–C$_4$)-alkynyl, phenyl or phenyl which is monosubstituted or polysubstituted by halogen, (C$_1$–C$_3$)-alkyl, (C$_1$–C$_3$)-alkoxy or (C$_1$–C$_3$)-haloalkyl;

R$^{19}$ is (C$_1$–C$_4$)-alkyl or (C$_1$–C$_4$)-alkyl which is monosubstituted or polysubstituted by F or Cl or monosubstituted by OR$^{16}$, R$^{20}$ and R$^{21}$ independently of one another are hydrogen, halogen, (C$_1$–C$_6$)-alkyl, (C$_1$–C$_6$)-alkoxy or (C$_1$–C$_6$)-alkylthio, it being possible for the three abovementioned radicals to be monosubstituted or polysubstituted by halogen or monosubstituted or disubstituted by (C$_1$–C$_4$)-alkoxy or (C$_1$–C$_4$)-alkylthio; or are —NR$^{14}$R$^{15}$, (C$_3$–C$_6$)-cycloalkyl, —OCHR$^{14}$—CO$_2$R$^{13}$, (C$_2$–C$_5$)-alkenyl, (C$_2$–C$_4$)-alkynyl, (C$_3$–C$_5$)-alkenyloxy or (C$_3$–C$_5$)-alkynyloxy;

R$^{22}$ is (C$_1$–C$_4$)alkyl or (C$_1$–C$_4$)-haloalkyl,

R$^{23}$ and R$^{24}$ independently of one another are hydrogen, (C$_1$–C$_4$)-alkyl, (C$_2$–C$_4$)-alkenyl or (C$_2$–C$_4$)-alkynyl;

R$^{25}$ is hydrogen, (C$_1$–C$_4$)-alkyl or (C$_1$–C$_4$)-haloalkyl;

R$^{26}$ is hydrogen or (C$_1$–C$_3$)-alkyl,

G is a heterocyclic radical (G 1)–(G 25),

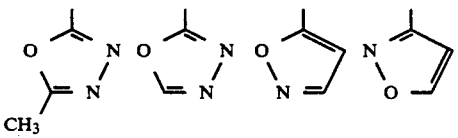

(G1)　　(G2)　　(G3)　　(G4)

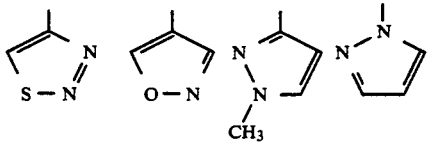

(G5)　　(G6)　　(G7)　　(G8)

-continued

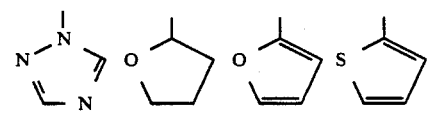

(G9)   (G10)   (G11)   (G12)

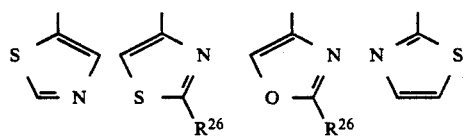

(G13)   (G14)   (G15)   (G16)

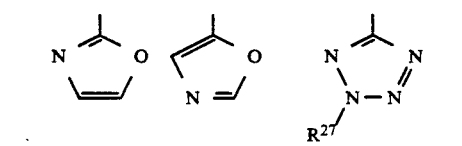

(G17)   (G18)   (G19)

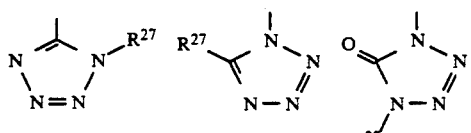

(G20)   (G21)   (G22)

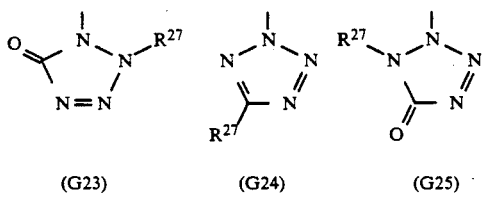

(G23)   (G24)   (G25)

$R^{27}$ is hydrogen, $(C_1-C_3)$-alkyl or $(C_2-C_4)$-alkenyl.

The compounds of the formula I can contain one or more chiral centers and are then present as mixtures of diastereomers or enantiomers. The invention embraces the pure enantiomers or diastereomers and their mixtures.

In the event that $R^1$ is H, the compounds of the formula I can form salts in which the hydrogen of the $-SO_2-NH-$ group is replaced by a cation which is suitable for agriculture. In general, these salts are metal salts, in particular alkali metal salts, alkaline earth metal salts, optionally alkylated ammonium salts or organic amine salts. They are preferably prepared in inert solvents, such as, for example, water, methanol or acetone, at temperatures from 0°-100° C. Examples of suitable bases for the preparation of salts according to the invention are alkali metal carbonates, such as potassium carbonate, or alkali metal hydroxides and alkaline earth metal hydroxides, ammonia or ethanolamine.

In the abovementioned definitions, the term "alkyl", on its own or in compound words, such as "alkylthio", "haloalkyl", "alkylamino" or "bisalkylamino", in each case denotes straight-chain or branched alkyl.

Likewise alkenyl denotes straight-chain or branched-chain alkenyl, for example 1-propenyl, 2-propenyl or 3-propenyl. Alkynyl denotes straight-chain or branched-chain alkynyl, for example ethynyl, 1-propynyl, 2-propynyl or the various butynyl isomers. Alkylsulfonyl denotes, for example, methylsulfonyl, ethylsulfonyl or the various propylsulfonyl isomers.

The term "halogen" on its own or in compound words such as "haloalkyl" denotes fluorine, chlorine, bromine or iodine. Furthermore, the meaning of compound words such as "haloalkyl" is that said alkyl is partly or completely halogenated. Examples of haloalkyl are $CHF_2$, $CH_2CH_2F$, $CF_2CF_3$ and $CH_2CHFCl$.

Preferred compounds of the general formula I are those where

A is a radical of the formulae (A1), (A2), (A3) or (A4), in particular (A1);

L is a radical of the formulae (L1), (L3), (L4) or (L5),

X is $CH_2$, $CH(CH_3)$, O, NH, $NCH_3$, $NC_2H_5$ or $NOCH_3$, in particular $CH_2$, O or NH, W is oxygen, $R^1$ is hydrogen, $R^2$ and $R^3$ independently of one another are hydrogen or $(C_1-C_3)$-alkyl, in particular hydrogen, $R^5$ is halogen, $NO_2$, CN, $(C_1-C_3)$-alkyl which is unsubstituted or substituted by F, Cl, Br, CN, $OCH_3$ or $SCH_3$; or is $(C_3)$-alkenyl which is unsubstituted or substituted by F, Cl or Br; or is $(C_3)$-alkynyl, $(C_3)$-cycloalkyl, which is unsubstituted or substituted by F, Cl or $CH_3$, or is $-C(O)R^{10}$, $-OCH_2CH_2OR^{10}$, OH, $-C(R^{10})(OR^{11})$ $(OR^{12})$, $-CO_2R^{13}$, $-C(O)NR^{14}R^{15}$, $N_3$, $-SO_2NR^{14}R^{15}$, $-OSO_2R^{17}$, $-R^1R^{18}$ or $-(CH_2)_sG$;

$R^6$ is hydrogen, halogen, CN, $NO_2$, $CH_3$, $CF_3$, $-E^1R^{19}$ or $(C_1-C_2)$-alkoxy-$(C_1-C_2)$-alkyl, $(C_1-C_2)$-haloalkoxy, $(C_1-C_2)$-alkylthio, $(C_1-C_2)$-haloalkylthio, CN, $-CO_2R^{13}$ or $-SO_2NR^{14}R^{15}$, $R^7$ is hydrogen, $R^{10}$ is $(C_1-C_3)$-alkyl, cyclopropyl or $(C_3)$-alkenyl, $R^{11}$ and $R^{12}$ are $(C_1-C_2)$-alkyl, or $R^{11}$ and $R^{12}$ together are $-CH_2CH_2-$, $R^{13}$ is $(C_1-C_3)$-alkyl, $(C_3)$-alkenyl, $-CH_2CH_2F$, $-CH_2CH_2Cl$, $-CH_2CH_2OCH_3$ or cyclopropylmethyl;

$R^{14}$ is hydrogen or $CH_3$, or $R^{14}$ and $R^{15}$ together are $-(CH_2)_4-$, $-(CH_2)_5-$ or $-(CH_2)_2O(CH_2)_2-$, $R^{15}$ is $CH_3$, $CH_2CH_3$ or $OCH_3$, or $R^{14}$ and $R^{15}$ together are $-(CH_2)_4-$, $-(CH_2)_5-$ or $-(CH_2)_2O(CH_2)_2-$, $R^{18}$ is $(C_1-C_3)$-alkyl, $(C_1-C_3)$-haloalkyl, $(C_2-C_3)$-alkyloxyalkyl, allyl, propargyl or $(C_2-C_3)$-haloalkenyl, $R^{19}$ is $(C_1-C_2)$-alkyl which is unsubstituted or substituted by F, Cl or $OCH_3$, $R^{20}$ and $R^{21}$ independently of one another are hydrogen, $(C_1-C_2)$-alkyl, $(C_1-C_2)$-alkoxy, $-CH_2OCH_3$, Cl, F, Br, I, $-CH_2OCH_2CH_3$, $-NHCH_3$, $-N(OCH_3)CH_3$, $-N(CH_3)_2$, $-CF_3$, $-SCH_3$, $-CH(OCH_3)_2$, $-OCH)CH=CH_2$; $-OCH_2C\equiv CH$, $-OCH_2CH_2OCH_3$, $-CH_2SCH_3$, $-OCHF_2$, $-SCHF_2$, cyclopropyl, $-C\equiv CH$ or $-C\equiv C-CH_3$, m is 0 or 1, n is 0 or 1, s is zero and $E^1$ is O or S.

Radicals which are particularly preferred for $R^{20}$ are $CH_3$, $OCH_3$, $CH_2CH_3$, $OCH_2CH_3$, $OCHF_2$, $OCH_2OCH_3$, $CH_2OCH_3$, $NHCH_3$, $CH(OCH_3)_2$, Cl or cyclopropyl and radicals which are particularly preferred for $R^{21}$ are $CH_3$, $OCH_3$, $OCH_2CH_3$ or $OCHF_2$.

The present invention also relates to processes for the preparation of the compounds of the formula I, which comprise, a) for the preparation of compounds with W=O, $a_1$) reacting a compound of the formula II with

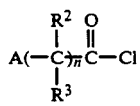

(II)

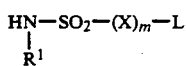

(III)

a compound of the formula III in the presence of a base, or $a_2$) reacting a compound of the formula (IIa)

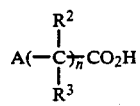

(IIa)

with a compound of the formula III in the presence of activating reagents, such as 2-chloro-1-methylpyridinium chloride (IVa), dicyclohexylcarbodiimide (IVb) or 1,1-carbonyldiimidazole (IVc) and if appropriate in the presence of a base, or $a_3$) for the preparation of compounds with W=O, and $R^1$=H, reacting a compound of the formula (V),

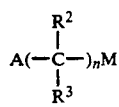

(V)

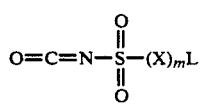

(VI)

where M is hydrogen or lithium, with a compound of the formula (VI), or b) for the preparation of compounds with W=S, reacting a compound of the formula I obtained in a) with the compound of the formula VII,

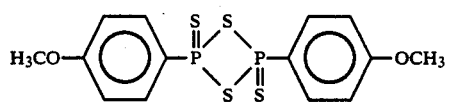

(VII)

c) for the preparation of compounds with $W=NR^4$, reacting a compound of the formula VIII

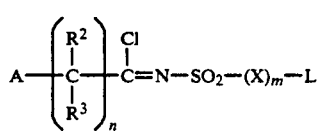

(VIII)

with an amine of the formula $H_2N-R^4$, d) for the preparation of the compounds with $W=NOR^4$, $d_1$) reacting a compound of the formula IX with

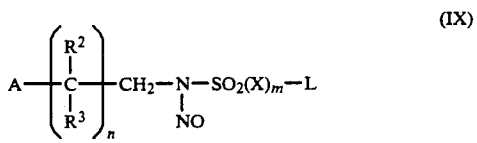

(IX)

an alkali metal hydroxide or alkaline earth metal hydroxide or ammonium hydroxide, or $d_2$) reacting a compound of the formula VIII with a hydroxylamine of the formula $H_2N-OR^4$ in the presence of a base, or e) for the preparation of compounds of the formula I with $R^1 \neq H$, reacting a compound of the formula I with $R^1=H$ with an alkyl halide of the formula $R^{1'}-x^1$ in the presence of a base, where $R^{1'}$ has the meaning indicated for $R^1$ with the exception of hydrogen and $X^1$ is chlorine, bromine or iodine, and, if appropriate, converting the compounds obtained, of the formula I, into its salt.

The acid chloride of the formula II which is employed in process $a_1$) may be prepared in a known manner from the corresponding carboxylic acid of the formula (IIa)

(IIa)

or its salt with inorganic acid chlorides, such as thionyl chloride or with oxalyl chloride in the presence of suitable bases, in particular organic nitrogen bases, such as pyridine, 2,6-lutidine or triethylamine and/or catalysts, such as N,N-4-dimethylaminopyridine or dimethylformamide, and is advantageously reacted directly with the component III in the presence of the mentioned base, without intermediate isolation. Excess thionyl chloride or oxalkyl chloride is distilled off before the acid chloride II is reacted with the sulfonamide III.

The reactions in accordance with process variant $a_2$) are known per se. Preferably, they are carried out in an inert, aprotic solvent, such as dichloromethane, 1,2-dichloroethane, acetonitrile or glycol dimethyl ether, at temperatures between −30° C. to 83° C.

Examples of bases which are used are organic nitrogen bases, such as pyridine, triethylamine etc. In the case of carbonyldiimidazole, it is not necessary to add bases.

Process $a_3$) is known per se; preferably, it is carried out in an inert, aprotic solvent, such as dichloromethane, tetrahydrofuran, 1,2-dichloroethane or glycol dimethyl ether, in the temperature range of −78° C. to 85° C.

The process in accordance with variant b) is likewise known per se; preferably, it is carried out in an inert aprotic solvent, such as toluene or xylene, at temperatures between 0° C. and 145° C. In those cases in which the products are insoluble in the reaction medium, they can be isolated by a simple filtration. If the reaction products are soluble, they can be obtained after the solvent has been evaporated, by crystallization or chromatography of the residue.

Process variants c) and d) are known in principle. Process c) and $d_2$) are preferably carried out in an inert aprotic solvent, such as dichloroethane or toluene, in the temperature range between 0° C. and 110° C.

The imidoyl chlorides of the formula VIII can be obtained by reacting a compound of the formula I, prepared in accordance with variant a), with triphenylphosphine/tetrachloromethane or $PCl_5/POCl_3$. The process is preferably carried out in $CCl_4$ or $POCl_3$ at temperatures between 0° C. and 105° C., cf. Houben-Weyl, Vol. E5/1, pp. 628-632 (1985); Vol. 5/3 pp. 916-922 and Vol. 8 pp. 346, 673-76.

Process e), which is known per se, is preferably carried out in an inert, aprotic solvent, such as dichloromethane, tetrahydrofuran, 1,2-dichloroethane or glycol dimethyl ether, in the temperature interval from −78° C. to 85° C.

The carboxylic acids of the formula (IIa), which correspond to the acid chloride of the formula (II), can be prepared using a range of methods. Methods which are possible are, for example, alkaline hydrolysis of the corresponding carboxylic esters (J. March "Advanced Organic Chemistry", 3rd edition, John Wiley & Sons, NY 1985, pp. 334-338), or the reaction of the ester compounds with lithium iodide in pyridine or other amines, or with trimethylsilyl chloride and sodium iodide (cf. J. March, "Advanced Organic Chemistry" 3rd edition, John Wiley & Sons, NY 1985, page 386) or by reaction with iodotrimethylsilane, see Olah, Narany, Tetrahedron 38 2225-2277 (1982), or by reaction with hydrobromic acid.

Furthermore, the carboxylic acids (IIa) can be prepared from the corresponding nitriles by hydrolysis, see Monatsh. Chem. 87, 625-35 (1956) or conversion into the imidoethers and subsequent hydrolysis, see T. Sakamoto; Chem. Pharm. Bull. 28, 3362-8 (1980).

Furthermore, the carboxylic acids (IIa) can be prepared from the corresponding benzyl esters by hydrogenation in the presence of a catalyst, such as palladium, see Houben-Weyl, "Methoden der organischem Chemie" (Methods of Organic Chemistry), Vol. 4/1c (1980), pp. 379-387.

As an alternative, it is possible to obtain the carboxylic acids of the formula IIa directly by reacting the halogenated heterocycles of the formula IIb

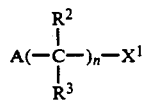
(IIb)

with carbon dioxide, or indirectly via organometal intermediates, see Volpin and Kolomnikov, Organomet. React. 5, 313-386 (1985); Sneeden, in Patai "The Chemistry of Carboxylic Acids and Esters", pp. 137-173, Interscience, NY 1969; and also Kharasch and Reinmuth, Grignard Reactions of Nonmetallic Substances", pp. 913-948, Prentice-Hall, Englewood Cliffs, N.Y. 1954.

The nitriles on which the carboxylic acids IIa are based can be obtained from the compounds of the formula (IIc)

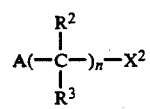
(IIc)

by reaction with alkali metal cyanides or tetraalkylammonium cyanides. $X^2$ in formula (IIc) is a leaving group, such as chlorine, bromine, iodine, p-tosyl, $OSO_2CH_3$ or tetraalkylammonium, see W. Klötzer, Monatsh. Chem. 87, 526-35 (1956); H. Kobler, Liebigs Ann. Chem. 1978, 1937-45, T. Sakamoto, Chem. Pharm. Bull. 28, 3362-8 (1980); J. March, "Advanced Organic Chemistry", 3rd edition, John Wiley & Sons, NY 1985, pp. 594-595; Houben-Weyl, Vol. E5/2, pp. 1447-1474 (1985).

As an alternative, the nitrile compounds can be obtained by reacting heterocyclic N oxides of the formula A→O with trimethylsilyl cyanide, see H. Yamanaka, Synthesis 1984, 681-3; and H. Vorbrüggen, Synthesis 1983, 316-9; Houben-Weyl, Vol. E5/2, pp. 1444-1446 (1985).

Furthermore, the nitriles can be prepared from the amines of the formula $A-NH_2$ by a Sandmeyer reaction, i.e. by diazotization and subsequent reaction with copper(II) cyanide.

The halogenated heterocycles of the formula (IIb) may be prepared by halogenating the corresponding alkylated heterocyclic N oxides, see Craig, J. Org. Chem. 1970, (35), 1721; Bauer, J. Org. Chem. 1963 (28), 1323; Hunt, J. Chem. Soc. 525-530 (1959) and Matsumura, Nippon Kagaku Zasshi, 74, 363 (1953).

Furthermore, the halogenated heterocycles of the formula (IIb) can be obtained from the corresponding hydroxy compounds $A(CR^2R^3)_n-OH$ by reaction with halogenating reagents, such as thionyl chloride or phosphorus oxychloride, see Angerstein, Ber. dtsch. Chem. Ges., 34, 3956 (1901); d'Atri, J. Med. Chem. 1984 (27), 1621-1629 or Sakamoto, Chem. Pharm. Bull. 28, 3362-8 (1980), or in the case where n=O, by reacting the amines of the formula $A-NH_2$ is a Sandmeyer-type reaction, see Tagaki, Chem. Pharm. Bull. 11, pp. 1382-8 (1963); Houben-Weyl, "Methoden der organischen Chemie" (Methods of Organic Chemistry), Vol. 10/3, p. 53 et seq., Georg Thieme Verlag, Stuttgart 1965, Vol. 5/3, p. et seq. 846 and Vol. 5/4, p. 437 et seq.

The heterocyclic amines $A-NH_2$ are known or may be prepared by processes which are known in principle, see "The Chemistry of Heterocyclic Compounds", Vol. XVI, (1962), Interscience Publ., NY & London and Supplement I (1970) of this handbook. Amino-substituted triazine derivatives are described by Smolin and Rapaport in "The Chemistry of Heterocyclic Compounds", Vol. XIII (1959), Interscience Publ. NY & London. The following patents describe specifically substituted heterocyclic amines: U.S. Pat. No. 4,515,626, U.S. Pat. No. 4,540,782, U.S. Pat. No. 4,339,267, U.S. Pat. No. 4,487,626 and U.S. Pat. No. 4,421,550. Further publications on the synthesis of bicyclic pyrimidines can be found in Braker, J. Am. Chem. Soc. 1947 (69), 3072; Mitler, Quart. J. Ind. Chem. Soc. 4, 152 (1927); Shrage; J. Org. Chem. 1951 (16), 1153; Caldwell, J. Am. Chem. Soc. 1941 (63), 2188 and Fissekis, J. Org. Chem. 1964 (29), 2670.

The compounds of the formula (II), (IIa), (IIb), (IIc) and their precursors which were used in the above described processes are novel in some cases and correspond in particular to the formula (II′)

(II′)

where

X' is COCl, CN, Cl, F, Br, I, p-tosyl, tetraalkylammonium, $N_3$, $CO_2R^{13}$, $CO_2CH_2C_6H_5$ or $E^1R^{18}$ and A, n, $R^{13}$, $E^1$ and $R^{18}$ have the meanings which have already been mentioned.

It is preferred to employ the heterocyclic compounds of the formula X ($X^3$=CN, Cl, F, Br, I, $N_3$, $CO_2R^{13}$, $CO_2$, $CH_2C_6H_5$ or $E^1R^{18}$) as starting materials for the preparation of the abovementioned intermediates; the compounds of the formula X may be prepared by reacting the compounds of the formula XI with acid chlorides of the formula XII or acid anhydrides of the formula XIII.

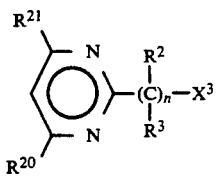 (X)

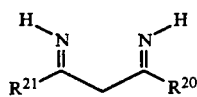 (XI)

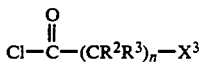 (XII)

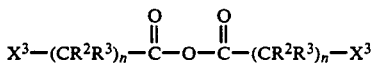 (XIII)

The reactions of the ketimines, amidates or imidates of the formula XI are carried out, for example, in an inert solvent, such as dichloromethane, toluene, tetrahydrofuran or 1,2-dimethoxyethane, in the presence of a base, such as triethylamine, potassium carbonate or N-ethyldiisopropylamine, in a temperature interval from −78° C. to 100° C., see Eilingsfeld, Chem. Ber. 101, 2426–2434 (1968). From the four compounds in question, Eilingsfeld however only described ethyl 4,6-diethoxypyridine-2-carboxylate and 2-chloromethyl-4,6-diethoxypyrimidine as prepared (see Chem. Ber. 101, 2426). In the case where n=O, the carboxylic esters which are employed as precursors for the preparation of the carboxylic acids of the formula (IIa) are accessible from the halogenated precursors A—$X^1$ by a Negishi-Kumada cross-coupling reaction, by reaction with appropriate organotin compounds, see Yamanaka; Chem. Pharm. Bull. 33, 4309–4313 (1985) and Sakamoto; Synthesis 1988, 485–486.

Specific heterocyclic precursors for the preparation of the compounds of the formula I are described in the following publications:

Sakamoto; Chem. Pharm. Bull. 32, 2005–2010 (1984); (methyl 4-methoxy-6-methylpyrimidine-2-carboxylate).

Sakasai, Heterocycles 1979, 235–238; Mekuskiene, Zh. Vses. Khim. O-va. 1976, 21(3), 348–349; Brown, Aust. J. Chem. 1974, 27, 2251–9 (methyl 4,6-dimethylpyrimidine-2-carboxylate; 4,6-dimethylpyrimidine-2-carboxylic acid).

Eilingsfeld, Chem. Ber. 1968, 101, 2426–2334; (ethyl 4,6-diethoxypyridine-2-carboxylate; 2-chloromethyl-4,6-diethoxypyrimidine).

Brown, Aust. J. Chem. 1977, 30, 621–627; (ethyl (4-chloro-6-methylpyrimidin-2-yl)acetate; methyl (4,6-dichloropyrimidin-2-yl)acetate)

Yamanaka, Heterocycles 1976, 5, 255–260 and Yamanaka, Chem. Pharm. Bull. 1979, 27, 2291–2294; (methyl 4-benzyloxy-6-methyl-2-pyrimidinylacetate, methyl 4-methoxy-6-methyl-2-pyrimidineylacetate, methyl 4-ethoxy-6-methyl-2-pyrimidinylacetate).

Brown, Aust. J. Chem. 1978, 31, 649–659; (methyl (4,6-dichloropyrimidin-2-yl)acetate; methyl (4-chloro-6-methoxypyrimidin-2-yl)acetate, methyl(4,6-dimethoxypyrimidin-2-yl)acetate; methyl (4-chloro-6-methylpyrimidin-2-yl)acetate; besides the corresponding carboxylic acids).

Yamanaka, Chem. Pharm. Bull. 1985, 33, 4309–4313, Chem. Pharm. Bull. 1981, 29, 2837–2843; Sakamoto, Chem. Pharm. Bull. 1980, 28, 3362–3368, Niitsuma, Heterocycles 1978, 10, 171–176; Kost, Khim, Geterotsikl. Soedin. 1978, 10, 1400–1405; Brown, Aust. J. Chem. 1974, 27, 2251–2259; Namaev, Khim. Geterotsikl. Soedin., Sb. 1: Azotsoderzhashchie Geterotsikly 1967, 354–359; (ethyl (4,6-dimethylpyrimidin-2-yl)acetate).

EP-A 154,132; (ethyl 1H-1-methyl-1,2,4-triazole-3-carboxylate).

FR-A 2,499,081; (methyl 1H-1-methyl-1,2,4-triazole-3-carboxylate).

Vakhatova, Khim, Geterotsikl. Soedin. 1981, 2, 264–267; (ethyl 4-chloro-6-methoxy-s-triazine-2-acetate).

Zaitseva, Zh. Obshch. Khim. 1964, 34, 2976–2979; Schaefer, J. Org. Chem. 1962, 27, 3608–3613; (ethyl 4,6-dimethyl-s-triazine-2-carboxylate).

Kober, J. Org. Chem. 1961, 26, 4705–4706; (ethyl 4,6-dichloro-s-triazine-2-acetate).

The compounds which are known correspond to the compounds of the formula (II'), where A is A1, r is 0, $E^2$ is CH and a) X' is $CO_2CH_3$, n is 0, $R^{20}/R^{21}$ is $OCH_3/CH_3$ b) X' is $CO_2C_2H_5$, n is 0, $R^{20}$ and $R^{21}$ each are $OC_2H_5$, c) X' is COOH or $CO_2CH_3$, n is 0, $R^{20}$ and $R^{21}$ each are $CH_3$, d) X' is Cl, n is 1, $R^2$ is $R^3$ is H, $R^{20}$ is $R^{21}$ is $OC_2H_5$, e) X' is $CO_2C_2H_5$, n is 1, $R^2$ is 1, $R^2$ is $R^3$ is H, $R^{20}/R^{21}$ is $Cl/CH_3$, f) X' is COOH or $COOCH_3$, n is 1, $R^2$ is $R^3$ is H, $R^{20}/R^{21}$ is benzyloxy/$CH_3$, $OCH_3/CH_3$, $OC_2H_5/CH_3$, Cl/Cl, Cl/$OCH_3$, $OCH_3/OCH_3$ or Cl/$CH_3$;

g) X' is $COOC_2H_5$, n is 1, $R^2$ is $R^3$ is H, $R^{20}/R^{21}$ is $CH_3/CH_3$, or correspond to compounds of the formula (II') in which h) A is A5, $R^{20}$ is H, $R^{22}$ is $CH_3$, n is 0, X' is $CO_2C_2H_5$ or $CO_2CH_3$, or correspond to compounds of the formula (II') in which i) A is A1, r is 0, $E^2$ is N, n is 0, $R^{20}/R^{21}$ is $CH_3/CH_3$ and X' is $CO_2C_2H_5$, j) A is A1, r is 0, $E^2$ is N, n is 1, $R^2$ is $R^3$ is H, $R^{20}/R^{21}$ is Cl/$OCH_3$ or Cl/Cl and X' is $CO_2C_2H_5$.

The invention therefore also relates to the intermediates of the formula (II') with the exception of the intermediates which are known.

In the case where m=0, the sulfonamides of the formula III which are used as intermediates in processes $a_1$) and $a_2$) are obtained from the corresponding anilines by diazotization and exchange of the diazo group for sulfur dioxide in the presence of a catalyst, such as copper(I) chloride, in hydrochloric acid or acetic acid, and reacting the sulfonyl chloride which has formed with ammonia, cf. Meerwein, Chem. Ber. 1957, 90, 841-852;

The intermediates of the formula III (with X=O and m=1 are obtained from the corresponding phenols by reaction with chlorosulfonyl isocyanate, followed by hydrolysis, cf. Lohaus, Chem. Ber. 1972, 105, 2791-2799.

The compounds of the formula III with X=NR$^4$ and m=1 are prepared in a known manner from the corresponding anilines by reaction with amidosulfochloride in the presence of an auxiliary base, such as triethylamine.

The sulfonamides of the formula III with X=CHR$^2$ and m=1 are obtained by customary methods from the corresponding benzyl halides by reaction with thiourea, followed by oxidation with chlorine and subsequent reaction with ammonia. The sulfonamides of the formula III with X=CHR$^2$ and m=1 are also obtained from the corresponding benzyl halides after conversion into the Grignard reagent by reaction with SO$_2$ and subsequent reaction of the sulfinate salt which has formed with hydroxylamine-O-sulfonic acid in a buffered aqueous solution.

The sulfonyl isocyanate of the formula VI are prepared by conventional processes which are known to the expert, see "Newer Methods of Preparative Organic Chemistry", Vol. VI, 223-241, Adademic Press, NY & London; Lohaus, Chem. Ber. 1972, 105, 2791-2799.

The compounds of the formula I according to the invention have an excellent herbicidal activity against a broad range of economically important monocotyledon and dicotyledon weeds. The active substances act equally well on perennial weeds which produce shoots from rhizomes, rootstocks or other perennial organs and which cannot be easily controlled. In this context, it does not matter if the substances are applied before sowing, as pre-emergence treatment or post-emergence treatment. Some representatives of the monocotyledon and dicotyledon weed flora which can be controlled by the compounds according to the invention may be mentioned individually as examples, but this is not to be taken to mean a restriction to certain species.

The monocotyledon weed species controlled include, for example, Avena, Lolium, Alopecurus, Phalaris, Echinochloa, Digitaria, Setaria etc and Cyperus species from the annual group, and the perennial species include Agropyron, Cynodon, Imperata and Sorghum etc, and also perennial Cyperus species.

Of the dicotyledon weed species, the range of action covers species such as, for example, Galium, Viola, Veronica, Lamium, Stellaria, Amaranthus, Sinapis, Ipomoea, Matricaria, Abutilon, Sida etc from the annual plants, and Convolvulus, Cirsium, Rumex, Artemisia etc from the perennials.

Excellent control of weeds occurring under the specific culture conditions in rice, such as, for example, Sagitaria, Alisma, Eleocharis, Scirpus, Cyperus etc, by the active substances according to the invention is also possible.

If the compounds according to the invention are applied to the soil surface before germination, either emergence of the weed seedlings is prevented completely, or the weeds grow until they have reached the cotyledon stage, but growth then comes to a standstill and, after a period of three to four weeks, the plants eventually die completely. When, in the post-emergence method, the active substances are applied to the green parts of the plants, growth also stops dramatically very soon after the treatment, and the weeds remain in the growth stage of the time of application, or, after a certain period of time, die more or less rapidly so that competition of the weeds, which is detrimental for the crop plants, can thus be prevented at a very early stage and in a sustained manner by using the novel compounds according to the invention.

Even though the compounds according to the invention have an excellent herbicidal activity against monocotyledon and dicotyledon weeds, crop plants of economically important crops such as, for example, wheat, barley, rye, rice, maize, sugar beet, cotton and soya beans, are damaged to a negligible extent only, or not at all. Thus, the present compounds are very suitable for selectively controlling undesired plant growth in agricultural plantations of useful plants.

In addition, the compounds according to the invention have growth-regulating properties in crop plants. They engage in the plant metabolism in a regulating manner and can thus be employed for facilitating harvesting, such as, for example, by provoking desiccation, abscission and stunted growth. Furthermore, they are suitable for generally regulating and inhibiting undesired vegetative growth, without simultaneously destroying the plants. Inhibition of vegetative growth plays an important role in many monocotyledon and dicotyledon crops because lodging can be reduced hereby, or prevented completely.

The compounds of the formula (I) or their combination with one or more of the mentioned herbicides or groups of herbicides can be formulated in several manners, depending on the biological and/or physicochemical parameters. Examples of possible formulations which are suitable are: wettable powders (WP), emulsifiable concentrates (EC), aqueous solutions (SC), emulsions, sprayable solutions, dispersions based on oil or water (SC), suspoemulsions (SC), dusting agents (DP), seed-dressing agents, granules for the soil or microgranules (FG), water-dispersible granules (WG), ULV formulations, microcapsules or waxes.

These individual types of formulation are known in principle and described, for example, in: Winnacker-Küchler, "Chemische Technologie" (Chemical Technology), Vol. 7, C. Hauser Verlag Munich, 4th Ed. 1986; van Falkenberg, "Pesticides Formulations", Marcel Dekker N.Y., 2nd Ed. 1972-73; K. Martens, "Spray Drying Handbook⇌, 3rd Ed. 1979, G. Goodwin Ltd. London.

The formulation auxiliaries required, such as inert materials, surfactants, solvents and other additives, are likewise known and are described, for example, in: Watkins, "Handbook of Insecticide Dust Diluents and Carriers", 2nd Ed., Darland Books, Caldwell, N.J.; H.v.Olphen, "Introduction to Clay Colloid Chemistry", 2nd Ed., J. Wiley & Sons, N.Y.; Marschen, "Solvents Guide", 2nd Ed., Interscience, N.Y. 1950; McCutcheon's, "Detergents and Emulsifiers Annual" MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive, Äthylenoxidaddukte" (Surface-active ethylene oxide adducts), Wiss. Verlagsgesell., Stuttgart 1976; Winnacker-Küchler, "Chemische Technologie" (Chemical Technology), Vol. 7, C. Hauser Verlag Munich, 4th Ed. 1986.

On the basis of these formulations, it is also possible to prepare combinations with other pesticidally active substances, fertilizers and/or growth regulators, for example in the form of a readymix or as a tank mix. Wettable powders are preparations which are uniformly dispersible in water and which, besides the active substance, also contain wetting agents, for example, polyoxyethylated alkylphenols, polyoxyethylated fatty alcohols, alkylsulfonates or alkylphenolsulfonates, and dispersing agents, for example, sodium ligninsulfonate, sodium 2,2'-dinaphthylmethane-6,6'-disulfonate, sodium dibutylnaphthalenesulfonate or sodium oleylmethyltaurinate, in addition, if appropriate, to a diluent or substance. Emulsifiable concentrates can be prepared, for example, by dissolving the active substance in an organic solvent, for example butanol, cyclohexanone, dimethylformamide, xylene and also higher-boiling aromatics or hydrocarbons, with the addition of one or more emulsifiers. Emulsifiers which can be used are, for example: calcium salts of alkylarylsulfonic acids, such as Ca dodecylbenzenesulfonate, or nonionic emulsifiers, such as fatty acid polyglycol esters, alkylaryl polyglycol ethers, fatty alcohol polyglycol ethers, propylene oxide/ethylene oxide condensation products, alkyl polyethers, sorbitan fatty acid esters, polyoxyethylene sorbitan fatty acid esters or polyoxyethylene sorbitol esters.

Dusting agents are obtained by grinding the active substance with finely divided solid substances, for example talc or natural clays, such as kaolin, bentonite or pyrophillite, or diatomaceous earth. Solid granules or microgranules can be produced either by spraying the active substance onto adsorptive, granulated inert material or by applying active substance concentrates onto the surface of carriers such as sand, kaolinites or granulated inert material, by means of binders, for example polyvinyl alcohol, sodium polyacrylate or alternatively mineral oils. Suitable active substances can also be granulated in the manner which is conventional for the preparation of fertilizer granules, if desired in a mixture with fertilizers.

The agrochemical preparations usually contain 0.1 to 99 percent by weight, in particular 0.1 to 95% by weight, of active substance of the formula (I), 1 to 99.9% by weight, in particular 5 to 99.8% by weight, of a solid or liquid additive, and 0 to 25% by weight, in particular 0.1 to 25% by weight, of a surfactant.

The active substance concentration in wettable powders is, for example, about 10 to 90% by weight; the remainder to 100% by weight comprises conventional formulation components. In the case of emulsifiable concentrates, the active substance concentration can be about 5 to 80% by weight. Dust-like formulations usually contain 5 to 20% by weight of active substance, sprayable solutions about 2 to 20% by weight. In the case of water-dispersible granules, the active substance content depends partly on whether the active compound is liquid or solid.

In general, the content is between 10 and 90% by weight in the water-dispersible granules.

In addition, the active substance formulations mentioned contain, if appropriate, the adhesives, wetting agents, dispersing agents, emulsifiers, penetrants, solvents, fillers or carriers which are conventional in each case.

For use, the formulations, present in commercially available form, are diluted, if appropriate, in a conventional manner, for example using water in the case of wettable powders, emulsifiable concentrates, dispersions and water-dispersible granules. Dust-like preparations and soil granules or microgranules and also sprayable solutions are usually not further diluted with other inert substances before use.

The application rate required of the compounds of the formula (I) varies with the external conditions, such as temperature, humidity, type of herbicide used, amongst others. It can vary within a wide range, for example between 0.005 and 10.0 kg/ha or more of active substance, preferably, however, it is between 0.01 and 5 kg/ha.

The following examples are intended to illustrate the invention:

A. Formulation examples a) A dusting agent is obtained by mixing 10 parts by weight of a compound of the formula (I) and 90 parts by weight of talc or inert substance, and comminuting the mixture in a hammer mill.

b) A wettable powder which is readily dispersible in water is obtained by mixing 25 parts by weight of a compound of the formula (I), 64 parts by weight of kaolin-containing quartz as the inert substance, 10 parts by weight of potassium ligninsulfonate and 1 part by weight of sodium oleoylmethyltaurinate as the wetting and dispersing agent, and grinding the mixture in a pinned disk mill.

c) A dispersion concentrate which is readily dispersible in water is obtained by mixing 20 parts by weight of a compound of the formula (I) with 6 parts by weight of alkylphenol polyglycol ether (®Triton X 207), 3 parts by weight of isotridecanol polyglycol ether (9 EO) and 71 parts by weight of a paraffinic mineral oil (boiling range for example about 255° to above 277° C), and grinding the mixture in a ball mill to fineness of below 5 microns.

d) An emulsifiable concentrate is obtained from 15 parts by weight of a compound of the formula (I), 75 parts by weight of cyclohexanone as the solvent and 10 parts by weight of oxethylated nonylphenol as the emulsifier.

e) Granules which are water-dispersible are obtained by mixing
75 parts by weight of a compound of the formula (I),
10 parts by weight of a compound of calcium ligninsulfonate,
5 parts by weight of a compound of sodium lauryl sulfate,
3 parts by weight of a compound of polyvinyl alcohol and
7 parts by weight of a compound of kaolin,
grinding the mixture on a pinned disk mill, and granulating the powder in a fluidized bed by water being sprayed on as the granulation liquid.

Water-dispersible granules are also obtained by homogenizing and pre-comminuting
25 parts by weight of a compound of the formula (I),
5 parts by weight of a compound of sodium 2,2'-dinaphthylmethane-6,6'-disulfonate,
2 parts by weight of a compound of sodium oleylmethyltaurinate,
1 parts by weight of a compound of polyvinyl alcohol,
17 parts by weight of a compound of calcium carbonate and
50 parts by weight of a compound of water
on a colloidal mill, followed by grinding on a pearl mill, and atomizing the suspension obtained in this manner in a spray tower by means of a single-substance valve, and drying.

CHEMICAL EXAMPLES

EXAMPLE 1

2-Ethoxycarbonyl-4,6-dimethoxypyrimidine 76 ml of N-ethyldiisopropylamine in 35 ml of dichloromethane are added dropwise at −35° C. to a suspension of 25.4 g of dimethyl malodiimidate dihydrochloride in 100 ml of dichloromethane. When the addition is complete, stirring is continued for 15 minutes, and 14 ml of oxalic acid ethyl ester chloride are then added dropwise at this temperature. The mixture is now allowed to come to room temperature, and stirring is continued for 2 hours. The mixture is poured onto 200 ml of ice water, and the organic phase is separated off and washed again twice with water. The organic phase is dried over $CaCl_2$ and concentrated. This gives 21.7 g of 2-ethoxycarbonyl-4,6-dimethoxypyrimidine of melting point 54°–55° C. (from hexane).

EXAMPLE 2

4,6-Dimethoxypyrimidine-2-carboxylic acid 17.1 g of 2-ethoxycarbonyl-4,6-dimethoxypyrimidine are dissolved in 300 ml of ethanol, and 3.4 g of sodium hydroxide in 50 ml of water are added. This solution is stirred for 4 hours at room temperature and refluxed for 1 hour. The mixture is cooled, and most of the ethanol is removed on a rotary evaporator. The residue is taken up in water and extracted using dichloromethane. The aqueous-alkaline phase is acidified to a pH of 2–3 using 6N hydrochloric acid, and any precipitated product is filtered off with suction. This gives 9.6 g of 4,6-dimethoxypyrimidine-2-carboxylic acid of melting point 155°–157° C.

EXAMPLE 3

1-Bromo-1-(4,6-dimethoxypyrimidin-2-yl)ethane 58.7 ml of 2-bromo-propionyl bromide in 200 ml of dichloromethane are added dropwise at −30° C. over the course of 1 hour to a stirred suspension of 101 g of dimethyl malodiimidate dihydrochloride and 266 g of potassium carbonate in 1500 ml of dichloromethane. The mixture is allowed to come to room temperature, stirring is continued for 4 hours, and the mixture is treated carefully with such an amount of water that the salts are entirely dissolved (cooling). The phases are separated, the organic phase is washed again twice using saturated sodium hydrogen carbonate solution and dried over potassium carbonate, and the solvent is distilled off. After the residue has been filtered over silica gel (eluent: dichloromethane), 37 g of 1-bromo-1-(4,6-dimethoxypyrimidin-2-yl)ethane are obtained.

$^1$H-NMR (CDCl$_3$): δ=2.05 (d, J=7 Hz; 3H); 3.98 (s, 6H); 5.08 (q, J=7 Hz; 1H); 5.93 (s, 1H).

2-Chloromethyl-4,6-dimethoxypyrimidine of melting point 40°–42° C. is prepared in the same way.

EXAMPLE 4

2-Cyanomethyl-4,6-dimethoxypyrimidine 16.7 g of dried sodium cyanide was dissolved in 850 ml of dimethyl sulfoxide at 90° C. under N$_2$ protective gas. At this temperature, 52.8 g of 2-chloromethyl-4,6-dimethoxypyrimidine, dissolved in 280 ml of dimethyl sulfoxide, are added dropwise over the course of 2 hours. Stirring is continued for 1 hour at 90° C., and the mixture is cooled to room temperature and poured into 300 ml of water. The aqueous phase is extracted seven times using ether, and the combined organic phases are washed using saturated aqueous sodium chloride solution, dried over magnesium sulfate and evaporated in a rotary evaporator. This gives 29.1 g of crude product, from which 2-cyanomethyl-4,6-dimethoxypyrimidines of melting point 65°–67° C. are obtained after column chromatography (SiO$_2$; CH$_2$Cl$_2$/CH$_3$OH; 98.5/1.5).

EXAMPLE 5

Methyl (4,6-dimethoxypyrimidin-2-yl)acetate

A powerful stream of hydrogen chloride gas is passed for 15 minutes into a solution of 230 ml of methyl acetate and 6.45 ml of methanol, at 0° C. to 10° C. 23.8 g of 2-cyanomethyl-4,6-dimethoxypyrimidine in 250 ml of methyl acetate are not added dropwise while more hydrogen chloride is passed in, and the passing-in of gas is stopped when the dropwise addition is complete, and stirring is continued for 5 hours at 10° C. to 15° C. 200 ml of absolute diethyl ether are added, the mixture is cooled to 5° C., and the precipitate is filtered off with suction under nitrogen. The residue is washed with ether and filtered off with suction until dry. This gives 31.5 g of the imidomethyl ester hydrochloride of melting point 110°–112° C., to which 250 ml of water are added, and the mixture is stirred for 4 hours at 40° C. The mixture is cooled to room temperature and extracted four times using four 150 ml portions of diethyl ether. The organic phase is dried over magnesium sulfate, and the solvent is distilled off. This gives 19.5 g of methyl (4,6-dimethoxypyrimidin-2-yl)acetate of boiling point 110° C./0.04 mbar (ball tube distillation).

EXAMPLE 6

(4,6-Dimethoxypyrimidin-2-yl)acetic acid 20 g of methyl (4,6-dimethoxypyrimidin-2-yl)acetate are stirred for 2 hours at 50° C. with 3.9 g of sodium hydroxide in 300 ml of water. The mixture is cooled to room temperature and extracted three times using diethyl ether, and the aqueous phase is acidified to pH 2 using 2N hydrochloric acid and extracted four times using 150 ml portions of ethyl acetate. The organic phase is dried over sodium sulfate, the solvent is distilled off, and the residue is dried in vacuo. This gives 13.1 g of (4,6-dimethoxypyrimidin-2-yl)acetic acid of melting point 175°–177° C.

EXAMPLE 7

2-Ethoxyphenyl sulfamate 2.2 g of water are added dropwise at 30° C. to 40° C. to a solution of 19.2 g of 2-ethoxyphenoxysulfonyl isocyanate in 150 ml of tetrachloromethane. The mixture is stirred at room temperature until the evolution of carbon dioxide has ceased and cooled to 0° C., the product is filtered off with suction, and the filter residue is washed with ice-cold tetrachloromethane. Drying in vacuo gives 16 g of 2-ethoxyphenyl sulfamate of melting point 62°–65° C.

EXAMPLE 8

1-(2-Methoxycarbonylphenyl)sulfuryl diamide

A solution of 5 g of amidosulfochloride in 40 ml of absolute dichloromethane is added dropwise to 6.4 g of methyl anthranilate and 4.4 g of triethylamine in 50 ml of absolute dichloromethane. Stirring is continued for 0.5 hour at 40° C. and then for 1 hour at room temperature, and the solvent is distilled off in a rotary evaporator. 100 ml of 1N hydrochloric acid are added to the residue, stirring of the mixture is continued for 0.5 hour, and the solid is filtered off with suction. The filter residue is washed thoroughly with water and dried in vacuo. This gives 7.9 g of 1-(2-methoxycarbonylphenyl)sulfuryl diamide of melting point 116°-118° C.

EXAMPLE 9

1-(2-Chlorophenyl)-3-[(4,6-dimethoxypyrimidin-2-yl(carbonyl]sulfuryl diamide

A solution of 2.1 g of 1-(2-chlorophenyl(sulfuryl diamide is added dropwise at 0° C.-2° C. to a mixture of 2.3 g of dicyclohexylcarbodiimide, 0.12 g of 4-dimethylaminopyrimidine and 2.2 g of 4,6-dimethoxypyrimidine-2-carboxylic acid in 40 ml of dichloromethane. Stirring is continued for 4 hours at this temperature, the mixture is allowed to stand at rom temperature overnight, and precipitated urea is filtered off with suction. The filtrate is stirred for 10 minutes with 100 ml of 1N sodium carbonate solution, the phases are separated, and the aqueous phase is extracted again twice using dichloromethane. The sodium carbonate alkaline phase is acidified to a pH of 2-3 and stirred for 15 minutes, and the precipitate is filtered off with suction and dried in vacuo. This gives 1.3 g of 1-(2-chlorophenyl)-3-[(4,6-dimethoxypyrimidin-2-yl(carbonyl]sulfuryl diamide of melting point 127°-129° C.

EXAMPLE 10

2,6-Dichlorophenyl N-[(4,6-dimethoxypyridin-2-yl)carbonyl]sulfamate 2.4 g of 2,6-dichlorophenyl sulfamate are added in portions at 0° C. to 2° C. to a mixture of 2.3 g of dicyclohexylcarbodiimide, 120 mg of 4-dimethylaminopyridine and 2.2 g of 4,6-dimethoxypyrimidine-2-carboxylic acid in 80 ml of absolute dichloromethane, and stirring is continued for 0.5 hour at 0° C. and 3 hours at room temperature. The mixture is filtered off with suction, the organic phase is washed with 100 ml of 1N hydrochloric acid and then with water and dried over sodium sulfate. The solvent is distilled off, and the residue is recrystallized from diisopropyl ether. This gives 3.2 g of 2,6-dichlorophenyl N-[(4,6-dimethoxypyrimidin-2-yl)carbonyl]sulfamate of melting point 136°-139° C.

EXAMPLE 11

N-[(2-(4,6)Dimethoxypyrimidin-2-yl)acetyl]-2-methoxycarbonylbenzylsulfonamide

A solution of 1.9 g of (4,6-dimethoxypyrimidin-2-yl)acetic acid in 40 ml of absolute dichloromethane is added dropwise at 0° C. to 2° C. to a solution of 1.9 g of dicyclohexylcarbodiimide, 100 mg of 4-dimethylaminopyridine and 2.1 g of 2-methoxycarbonylbenzylsulfonamide in 40 ml of absolute dichloromethane. Stirring is continued for 1 hour at 0° C., and the mixture is allowed to come to room temperature and stirred for about 0.5 hour. The solids are filtered off, and the filtrate is concentrated in a rotary evaporator. 100 ml of 2N sodium carbonate solution are added to the residue, the mixture is stirred for 0.5 hour at room temperature, and the solids are filtered off with suction. The sodium carbonate alkaline phase is extracted twice using diethyl ether, and a pH of 2-3 is established using concentrated hydrochloric acid. Stirring is continued for 15 minutes, the solids are filtered off with suction, the filter residue is washed once with water and twice with ether and dried in vacuo. This gives 2.4 g of N-[2-(4,6-dimethoxypyrimidin-2-yl)acetyl]-2-methoxycarbonylbenzylsulfonamide of melting point 98°-101° C.

EXAMPLE 12

N-[(4,6-Dimethoxypyrimidin-2-yl)carbonyl]-2-methoxycarbonylbenzylsulfonamide 2.2 g of 2-methoxycarbonylbenzenesulfonamide are added in portions at 0° C. to 2° C. to a mixture of 2.3 g of dicyclohexylcarbodiimide, 120 mg of 4-dimethylaminopyridine and 2.2 g of 4,6-dimethoxypyrimidine-2-carboxylic acid in 80 ml of absolute dichloromethane. The mixture is stirred for 0.5 hour at 0° C. and 2 hours at room temperature, and allowed to stand overnight. The urea which has precipitated is filtered off, the filtrate is concentrated in vacuo, and the residue is stirred for 0.5 hour with 100 ml of 2N sodium carbonate solution. The aqueous phase is extracted using ether, and a pH of 2-3 is established using concentrated hydrochloric acid. The product which has precipitated is filtered off with suction and dried in vacuo. This gives 1.3 g of N-[(4,6-dimethoxypyrimidin-2-yl)carbonyl]-2-methoxycarbonylbenzenesulfonamide of melting point 163°-165° C. (from ethyl acetate).

EXAMPLE 13

Ethyl 4-methoxy-6-methylpyrimidine-2-carboxylate 182 ml of triethylamine in 50 ml of dichloromethane are added dropwise at −30° C. to a stirred suspension of 70.2 g of methyl-3-amino-2-butenimidate dihydrochloride in 350 ml of dichloromethane. Stirring is continued for 0.5 hour at this temperature, and 42 ml of oxalic acid ethyl ester chloride are then added dropwise. Stirring is continued for 1 hour at −30° C., and the mixture is allowed to come to room temperature in the course of 12 hours. The organic phase is stirred several times with water, dried over $Na_2SO_4$ and concentrated. After filtration over silica gel (eluent: $CH_2Cl_2$), the residue is distilled in vacuo. This gives 51.5 g of ethyl 4-methoxy-6-methylpyrimidine-2-carboxylate of boiling point 105°-115° C./0.05 mbar.

EXAMPLE 14

4-Methoxy-6-methylpyrimidine-2-carboxylic acid

A solution of 11.5 g of sodium hydroxide in 156 ml of ethanol and 78 ml of water is added to a stirred solution of 51.5 g of ethyl 4-methoxy-6methylpyrimidine-2-carboxylate in 280 ml of ethanol. Stirring is continued for 12 hours at room temperature, and the sodium salt of the carboxylic acid, which has precipitated, is filtered off with suction. The sodium salt is transferred to a solution of 17.3 g of acetyl chloride in 220 ml of methanol, and the sodium chloride, which has precipitated, is filtered off with suction. The methanolic solution is evaporated on a rotary evaporator. This gives 30.9 g of 4-methoxy-6-methylpyrimidine-2-carboxylic acid of melting point 140°-141° C. as the residue.

EXAMPLE 15

2-Ethoxybenzylsulfonamide

A Grignard solution of 30.5 of 2-ethoxybenzyl chloride and 6.1 g of magnesium shavings in 250 ml of diethyl ether is added dropwise at −60° C. to −70° C. to 50 ml of sulfur dioxide. Stirring is continued for 0.5 hour at −70° C., the mixture is allowed to come to room temperature, and the salt magnesium 2-ethoxybenzylsulfinate which has formed (47 g, melting point:

134°-139° C., decomposition) is filtered off with suction. The sulfinate salt is dissolved in 900 ml of water and 16.4 g of anhydrous sodium acetate. To this are added 22.7 g of hydroxylamine-O-sulfonic acid at room temperature with stirring. After the mixture has been stirred for 12 hours, the product is filtered off with suction and dried in vacuo. This give 23.9 g of 2-ethoxybenzylsulfonamide of melting point: 92°-93° C.

EXAMPLE 16

2-Ethoxy-N-[4-methoxy-6-methylpyrimidin-2-yl(carbonyl]benzylsulfonamide 2.2 g of 2-ethoxybenzylsulfonamide are added in portions at 0° C. to 2° C. to a mixture of 2.3 g of dicyclohexylcarbodiimide, 120 mg of 4-dimethylaminopyridine and 2.0 g of 4-methoxy-6-methylpyrimidine-2-carboxylic acid in 80 ml of absolute dichloromethane, the mixture is stirred for 0.5 hour at 0° C., and stirring is continued for 3 hours at room temperature. The solids are filtered off with suction, the filtrate is evaporated on a rotary evaporator, and the residue is stirred in a mixture of acetone and 1M sodium carbonate solution. The aqueous solution is extracted using ether, a pH of 2–3 is established using concentrated HCl, and the mixture is extracted using dichloromethane. The dichloromethane phase is evaporated in a rotary evaporator, and the residue is recrystallized from ether/heptane. This gives 2.2 g of 2-ethoxy-N-[4-methoxy-6-methylpyrimidin-2-yl)carbonyl]-benzylsulfonamide of melting point: 111°-113° C.

The compounds of the tables below can be prepared analogously to the procedures described in Examples 1 to 16.

| L1 = | (benzene ring with positions 1,2,3,4 and substituents $R^5$ at 2, $R^6$ at 6, $R^7$ at 5) |
|---|---|

| | | |
|---|---|---|
| L1-1: | $R^5 = -CO_2CH_3$; | $R^6, R^7 = H$ |
| L1-2: | $R^5 = -CO_2CH_2CH_3$; | $R^6, R^7 = H$ |
| L1-3: | $R^5 = -CO_2CH(CH_3)_2$; | $R^6, R^7 = H$ |
| L1-4: | $R^5 = -CO_2CH_3$; | $R^6 = 5\text{-}OCF_2H$; $R^7 = H$ |
| L1-5: | $R^5 = -CO_2CH_3$; | $R^6 = 5\text{-}Cl$; $R^7 = H$ |
| L1-6: | $R^5 = -CO_2CH_3$; | $R^6 = 5\text{-}OCH_3$; $R^7 = H$ |
| L1-7: | $R^5 = -CON(CH_3)_2$; | $R^6, R^7 = H$ |
| L1-8: | $R^5 = -CF_3$; | $R^6, R^7 = H$ |
| L1-9: | $R^5 =$ (1,2,4-triazol-3-yl with N-CH$_2$CH$_3$); | $R^6, R^7 = H$ |
| L1-10: | $R^5 =$ (1,2,4-triazol-3-yl with N-CH$_3$); | $R^6, R^7 = H$ |
| L1-11: | $R^5 =$ (1,3,4-oxadiazol-2-yl); | $R^6, R^7 = H$ |
| L1-12: | $R^5 =$ (1,2,3-triazol-1-yl); | $R^6, R^7 = H$ |
| L1-13: | $R^5 =$ (pyrazol-3-yl with N-CH$_3$); | $R^6 = 6\text{-}Cl$; $R^7 = H$ |
| L1-14: | $R^5 =$ (1,2,4-triazol-3-yl with N-CH$_3$); | $R^6 = 5\text{-}OCH_3$; $R^7 = H$ |
| L1-15: | $R^5 = OCH_3$; | $R^6, R^7 = H$ |
| L1-16: | $R^5 = OC_2H_5$; | $R^6, R^7 = H$ |
| L1-17: | $R^5 = OCH(CH_3)_2$; | $R^6, R^7 = H$ |
| L1-18: | $R^5 = -OCH_2CH_2Cl$; | $R^6, R^7 = H$ |
| L1-19: | $R^5 = OCH_2CH_2-OCH_3$; | $R^6, R^7 = H$ |
| L1-20: | $R^5 = OCH_2CF_3$; | $R^6, R^7 = H$ |
| L1-21: | $R^5 = -OCF_2CF_3$; | $R^6, R^7 = H$ |
| L1-22: | $R^5 = OSO_2CH_3$; | $R^6, R^7 = H$ |
| L1-23: | $R^5 = -OSO_2CH_2CH_3$; | $R^6, R^7 = H$ |
| L1-24: | $R^5 = Br$; | $R^6, R^7 = H$ |
| L1-25: | $R^5 = F$; | $R^6, R^7 = H$ |
| L1-26: | $R^5 = Cl$; | $R^6, R^7 = H$ |
| L1-27: | $R^5 = Cl$; | $R^6 = 4\text{-}Cl$; $R^7 = 6\text{-}Cl$ |
| L1-28: | $R^5 = NO_2$; | $R^6, R^7 = H$ |
| L1-29: | $R^5 = N(CH_3)_2$; | $R^6, R^7 = H$ |
| L1-30: | $R^5 = -N(CH_3)CH_2CH_3$; | $R^6, R^7 = H$ |
| L1-31: | $R^5 = -N(CH_2CH_3)_2$; | $R^6, R^7 = H$ |
| L1-32: | $R^5 = CN$; | $R^6, R^7 = H$ |
| L1-33: | $R^5 = -CO-CH_3$; | $R^6, R^7 = H$ |
| L1-34: | $R^5 = F$ | $R^6 = 6\text{-}F$; $R^7 = H$ |
| L1-35: | $R^5 = Cl$; | $R^6 = 6\text{-}Cl$; $R^7 = H$ |
| L1-36: | $R^5 = Br$; | $R^6 = 6\text{-}Br$; $R^7 = H$ |
| L1-37: | $R^5 = NO_2$; | $R^6 = 6\text{-}CH_3$; $R^7 = H$ |
| L1-38: | $R^5 = CH_3$; | $R^6, R^7 = H$ |
| L1-39: | $R^5 = C_6H_5$; | $R^6, R^7 = H$ |
| L1-40: | $R^5 = -SO_2CH_3$; | $R^6, R^7 = H$ |
| L1-41: | $R^5 = -SO_2CH_2CH_3$; | $R^6, R^7 = H$ |
| L1-42: | $R^5 = -SO_2CH(CH_3)_2$; | $R^6, R^7 = H$ |
| L1-43: | $R^5 = -SO_2CH_2-CH_2-CH_3$; | $R^6, R^7 = H$ |
| L1-44: | $R^5 = -SO_2N(CH_3)_2$; | $R^6, R^7 = H$ |
| L1-45: | $R^5 = -CH_2Cl$; | $R^6, R^7 = H$ |
| L1-46: | $R^5 = -CH_2-OCH_3$; | $R^6, R^7 = H$ |
| L1-47: | $R^5 = -CH_2-N(CH_3)_2$; | $R^6, R^7 = H$ |
| L1-48: | $R^5 = -CH_2SCH_3$; | $R^6, R^7 = H$ |
| L1-49: | $R^5 = N_3$; | $R^6, R^7 = H$ |
| L1-50: | $R^5 = SCH_3$; | $R^6, R^7 = H$ |
| L1-51: | $R^5 = -SCH_2CH_3$; | $R^6, R^7 = H$ |
| L1-52: | $R^5 = -OCF_2H$; | $R^6, R^7 = H$ |
| L1-53: | $R^5 = -OCF_3$; | $R^6, R^7 = H$ |
| L1-54: | $R^5 = I$; | $R^6, R^7 = H$ |
| L1-55: | $R^5 = NO_2$; | $R^6 = 6\text{-}F$; $R^7 = H$ |
| L1-56: | $R^5 = NO_2$; | $R^6 = 6\text{-}Cl$; $R^7 = H$ |
| L1-57: | $R^5 = NO_2$; | $R^6 = 6\text{-}I$; $R^7 = H$ |
| L1-58: | $R^5 = Cl$; | $R^6 = 6\text{-}CH_3$; $R^7 = H$ |
| L1-59: | $R^5 = CO_2CH_3$; | $R^6 = 6\text{-}NO_2$; $R^7 = H$ |
| L1-60: | $R^5 = CO_2CH_3$; | $R^6 = 6\text{-}Cl$; $R^7 = H$ |
| L1-61: | $R^5 = CO_2CH_3$; | $R^6 = 6\text{-}I$; $R^7 = H$ |
| L1-62: | $R^5 = CO_2CH_3$; | $R^6 = 6\text{-}SO_2N(CH_3)_2$; $R^7 = H$ |
| L1-63: | $R^5 = F$; | $R^6 = 6\text{-}I$; $R^7 = H$ |
| L1-64: | $R^5 = F$; | $R^6 = 6\text{-}Cl$; $R^7 = H$ |
| L1-65: | $R^5 = Cl$; | $R^6 = 6\text{-}I$; $R^7 = H$ |
| L1-66: | $R^5 = SO_2N(CH_3)_2$; | $R^6 = 6\text{-}SO_2N(CH_3)_2$; $R^7 = H$ |
| L1-67: | $R^5 = SO_2N(CH_3)_2$; | $R^6 = 6\text{-}Cl$; $R^7 = H$ |
| L1-68: | $R^5 = SO_2N(CH_3)_2$; | $R^6 = 6\text{-}NO_2$; $R^7 = H$ |
| L3-1: | 3-Methoxy-carbonyl-2-thienyl | |
| L3-2: | 2-Methoxy-carbonyl-3-thienyl | |
| L3-3: | 2-Dimethylaminocarbonyl-3-thienyl | |
| L3-4: | 4-Methoxycarbonyl-3-thienyl | |
| L3-5: | 3-Chloro-2-thienyl | |

-continued

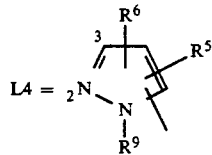

| | | |
|---|---|---|
| L4-1: | $R^5 = H$; $R^6 = 4\text{-}CO_2CH_3$; | $R^9 = CH_3$; free valency on C-5 |
| L4-2: | $R^5 = H$; $R^6 = 4\text{-}CO_2CH_2CH_3$; | $R^9 = CH_3$; free valency on C-5 |
| L4-3: | $R^5 = 3\text{-}Cl$; $R^6 = 4\text{-}CO_2CH_3$; | $R^9 = CH_3$; free valency on C-5 |
| L4-4: | $R^5 = 3\text{-}SO_2N(CH_3)_2$; $R^6 = H$; | $R^9 = CH_3$; free valency on C-4 |
| L4-5: | $R^5 = CH_3$; $R^6 = 5\text{-}CO_2CH_3$; | $R^9 = CH_3$; free valency on C-4 |

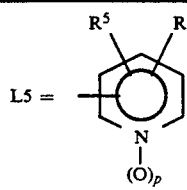

L5-1: 3-Methoxy-carbonyl-2-pyridyl
L5-2: 3-Methylsulfonyl-2-pyridyl
L5-3: 3-Dimethylaminocarbonyl-2-pyridyl
L5-4: 3-Ethoxycarbonyl-2-pyridyl
L5-5: 3-Dimethylaminosulfonyl-2-pyridyl
L5-6: 3-Trifluoromethyl-2-pyridyl
L5-7: 3-Ethoxy-2-pyridyl
L5-8: 2-Dimethylaminosulfonyl-3-pyridyl
L5-9: 2-Ethoxy-3-pyridyl
L5-10: 2-Bromo-3-pyridyl

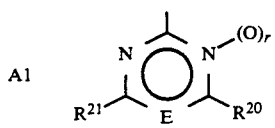

| | | |
|---|---|---|
| A1-1: | $R^{20}, R^{21} = OCH_3$; | $E = CH; r = 0$ |
| A1-2: | $R^{20} = Cl, R^{21} = OCH_3$; | $E = CH; r = 0$ |
| A1-3: | $R^{20} = CH_3; R^{21} = OCH_3$; | $E = CH; r = 0$ |
| A1-4: | $R^{20}, R^{21} = CH_3$; | $E = CH; r = 0$ |
| A1-5: | $R^{20} = CH_3; R^{21} = $ ![dioxolane] | $E = CH; r = 0$ |
| A1-6: | $R^{20} = OC_2H_5; R^{21} = OCH_3$ | $E = CH; r = 0$ |
| A1-7: | $R^{20} = C_2H_5; R^{21} = CH_3$; | $E = CH; r = 0$ |
| A1-8: | $R^{20} = -OCF_2H; R^{21} = OCH_3$; | $E = CH; r = 0$ |
| A1-9: | $R^{20} = OCH_2OCH_3; R^{21} = OCH_3$; | $E = CH; r = 0$ |
| A1-10: | $R^{20} = OCH_2CF_3; R^{21} = OCH_3$; | $E = CH; r = 0$ |
| A1-11: | $R^{20}, R^{21} = -OCF_2H$ | $E = CH; r = 0$ |
| A1-12: | $R^{20} = CH_2F; R^{21} = OCH_3$; | $E = CH; r = 0$ |
| A1-13: | $R^{20} = $ cyclopropyl; $R^{21} = OCH_3$; | $E = CH; r = 0$ |
| A1-14: | $R^{20} = $ cyclopropyl; $R^{21} = CH_3$; | $E = CH; r = 0$ |
| A1-15: | $R^{20} = -CH(OCH_3)_2; R^{21} = CH_3$; | $E = CH; r = 0$ |
| A1-16: | $R^{20} = H; R^{21} = CH_3$; | $E = CH; r = 0$ |
| A1-17: | $R^{20} = H; R^{21} = OCH_3$; | $E = CH; r = 0$ |
| A1-18: | $R^{20}, R^{21} = OCH_3$; | $E = N; r = 0$ |
| A1-19: | $R^{20} = CH_3; R^{21} = OCH_3$; | $E = N; r = 0$ |
| A1-20: | $R^{20}, R^{21} = CH_3$ | $E = N; r = 0$ |
| A1-21: | $R^{21} = OCH_3; R^{20} = NHCH_3$; | $E = N; r = 0$ |
| A1-22: | $R^{21} = OC_2H_5; R^{20} = NH-CH_3$; | $E = N; r = 0$ |
| A1-23: | $R^{20} = SCH_3; R^{21} = CH_3$; | $E = N; r = 0$ |
| A1-24: | $R^{20}, R^{21} = OCH_3$ | $E = CH; r = 1$ |
| A1-25: | $R^{20}, R^{21} = CH_3$ | $E = CH; r = 1$ |

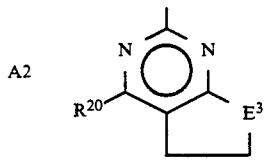

| | | |
|---|---|---|
| A2-1: | $R^{20} = OCH_3$ | $E^3 = O$ |
| A2-2: | $R^{20} = CH_3$ | $E^3 = O$ |
| A2-3: | $R^{20} = Cl$ | $E^3 = O$ |
| A2-4: | $R^{20} = OCH_3$ | $E^3 = CH_2$ |

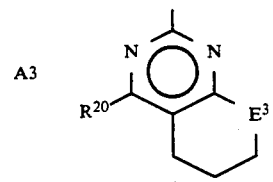

| | | |
|---|---|---|
| A3-1: | $R^{20} = OCH_3$ | $E^3 = O$ |
| A3-2: | $R^{20} = OCH_2CH_3$ | $E^3 = O$ |
| A3-3: | $R^{20} = Cl$ | $E^3 = O$ |
| A3-4: | $R^{20} = CH_3$ | $E^3 = $ |

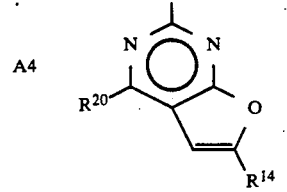

| | | |
|---|---|---|
| A4-1: | $R^{20} = OCH_3$ | $R^{14} = CH_3$ |
| A4-2: | $R^{20} = CH_3$ | $R^{14} = CH_3$ |
| A4-3: | $R^{20} = OCH_3$ | $R^{14} = H$ |
| A4-4: | $R^{20} = OCH_2CH_3$ | $R^{14} = H$ |

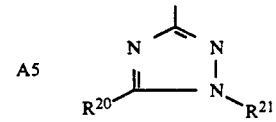

| | | |
|---|---|---|
| A5-1: | $R^{20} = OCH_3$ | $R^{21} = CH_3$ |
| A5-2: | $R^{20} = CH_3$ | $R^{21} = CH_3$ |
| A5-3: | $R^{20} = Cl$ | $R^{21} = CH_3$ |
| A5-4: | $R^{20} = OCH_3$ | $R^{21} = CH_2CH_3$ |

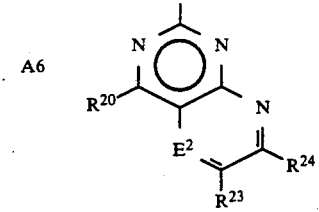

| | | |
|---|---|---|
| A6-1: | $R^{20} = OCH_3$ | $R^{23}, R^{24} = H$ $E^2 = N$ |
| A6-2: | $R^{20} = OCH_3$ | $R^{23} = H; R^{24} = OCH_3$ |

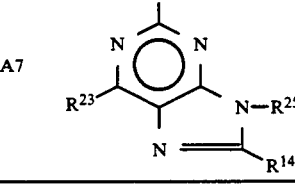

| | | |
|---|---|---|
| A7-1: | $R^{14} = OCH_3$ | $R^{23} = OCH_3$ | $R^{25} = CH_3$ |
| A7-2: | $R^{14} = CH_3$ | $R^{23} = OCH_3$ | $R^{25} = CH_3$ |
| A7-3: | $R^{14} = OCH_3$ | $R^{23} = CH_3$ | $R^{25} = CH_3$ |
| A7-4: | $R^{14} = CH_3$ | $R^{23} = CH_3$ | $R^{25} = CH_3$ |

-continued

A7-5: $R^{14}$ = Cl    $R^{23}$ = Cl    $R^{25}$ = $CH_3$

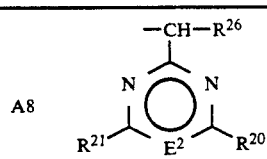

A8

| | $R^{20}$ | $R^{21}$ | $R^{26}$ | $E^2$ |
|---|---|---|---|---|
| A8-1: | $OCH_3$ | $OCH_3$ | H | CH |
| A8-2: | " | " | $CH_3$ | CH |
| A8-3: | " | " | $C_2H_5$ | CH |
| A8-4: | $CH_3$ | Cl | H | CH |
| A8-5: | $CH_3$ | $OCH_3$ | H | CH |
| A8-6: | Cl | Cl | H | CH |
| A8-7: | $OCH_3$ | Cl | H | CH |
| A8-8: | $CH_3$ | $CH_3$ | H | CH |
| A8-9: | $OC_2H_5$ | $CH_3$ | H | CH |
| A8-10: | Cl | Cl | H | N |
| A8-11: | Cl | $OCH_3$ | H | N |
| A8-12: | $N(CH_3)_2$ | $N(CH_3)_2$ | H | N |
| A8-13: | $OCH_3$ | $OCH_3$ | H | N |
| A8-14: | $OCH_3$ | $CH_3$ | H | N |

TABLE 1

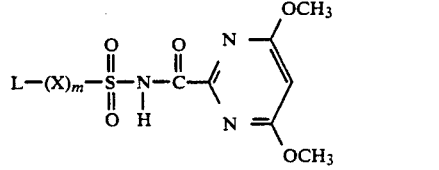

| Example No. | L | X | m | Melting point [°C.] |
|---|---|---|---|---|
| 1 | L1-1 | — | 0 | 163–165 |
| 2 | L1-2 | — | 0 | 128–130 |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 159–162 |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | 224–226 |
| 16 | L1-16 | — | 0 | 190–192 |
| 17 | L1-17 | — | 0 | |
| 18 | L1-18 | — | 0 | |
| 19 | L1-19 | — | 0 | 142–144 |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | 159–161 |
| 26 | L1-26 | — | 0 | 165–167 |
| 27 | L1-27 | — | 0 | |
| 28 | L1-28 | — | 0 | 183–185 |
| 29 | L1-29 | — | 0 | |
| 30 | L1-30 | — | 0 | |
| 31 | L1-31 | — | 0 | |
| 32 | L1-32 | — | 0 | 168–169 |
| 33 | L1-33 | — | 0 | |
| 34 | L1-34 | — | 0 | |
| 35 | L1-35 | — | 0 | 187–189 |
| 36 | L1-36 | — | 0 | |
| 37 | L1-37 | — | 0 | 204–210 |
| 38 | L1-38 | — | 0 | 167–169 |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |

TABLE 1-continued

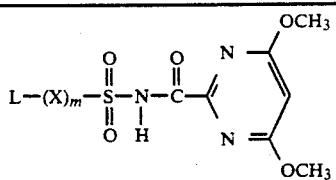

| Example No. | L | X | m | Melting point [°C.] |
|---|---|---|---|---|
| 44 | L1-44 | — | 0 | 245–248 |
| 45 | L1-45 | — | 0 | 168–170 |
| 46 | L1-46 | — | 0 | |
| 47 | L1-47 | — | 0 | 232–237 |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | 164–166 |
| 54 | L1-54 | — | 0 | |
| 55 | L1-1 | $CH_2$ | 1 | 124–126 |
| 56 | L1-2 | $CH_2$ | 1 | |
| 57 | L1-3 | $CH_2$ | 1 | |
| 58 | L1-4 | $CH_2$ | 1 | |
| 59 | L1-5 | $CH_2$ | 1 | |
| 60 | L1-6 | $CH_2$ | 1 | |
| 61 | L1-7 | $CH_2$ | 1 | |
| 62 | L1-8 | $CH_2$ | 1 | 173–174 |
| 63 | L1-9 | $CH_2$ | 1 | |
| 64 | L1-10 | $CH_2$ | 1 | |
| 65 | L1-11 | $CH_2$ | 1 | |
| 66 | L1-12 | $CH_2$ | 1 | |
| 67 | L1-13 | $CH_2$ | 1 | |
| 68 | L1-14 | $CH_2$ | 1 | |
| 69 | L1-15 | $CH_2$ | 1 | 145–147 |
| 70 | L1-16 | $CH_2$ | 1 | 146–148 |
| 71 | L1-17 | $CH_2$ | 1 | |
| 72 | L1-18 | $CH_2$ | 1 | |
| 73 | L1-19 | $CH_2$ | 1 | |
| 74 | L1-20 | $CH_2$ | 1 | |
| 75 | L1-21 | $CH_2$ | 1 | 138–142 |
| 76 | L1-22 | $CH_2$ | 1 | 112–116 |
| 77 | L1-23 | $CH_2$ | 1 | 121–126 |
| 78 | L1-24 | $CH_2$ | 1 | 145–148 |
| 79 | L1-25 | $CH_2$ | 1 | 125–127 |
| 80 | L1-26 | $CH_2$ | 1 | 126–128 |
| 81 | L1-27 | $CH_2$ | 1 | |
| 82 | L1-28 | $CH_2$ | 1 | 159–161 |
| 83 | L1-29 | $CH_2$ | 1 | |
| 84 | L1-30 | $CH_2$ | 1 | |
| 85 | L1-31 | $CH_2$ | 1 | |
| 86 | L1-32 | $CH_2$ | 1 | |
| 87 | L1-33 | $CH_2$ | 1 | |
| 88 | L1-34 | $CH_2$ | 1 | 163–166 |
| 89 | L1-35 | $CH_2$ | 1 | 185–187 |
| 90 | L1-36 | $CH_2$ | 1 | |
| 91 | L1-37 | $CH_2$ | 1 | 194–196 |
| 92 | L1-38 | $CH_2$ | 1 | 150–152 |
| 93 | L1-39 | $CH_2$ | 1 | |
| 94 | L1-40 | $CH_2$ | 1 | 138–142 |
| 95 | L1-41 | $CH_2$ | 1 | 136–140 |
| 96 | L1-42 | $CH_2$ | 1 | |
| 97 | L1-43 | $CH_2$ | 1 | |
| 98 | L1-44 | $CH_2$ | 1 | 165–166 |
| 99 | L1-45 | $CH_2$ | 1 | |
| 100 | L1-46 | $CH_2$ | 1 | 127–132 |
| 101 | L1-47 | $CH_2$ | 1 | |
| 102 | L1-48 | $CH_2$ | 1 | |
| 103 | L1-49 | $CH_2$ | 1 | |
| 104 | L1-50 | $CH_2$ | 1 | |
| 105 | L1-51 | $CH_2$ | 1 | |
| 106 | L1-52 | $CH_2$ | 1 | 148–152 |
| 107 | L1-53 | $CH_2$ | 1 | 104–166 |
| 108 | L1-54 | $CH_2$ | 1 | 142–146 |
| 109 | L1-1 | O | 1 | 128–130 |
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |

TABLE 1-continued

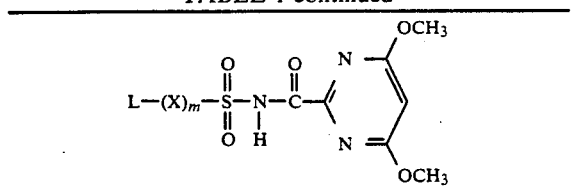

| Example No. | L | X | m | Melting point [°C.] |
|---|---|---|---|---|
| 116 | L1-8 | O | 1 | 125–127 |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | 87–92 |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | 144–146 |
| 135 | L1-27 | O | 1 | 148–152 |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | 121–124 |
| 144 | L1-36 | O | 1 | |
| 145 | L1-37 | O | 1 | |
| 146 | L1-38 | O | 1 | |
| 147 | L1-39 | O | 1 | |
| 148 | L1-40 | O | 1 | |
| 149 | L1-41 | O | 1 | 168–170 |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | 188–193 |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | 156–158 |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | 129–131 |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |
| 184 | L1-22 | NH | 1 | |
| 185 | L1-23 | NH | 1 | |
| 186 | L1-24 | NH | 1 | |
| 187 | L1-25 | NH | 1 | |

TABLE 1-continued

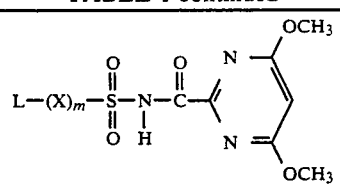

| Example No. | L | X | m | Melting point [°C.] |
|---|---|---|---|---|
| 188 | L1-26 | NH | 1 | 127–129 |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | 166–168 |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | 186–187 |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | 132–136 |
| 219 | L3-3 | — | 0 | |
| 220 | L3-4 | — | 0 | |
| 221 | L3-5 | — | 0 | 179–181 |
| 222 | L3-1 | CH$_2$ | 1 | |
| 223 | L3-2 | CH$_2$ | 1 | |
| 224 | L3-3 | CH$_2$ | 1 | |
| 225 | L3-4 | CH$_2$ | 1 | |
| 226 | L3-5 | CH$_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | 164–167 |
| 234 | L3-3 | NH | 1 | |
| 235 | L3-4 | NH | 1 | |
| 236 | L3-5 | NH | 1 | |
| 237 | L4-1 | — | 0 | 171–174 |
| 238 | L4-2 | — | 0 | 174–175 |
| 239 | L4-3 | — | 0 | |
| 240 | L4-4 | — | 0 | |
| 241 | L4-5 | — | 0 | |
| 242 | L4-1 | CH$_2$ | 1 | |
| 243 | L4-2 | CH$_2$ | 1 | |
| 244 | L4-3 | CH$_2$ | 1 | |
| 245 | L4-4 | CH$_2$ | 1 | |
| 246 | L4-5 | CH$_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |
| 256 | L4-5 | NH | 1 | |
| 257 | L5-1 | — | 0 | 152–154 |
| 258 | L5-2 | — | 0 | |
| 259 | L5-3 | — | 0 | 177–180 |

TABLE 1-continued

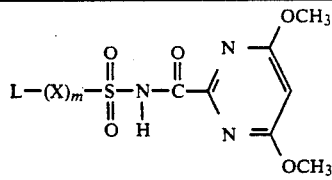

| Example No. | L | X | m | Melting point [°C.] |
|---|---|---|---|---|
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | $CH_2$ | 1 | |
| 268 | L5-2 | $CH_2$ | 1 | |
| 269 | L5-3 | $CH_2$ | 1 | |
| 270 | L5-4 | $CH_2$ | 1 | |
| 271 | L5-5 | $CH_2$ | 1 | |
| 272 | L5-6 | $CH_2$ | 1 | |
| 273 | L5-7 | $CH_2$ | 1 | |
| 274 | L5-8 | $CH_2$ | 1 | |
| 275 | L5-9 | $CH_2$ | 1 | |
| 276 | L5-10 | $CH_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |
| 291 | L5-5 | NH | 1 | |
| 292 | L5-6 | NH | 1 | |
| 293 | L5-7 | NH | 1 | |
| 294 | L5-8 | NH | 1 | |
| 295 | L5-9 | NH | 1 | |
| 296 | L5-10 | NH | 1 | |
| 297 | L1-55 | $CH_2$ | 1 | 175–177 |
| 298 | L1-56 | $CH_2$ | 1 | 199–201 |
| 299 | L1-57 | $CH_2$ | 1 | |
| 300 | L1-58 | $CH_2$ | 1 | 170–172 |
| 301 | L1-59 | $CH_2$ | 1 | 166–168 |
| 302 | L1-60 | $CH_2$ | 1 | |
| 303 | L1-61 | $CH_2$ | 1 | 190–191 |
| 304 | L1-62 | $CH_2$ | 1 | |
| 305 | L1-63 | $CH_2$ | 1 | |
| 306 | L1-64 | $CH_2$ | 1 | 166–168 |
| 307 | L1-65 | $CH_2$ | 1 | |
| 308 | L1-66 | $CH_2$ | 1 | |
| 309 | L1-67 | $CH_2$ | 1 | |
| 310 | L1-68 | $CH_2$ | 1 | |

TABLE 2

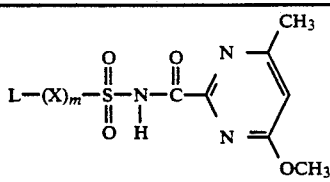

| Example No. | L | X | m | Melting point [°C.] |
|---|---|---|---|---|
| 1 | L1-1 | — | 0 | 151–158 |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 157 |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | 141–143 |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | 136–142 |
| 27 | L1-27 | — | 0 | |
| 28 | L1-28 | — | 0 | 159–163 |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | 165–167 |
| 38 | L1-38 | — | 0 | 92–97 |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | 185–186 |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | 110–112 |
| 54 | L1-54 | — | 0 | |
| 55 | L1-1 | $CH_2$ | 1 | 117–120 |
| 56 | L1-2 | $CH_2$ | 1 | |
| 57 | L1-3 | $CH_2$ | 1 | |
| 58 | L1-4 | $CH_2$ | 1 | |
| 59 | L1-5 | $CH_2$ | 1 | |
| 60 | L1-6 | $CH_2$ | 1 | |
| 61 | L1-7 | $CH_2$ | 1 | |
| 62 | L1-8 | $CH_2$ | 1 | 148–151 |
| 63 | L1-9 | $CH_2$ | 1 | |
| 64 | L1-10 | $CH_2$ | 1 | |
| 65 | L1-11 | $CH_2$ | 1 | |
| 66 | L1-12 | $CH_2$ | 1 | |
| 67 | L1-13 | $CH_2$ | 1 | |
| 68 | L1-14 | $CH_2$ | 1 | |
| 69 | L1-15 | $CH_2$ | 1 | |
| 70 | L1-16 | $CH_2$ | 1 | 111–113 |
| 71 | L1-17 | $CH_2$ | 1 | |
| 72 | L1-18 | $CH_2$ | 1 | |
| 73 | L1-19 | $CH_2$ | 1 | |
| 74 | L1-20 | $CH_2$ | 1 | |
| 75 | L1-21 | $CH_2$ | 1 | 91–97 |
| 76 | L1-22 | $CH_2$ | 1 | 102–107 |
| 77 | L1-23 | $CH_2$ | 1 | 105–109 |
| 78 | L1-24 | $CH_2$ | 1 | |

TABLE 2-continued

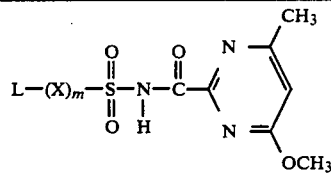

| Example No. | L | X | m | Melting point [°C.] |
|---|---|---|---|---|
| 79 | L1-25 | CH$_2$ | 1 | |
| 80 | L1-26 | CH$_2$ | 1 | 173–174 |
| 81 | L1-27 | CH$_2$ | 1 | |
| 82 | L1-28 | CH$_2$ | 1 | 110–113 |
| 83 | L1-29 | CH$_2$ | 1 | |
| 84 | L1-30 | CH$_2$ | 1 | |
| 85 | L1-31 | CH$_2$ | 1 | |
| 86 | L1-32 | CH$_2$ | 1 | |
| 87 | L1-33 | CH$_2$ | 1 | |
| 88 | L1-34 | CH$_2$ | 1 | |
| 89 | L1-35 | CH$_2$ | 1 | |
| 90 | L1-36 | CH$_2$ | 1 | |
| 91 | L1-37 | CH$_2$ | 1 | 178–180 |
| 92 | L1-38 | CH$_2$ | 1 | 136–137 |
| 93 | L1-39 | CH$_2$ | 1 | |
| 94 | L1-40 | CH$_2$ | 1 | 97–101 |
| 95 | L1-41 | CH$_2$ | 1 | 101–105 |
| 96 | L1-42 | CH$_2$ | 1 | |
| 97 | L1-43 | CH$_2$ | 1 | |
| 98 | L1-44 | CH$_2$ | 1 | 118–122 |
| 99 | L1-45 | CH$_2$ | 1 | |
| 100 | L1-46 | CH$_2$ | 1 | |
| 101 | L1-47 | CH$_2$ | 1 | |
| 102 | L1-48 | CH$_2$ | 1 | |
| 103 | L1-49 | CH$_2$ | 1 | |
| 104 | L1-50 | CH$_2$ | 1 | |
| 105 | L1-51 | CH$_2$ | 1 | |
| 106 | L1-52 | CH$_2$ | 1 | 108–112 |
| 107 | L1-53 | CH$_2$ | 1 | 125–127 |
| 108 | L1-54 | CH$_2$ | 1 | 183–184 |
| 109 | L1-1 | O | 1 | |
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |
| 145 | L1-37 | O | 1 | |
| 146 | L1-38 | O | 1 | |
| 147 | L1-39 | O | 1 | |
| 148 | L1-40 | O | 1 | |
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |
| 184 | L1-22 | NH | 1 | |
| 185 | L1-23 | NH | 1 | |
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | |
| 219 | L3-3 | — | 0 | |
| 220 | L3-4 | — | 0 | |
| 221 | L3-5 | — | 0 | |
| 222 | L3-1 | CH$_2$ | 1 | |

TABLE 2-continued

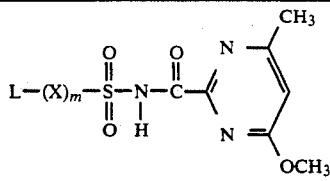

| Example No. | L | X | m | Melting point [°C.] |
|---|---|---|---|---|
| 223 | L3-2 | CH$_2$ | 1 | |
| 224 | L3-3 | CH$_2$ | 1 | |
| 225 | L3-4 | CH$_2$ | 1 | |
| 226 | L3-5 | CH$_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | |
| 239 | L4-3 | — | 0 | |
| 240 | L4-4 | — | 0 | |
| 241 | L4-5 | — | 0 | |
| 242 | L4-1 | CH$_2$ | 1 | |
| 243 | L4-2 | CH$_2$ | 1 | |
| 244 | L4-3 | CH$_2$ | 1 | |
| 245 | L4-4 | CH$_2$ | 1 | |
| 246 | L4-5 | CH$_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |
| 256 | L4-5 | NH | 1 | |
| 257 | L5-1 | — | 0 | |
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | CH$_2$ | 1 | |
| 268 | L5-2 | CH$_2$ | 1 | |
| 269 | L5-3 | CH$_2$ | 1 | |
| 270 | L5-4 | CH$_2$ | 1 | |
| 271 | L5-5 | CH$_2$ | 1 | |
| 272 | L5-6 | CH$_2$ | 1 | |
| 273 | L5-7 | CH$_2$ | 1 | |
| 274 | L5-8 | CH$_2$ | 1 | |
| 275 | L5-9 | CH$_2$ | 1 | |
| 276 | L5-10 | CH$_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |
| 291 | L5-5 | NH | 1 | |
| 292 | L5-6 | NH | 1 | |
| 293 | L5-7 | NH | 1 | |
| 294 | L5-8 | NH | 1 | |

TABLE 2-continued

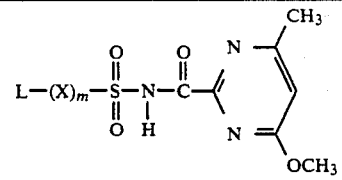

| Example No. | L | X | m | Melting point [°C.] |
|---|---|---|---|---|
| 295 | L5-9 | NH | 1 | |
| 296 | L5-10 | NH | 1 | |
| 297 | L1-55 | CH$_2$ | 1 | |
| 298 | L1-56 | CH$_2$ | 1 | |
| 299 | L1-57 | CH$_2$ | 1 | |
| 300 | L1-58 | CH$_2$ | 1 | |
| 301 | L1-59 | CH$_2$ | 1 | 138–139 |
| 302 | L1-60 | CH$_2$ | 1 | |
| 303 | L1-61 | CH$_2$ | 1 | |
| 304 | L1-62 | CH$_2$ | 1 | |
| 305 | L1-63 | CH$_2$ | 1 | |
| 306 | L1-64 | CH$_2$ | 1 | |
| 307 | L1-65 | CH$_2$ | 1 | |
| 308 | L1-66 | CH$_2$ | 1 | |
| 309 | L1-67 | CH$_2$ | 1 | |
| 310 | L1-68 | CH$_2$ | 1 | |

TABLE 3

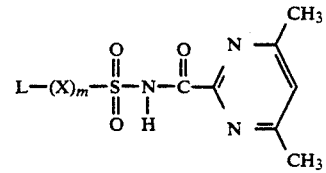

| Example No. | L | X | m | Melting point [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | 162–164 |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | 186–188 |
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |

TABLE 3-continued

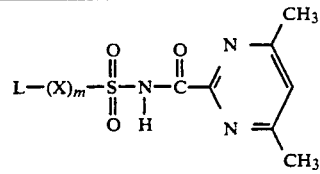

| Example No. | L | X | m | Melting point [°C.] |
|---|---|---|---|---|
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | | |
| 54 | L1-54 | — | 0 | |
| 55 | L1-1 | CH$_2$ | 1 | |
| 56 | L1-2 | CH$_2$ | 1 | |
| 57 | L1-3 | CH$_2$ | 1 | |
| 58 | L1-4 | CH$_2$ | 1 | |
| 59 | L1-5 | CH$_2$ | 1 | |
| 60 | L1-6 | CH$_2$ | 1 | |
| 61 | L1-7 | CH$_2$ | 1 | |
| 62 | L1-8 | CH$_2$ | 1 | 184–186 |
| 63 | L1-9 | CH$_2$ | 1 | |
| 64 | L1-10 | CH$_2$ | 1 | |
| 65 | L1-11 | CH$_2$ | 1 | |
| 66 | L1-12 | CH$_2$ | 1 | |
| 67 | L1-13 | CH$_2$ | 1 | |
| 68 | L1-14 | CH$_2$ | 1 | |
| 69 | L1-15 | CH$_2$ | 1 | |
| 70 | L1-16 | CH$_2$ | 1 | |
| 71 | L1-17 | CH$_2$ | 1 | |
| 72 | L1-18 | CH$_2$ | 1 | |
| 73 | L1-19 | CH$_2$ | 1 | |
| 74 | L1-20 | CH$_2$ | 1 | |
| 75 | L1-21 | CH$_2$ | 1 | |
| 76 | L1-22 | CH$_2$ | 1 | |
| 77 | L1-23 | CH$_2$ | 1 | |
| 78 | L1-24 | CH$_2$ | 1 | |
| 79 | L1-25 | CH$_2$ | 1 | |
| 80 | L1-26 | CH$_2$ | 1 | |
| 81 | L1-27 | CH$_2$ | 1 | |
| 82 | L1-28 | CH$_2$ | 1 | |
| 83 | L1-29 | CH$_2$ | 1 | |
| 84 | L1-30 | CH$_2$ | 1 | |
| 85 | L1-31 | CH$_2$ | 1 | |
| 86 | L1-32 | CH$_2$ | 1 | |
| 87 | L1-33 | CH$_2$ | 1 | |
| 88 | L1-34 | CH$_2$ | 1 | |
| 89 | L1-35 | CH$_2$ | 1 | |
| 90 | L1-36 | CH$_2$ | 1 | |
| 91 | L1-37 | CH$_2$ | 1 | |
| 92 | L1-38 | CH$_2$ | 1 | |
| 93 | L1-39 | CH$_2$ | 1 | |
| 94 | L1-40 | CH$_2$ | 1 | |
| 95 | L1-41 | CH$_2$ | 1 | |
| 96 | L1-42 | CH$_2$ | 1 | |
| 97 | L1-43 | CH$_2$ | 1 | |
| 98 | L1-44 | CH$_2$ | 1 | |
| 99 | L1-45 | CH$_2$ | 1 | |
| 100 | L1-46 | CH$_2$ | 1 | |
| 101 | L1-47 | CH$_2$ | 1 | |
| 102 | L1-48 | CH$_2$ | 1 | |
| 103 | L1-49 | CH$_2$ | 1 | |
| 104 | L1-50 | CH$_2$ | 1 | |
| 105 | L1-51 | CH$_2$ | 1 | |
| 106 | L1-52 | CH$_2$ | 1 | |
| 107 | L1-53 | CH$_2$ | 1 | |
| 108 | L1-54 | CH$_2$ | 1 | |
| 109 | L1-1 | O | 1 | |
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |
| 145 | L1-37 | O | 1 | |
| 146 | L1-38 | O | 1 | |
| 147 | L1-39 | O | 1 | |
| 148 | L1-40 | O | 1 | |
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |
| 184 | L1-22 | NH | 1 | |
| 185 | L1-23 | NH | 1 | |

TABLE 3-continued

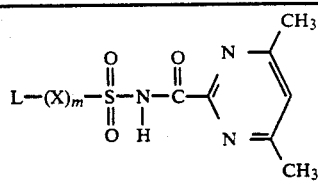

| Example No. | L | X | m | Melting point [°C.] |
|---|---|---|---|---|
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | |
| 219 | L3-3 | — | 0 | |
| 220 | L3-4 | — | 0 | |
| 221 | L3-5 | — | 0 | |
| 222 | L3-1 | $CH_2$ | 1 | |
| 223 | L3-2 | $CH_2$ | 1 | |
| 224 | L3-3 | $CH_2$ | 1 | |
| 225 | L3-4 | $CH_2$ | 1 | |
| 226 | L3-5 | $CH_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | |
| 239 | L4-3 | — | 0 | |
| 240 | L4-4 | — | 0 | |
| 241 | L4-5 | — | 0 | |
| 242 | L4-1 | $CH_2$ | 1 | |
| 243 | L4-2 | $CH_2$ | 1 | |
| 244 | L4-3 | $CH_2$ | 1 | |
| 245 | L4-4 | $CH_2$ | 1 | |
| 246 | L4-5 | $CH_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |
| 256 | L4-5 | NH | 1 | |
| 257 | L5-1 | — | 0 | |

TABLE 3-continued

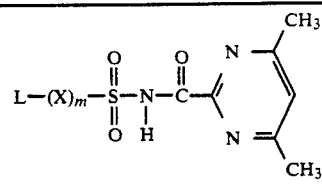

| Example No. | L | X | m | Melting point [°C.] |
|---|---|---|---|---|
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | $CH_2$ | 1 | |
| 268 | L5-2 | $CH_2$ | 1 | |
| 269 | L5-3 | $CH_2$ | 1 | |
| 270 | L5-4 | $CH_2$ | 1 | |
| 271 | L5-5 | $CH_2$ | 1 | |
| 272 | L5-6 | $CH_2$ | 1 | |
| 273 | L5-7 | $CH_2$ | 1 | |
| 274 | L5-8 | $CH_2$ | 1 | |
| 275 | L5-9 | $CH_2$ | 1 | |
| 276 | L5-10 | $CH_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |
| 291 | L5-5 | NH | 1 | |
| 292 | L5-6 | NH | 1 | |
| 293 | L5-7 | NH | 1 | |
| 294 | L5-8 | NH | 1 | |
| 295 | L5-9 | NH | 1 | |
| 296 | L5-10 | NH | 1 | |
| 297 | L1-55 | $CH_2$ | 1 | |
| 298 | L1-56 | $CH_2$ | 1 | |
| 299 | L1-57 | $CH_2$ | 1 | |
| 300 | L1-58 | $CH_2$ | 1 | |
| 301 | L1-59 | $CH_2$ | 1 | |
| 302 | L1-60 | $CH_2$ | 1 | |
| 303 | L1-61 | $CH_2$ | 1 | |
| 304 | L1-62 | $CH_2$ | 1 | |
| 305 | L1-63 | $CH_2$ | 1 | |
| 306 | L1-64 | $CH_2$ | 1 | |
| 307 | L1-65 | $CH_2$ | 1 | |
| 308 | L1-66 | $CH_2$ | 1 | |
| 309 | L1-67 | $CH_2$ | 1 | |
| 310 | L1-68 | $CH_2$ | 1 | |

TABLE 4

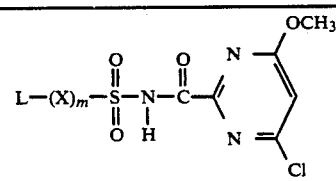

| Example No. | L | X | m | Melting point [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |

TABLE 4-continued

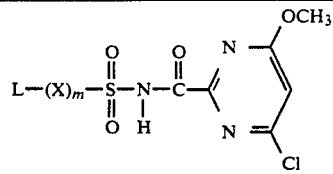

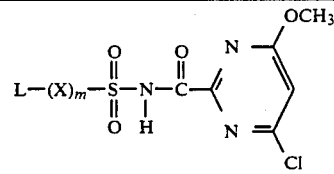

| Example No. | L | X | m | Melting point [°C.] |
|---|---|---|---|---|
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-1 | $CH_2$ | 1 | |
| 56 | L1-2 | $CH_2$ | 1 | |
| 57 | L1-3 | $CH_2$ | 1 | |
| 58 | L1-4 | $CH_2$ | 1 | |
| 59 | L1-5 | $CH_2$ | 1 | |
| 60 | L1-6 | $CH_2$ | 1 | |
| 61 | L1-7 | $CH_2$ | 1 | |
| 62 | L1-8 | $CH_2$ | 1 | |
| 63 | L1-9 | $CH_2$ | 1 | |
| 64 | L1-10 | $CH_2$ | 1 | |
| 65 | L1-11 | $CH_2$ | 1 | |
| 66 | L1-12 | $CH_2$ | 1 | |
| 67 | L1-13 | $CH_2$ | 1 | |
| 68 | L1-14 | $CH_2$ | 1 | |
| 69 | L1-15 | $CH_2$ | 1 | |
| 70 | L1-16 | $CH_2$ | 1 | |
| 71 | L1-17 | $CH_2$ | 1 | |
| 72 | L1-18 | $CH_2$ | 1 | |
| 73 | L1-19 | $CH_2$ | 1 | |
| 74 | L1-20 | $CH_2$ | 1 | |
| 75 | L1-21 | $CH_2$ | 1 | |
| 76 | L1-22 | $CH_2$ | 1 | |
| 77 | L1-23 | $CH_2$ | 1 | |
| 78 | L1-24 | $CH_2$ | 1 | |
| 79 | L1-25 | $CH_2$ | 1 | |
| 80 | L1-26 | $CH_2$ | 1 | |
| 81 | L1-27 | $CH_2$ | 1 | |
| 82 | L1-28 | $CH_2$ | 1 | |
| 83 | L1-29 | $CH_2$ | 1 | |
| 84 | L1-30 | $CH_2$ | 1 | |
| 85 | L1-31 | $CH_2$ | 1 | |
| 86 | L1-32 | $CH_2$ | 1 | |
| 87 | L1-33 | $CH_2$ | 1 | |
| 88 | L1-34 | $CH_2$ | 1 | |
| 89 | L1-35 | $CH_2$ | 1 | |
| 90 | L1-36 | $CH_2$ | 1 | |
| 91 | L1-37 | $CH_2$ | 1 | |
| 92 | L1-38 | $CH_2$ | 1 | |
| 93 | L1-39 | $CH_2$ | 1 | |
| 94 | L1-40 | $CH_2$ | 1 | |
| 95 | L1-41 | $CH_2$ | 1 | |
| 96 | L1-42 | $CH_2$ | 1 | |
| 97 | L1-43 | $CH_2$ | 1 | |
| 98 | L1-44 | $CH_2$ | 1 | |
| 99 | L1-45 | $CH_2$ | 1 | |
| 100 | L1-46 | $CH_2$ | 1 | |
| 101 | L1-47 | $CH_2$ | 1 | |
| 102 | L1-48 | $CH_2$ | 1 | |
| 103 | L1-49 | $CH_2$ | 1 | |
| 104 | L1-50 | $CH_2$ | 1 | |
| 105 | L1-51 | $CH_2$ | 1 | |
| 106 | L1-52 | $CH_2$ | 1 | |
| 107 | L1-53 | $CH_2$ | 1 | |
| 108 | L1-54 | $CH_2$ | 1 | |
| 109 | L1-1 | O | 1 | |
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |
| 145 | L1-37 | O | 1 | |
| 146 | L1-38 | O | 1 | |
| 147 | L1-39 | O | 1 | |
| 148 | L1-40 | O | 1 | |

TABLE 4-continued

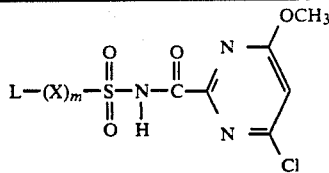

| Example No. | L | X | m | Melting point [°C.] |
|---|---|---|---|---|
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |
| 184 | L1-22 | NH | 1 | |
| 185 | L1-23 | NH | 1 | |
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | |
| 219 | L3-3 | — | 0 | |
| 220 | L3-4 | — | 0 | |

TABLE 4-continued

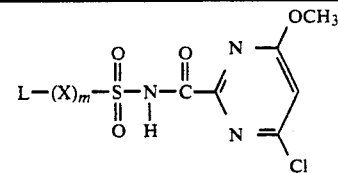

| Example No. | L | X | m | Melting point [°C.] |
|---|---|---|---|---|
| 221 | L3-5 | — | 0 | |
| 222 | L3-1 | CH$_2$ | 1 | |
| 223 | L3-2 | CH$_2$ | 1 | |
| 224 | L3-3 | CH$_2$ | 1 | |
| 225 | L3-4 | CH$_2$ | 1 | |
| 226 | L3-5 | CH$_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | |
| 239 | L4-3 | — | 0 | |
| 240 | L4-4 | — | 0 | |
| 241 | L4-5 | — | 0 | |
| 242 | L4-1 | CH$_2$ | 1 | |
| 243 | L4-2 | CH$_2$ | 1 | |
| 244 | L4-3 | CH$_2$ | 1 | |
| 245 | L4-4 | CH$_2$ | 1 | |
| 246 | L4-5 | CH$_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |
| 256 | L4-5 | NH | 1 | |
| 257 | L5-1 | — | 0 | |
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | CH$_2$ | 1 | |
| 268 | L5-2 | CH$_2$ | 1 | |
| 269 | L5-3 | CH$_2$ | 1 | |
| 270 | L5-4 | CH$_2$ | 1 | |
| 271 | L5-5 | CH$_2$ | 1 | |
| 272 | L5-6 | CH$_2$ | 1 | |
| 273 | L5-7 | CH$_2$ | 1 | |
| 274 | L5-8 | CH$_2$ | 1 | |
| 275 | L5-9 | CH$_2$ | 1 | |
| 276 | L5-10 | CH$_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |
| 291 | L5-5 | NH | 1 | |
| 292 | L5-6 | NH | 1 | |

TABLE 4-continued

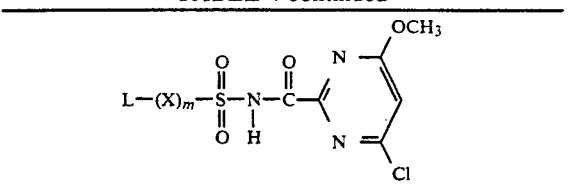

| Example No. | L | X | m | Melting point [°C.] |
|---|---|---|---|---|
| 293 | L5-7 | NH | 1 | |
| 294 | L5-8 | NH | 1 | |
| 295 | L5-9 | NH | 1 | |
| 296 | L5-10 | NH | 1 | |
| 297 | L1-55 | CH$_2$ | 1 | |
| 298 | L1-56 | CH$_2$ | 1 | |
| 299 | L1-57 | CH$_2$ | 1 | |
| 300 | L1-58 | CH$_2$ | 1 | |
| 301 | L1-59 | CH$_2$ | 1 | |
| 302 | L1-60 | CH$_2$ | 1 | |
| 303 | L1-61 | CH$_2$ | 1 | |
| 304 | L1-62 | CH$_2$ | 1 | |
| 305 | L1-63 | CH$_2$ | 1 | |
| 306 | L1-64 | CH$_2$ | 1 | |
| 307 | L1-65 | CH$_2$ | 1 | |
| 308 | L1-66 | CH$_2$ | 1 | |
| 309 | L1-67 | CH$_2$ | 1 | |
| 310 | L1-68 | CH$_2$ | 1 | |

TABLE 5

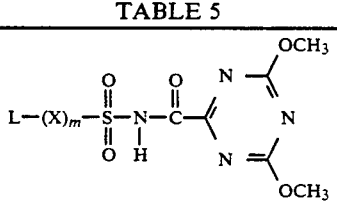

| Example No. | L | X | m | Melting point [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |

TABLE 5-continued

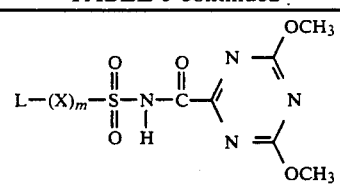

| Example No. | L | X | m | Melting point [°C.] |
|---|---|---|---|---|
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-1 | CH$_2$ | 1 | |
| 56 | L1-2 | CH$_2$ | 1 | |
| 57 | L1-3 | CH$_2$ | 1 | |
| 58 | L1-4 | CH$_2$ | 1 | |
| 59 | L1-5 | CH$_2$ | 1 | |
| 60 | L1-6 | CH$_2$ | 1 | |
| 61 | L1-7 | CH$_2$ | 1 | |
| 62 | L1-8 | CH$_2$ | 1 | |
| 63 | L1-9 | CH$_2$ | 1 | |
| 64 | L1-10 | CH$_2$ | 1 | |
| 65 | L1-11 | CH$_2$ | 1 | |
| 66 | L1-12 | CH$_2$ | 1 | |
| 67 | L1-13 | CH$_2$ | 1 | |
| 68 | L1-14 | CH$_2$ | 1 | |
| 69 | L1-15 | CH$_2$ | 1 | |
| 70 | L1-16 | CH$_2$ | 1 | |
| 71 | L1-17 | CH$_2$ | 1 | |
| 72 | L1-18 | CH$_2$ | 1 | |
| 73 | L1-19 | CH$_2$ | 1 | |
| 74 | L1-20 | CH$_2$ | 1 | |
| 75 | L1-21 | CH$_2$ | 1 | |
| 76 | L1-22 | CH$_2$ | 1 | |
| 77 | L1-23 | CH$_2$ | 1 | |
| 78 | L1-24 | CH$_2$ | 1 | |
| 79 | L1-25 | CH$_2$ | 1 | |
| 80 | L1-26 | CH$_2$ | 1 | |
| 81 | L1-27 | CH$_2$ | 1 | |
| 82 | L1-28 | CH$_2$ | 1 | |
| 83 | L1-29 | CH$_2$ | 1 | |
| 84 | L1-30 | CH$_2$ | 1 | |
| 85 | L1-31 | CH$_2$ | 1 | |
| 86 | L1-32 | CH$_2$ | 1 | |
| 87 | L1-33 | CH$_2$ | 1 | |
| 88 | L1-34 | CH$_2$ | 1 | |
| 89 | L1-35 | CH$_2$ | 1 | |
| 90 | L1-36 | CH$_2$ | 1 | |
| 91 | L1-37 | CH$_2$ | 1 | |
| 92 | L1-38 | CH$_2$ | 1 | |
| 93 | L1-39 | CH$_2$ | 1 | |
| 94 | L1-40 | CH$_2$ | 1 | |
| 95 | L1-41 | CH$_2$ | 1 | |
| 96 | L1-42 | CH$_2$ | 1 | |
| 97 | L1-43 | CH$_2$ | 1 | |
| 98 | L1-44 | CH$_2$ | 1 | |
| 99 | L1-45 | CH$_2$ | 1 | |
| 100 | L1-46 | CH$_2$ | 1 | |
| 101 | L1-47 | CH$_2$ | 1 | |
| 102 | L1-48 | CH$_2$ | 1 | |
| 103 | L1-49 | CH$_2$ | 1 | |
| 104 | L1-50 | CH$_2$ | 1 | |
| 105 | L1-51 | CH$_2$ | 1 | |
| 106 | L1-52 | CH$_2$ | 1 | |
| 107 | L1-53 | CH$_2$ | 1 | |
| 108 | L1-54 | CH$_2$ | 1 | |
| 109 | L1-1 | O | 1 | |
| 110 | L1-2 | O | 1 | |
| 111 | L1-3 | O | 1 | |

TABLE 5-continued

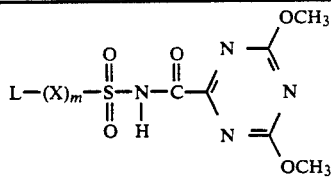

| Example No. | L | X | m | Melting point [°C.] |
|---|---|---|---|---|
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |
| 145 | L1-37 | O | 1 | |
| 146 | L1-38 | O | 1 | |
| 147 | L1-39 | O | 1 | |
| 148 | L1-40 | O | 1 | |
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |

TABLE 5-continued

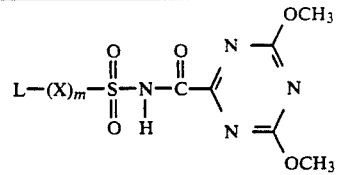

| Example No. | L | X | m | Melting point [°C.] |
|---|---|---|---|---|
| 184 | L1-22 | NH | 1 | |
| 185 | L1-23 | NH | 1 | |
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | |
| 219 | L3-3 | — | 0 | |
| 220 | L3-4 | — | 0 | |
| 221 | L3-5 | — | 0 | |
| 222 | L3-1 | $CH_2$ | 1 | |
| 223 | L3-2 | $CH_2$ | 1 | |
| 224 | L3-3 | $CH_2$ | 1 | |
| 225 | L3-4 | $CH_2$ | 1 | |
| 226 | L3-5 | $CH_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | |
| 239 | L4-3 | — | 0 | |
| 240 | L4-4 | — | 0 | |
| 241 | L4-5 | — | 0 | |
| 242 | L4-1 | $CH_2$ | 1 | |
| 243 | L4-2 | $CH_2$ | 1 | |
| 244 | L4-3 | $CH_2$ | 1 | |
| 245 | L4-4 | $CH_2$ | 1 | |
| 246 | L4-5 | $CH_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |

TABLE 5-continued

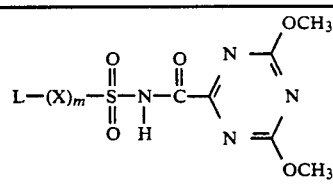

| Example No. | L | X | m | Melting point [°C.] |
|---|---|---|---|---|
| 256 | L4-5 | NH | 1 | |
| 257 | L5-1 | — | 0 | |
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | CH$_2$ | 1 | |
| 268 | L5-2 | CH$_2$ | 1 | |
| 269 | L5-3 | CH$_2$ | 1 | |
| 270 | L5-4 | CH$_2$ | 1 | |
| 271 | L5-5 | CH$_2$ | 1 | |
| 272 | L5-6 | CH$_2$ | 1 | |
| 273 | L5-7 | CH$_2$ | 1 | |
| 274 | L5-8 | CH$_2$ | 1 | |
| 275 | L5-9 | CH$_2$ | 1 | |
| 276 | L5-10 | CH$_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |
| 291 | L5-5 | NH | 1 | |
| 292 | L5-6 | NH | 1 | |
| 293 | L5-7 | NH | 1 | |
| 294 | L5-8 | NH | 1 | |
| 295 | L5-9 | NH | 1 | |
| 296 | L5-10 | NH | 1 | |
| 297 | L1-55 | CH$_2$ | 1 | |
| 298 | L1-56 | CH$_2$ | 1 | |
| 299 | L1-57 | CH$_2$ | 1 | |
| 300 | L1-58 | CH$_2$ | 1 | |
| 301 | L1-59 | CH$_2$ | 1 | |
| 302 | L1-60 | CH$_2$ | 1 | |
| 303 | L1-61 | CH$_2$ | 1 | |
| 304 | L1-62 | CH$_2$ | 1 | |
| 305 | L1-63 | CH$_2$ | 1 | |
| 306 | L1-64 | CH$_2$ | 1 | |
| 307 | L1-65 | CH$_2$ | 1 | |
| 308 | L1-66 | CH$_2$ | 1 | |
| 309 | L1-67 | CH$_2$ | 1 | |
| 310 | L1-68 | CH$_2$ | 1 | |

TABLE 6

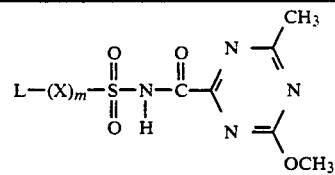

| Example No. | L | X | m | Melting point [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-1 | CH$_2$ | 1 | |
| 56 | L1-2 | CH$_2$ | 1 | |
| 57 | L1-3 | CH$_2$ | 1 | |
| 58 | L1-4 | CH$_2$ | 1 | |
| 59 | L1-5 | CH$_2$ | 1 | |
| 60 | L1-6 | CH$_2$ | 1 | |
| 61 | L1-7 | CH$_2$ | 1 | |
| 62 | L1-8 | CH$_2$ | 1 | |
| 63 | L1-9 | CH$_2$ | 1 | |
| 64 | L1-10 | CH$_2$ | 1 | |
| 65 | L1-11 | CH$_2$ | 1 | |
| 66 | L1-12 | CH$_2$ | 1 | |
| 67 | L1-13 | CH$_2$ | 1 | |
| 68 | L1-14 | CH$_2$ | 1 | |
| 69 | L1-15 | CH$_2$ | 1 | |
| 70 | L1-16 | CH$_2$ | 1 | |
| 71 | L1-17 | CH$_2$ | 1 | |
| 72 | L1-18 | CH$_2$ | 1 | |
| 73 | L1-19 | CH$_2$ | 1 | |
| 74 | L1-20 | CH$_2$ | 1 | |

TABLE 6-continued

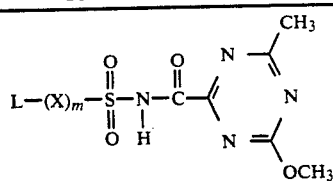

| Example No. | L | X | m | Melting point [°C.] |
|---|---|---|---|---|
| 75 | L1-21 | CH$_2$ | 1 | |
| 76 | L1-22 | CH$_2$ | 1 | |
| 77 | L1-23 | CH$_2$ | 1 | |
| 78 | L1-24 | CH$_2$ | 1 | |
| 79 | L1-25 | CH$_2$ | 1 | |
| 80 | L1-26 | CH$_2$ | 1 | |
| 81 | L1-27 | CH$_2$ | 1 | |
| 82 | L1-28 | CH$_2$ | 1 | |
| 83 | L1-29 | CH$_2$ | 1 | |
| 84 | L1-30 | CH$_2$ | 1 | |
| 85 | L1-31 | CH$_2$ | 1 | |
| 86 | L1-32 | CH$_2$ | 1 | |
| 87 | L1-33 | CH$_2$ | 1 | |
| 88 | L1-34 | CH$_2$ | 1 | |
| 89 | L1-35 | CH$_2$ | 1 | |
| 90 | L1-36 | CH$_2$ | 1 | |
| 91 | L1-37 | CH$_2$ | 1 | |
| 92 | L1-38 | CH$_2$ | 1 | |
| 93 | L1-39 | CH$_2$ | 1 | |
| 94 | L1-40 | CH$_2$ | 1 | |
| 95 | L1-41 | CH$_2$ | 1 | |
| 96 | L1-42 | CH$_2$ | 1 | |
| 97 | L1-43 | CH$_2$ | 1 | |
| 98 | L1-44 | CH$_2$ | 1 | |
| 99 | L1-45 | CH$_2$ | 1 | |
| 100 | L1-46 | CH$_2$ | 1 | |
| 101 | L1-47 | CH$_2$ | 1 | |
| 102 | L1-48 | CH$_2$ | 1 | |
| 103 | L1-49 | CH$_2$ | 1 | |
| 104 | L1-50 | CH$_2$ | 1 | |
| 105 | L1-51 | CH$_2$ | 1 | |
| 106 | L1-52 | CH$_2$ | 1 | |
| 107 | L1-53 | CH$_2$ | 1 | |
| 108 | L1-54 | CH$_2$ | 1 | |
| 109 | L1-1 | O | 1 | |
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |
| 145 | L1-37 | O | 1 | |
| 146 | L1-38 | O | 1 | |

TABLE 6-continued

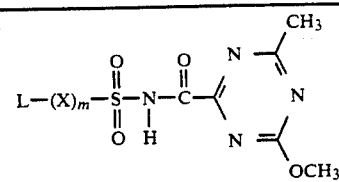

| Example No. | L | X | m | Melting point [°C.] |
|---|---|---|---|---|
| 147 | L1-39 | O | 1 | |
| 148 | L1-40 | O | 1 | |
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |
| 184 | L1-22 | NH | 1 | |
| 185 | L1-23 | NH | 1 | |
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | |

TABLE 6-continued

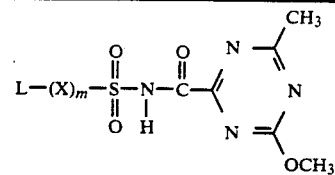

| Example No. | L | X | m | Melting point [°C.] |
|---|---|---|---|---|
| 219 | L3-3 | — | 0 | |
| 220 | L3-4 | — | 0 | |
| 221 | L3-5 | — | 0 | |
| 222 | L3-1 | CH$_2$ | 1 | |
| 223 | L3-2 | CH$_2$ | 1 | |
| 224 | L3-3 | CH$_2$ | 1 | |
| 225 | L3-4 | CH$_2$ | 1 | |
| 226 | L3-5 | CH$_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | |
| 239 | L4-3 | — | 0 | |
| 240 | L4-4 | — | 0 | |
| 241 | L4-5 | — | 0 | |
| 242 | L4-1 | CH$_2$ | 1 | |
| 243 | L4-2 | CH$_2$ | 1 | |
| 244 | L4-3 | CH$_2$ | 1 | |
| 245 | L4-4 | CH$_2$ | 1 | |
| 246 | L4-5 | CH$_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |
| 256 | L4-5 | NH | 1 | |
| 257 | L5-1 | — | 0 | |
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | CH$_2$ | 1 | |
| 268 | L5-2 | CH$_2$ | 1 | |
| 269 | L5-3 | CH$_2$ | 1 | |
| 270 | L5-4 | CH$_2$ | 1 | |
| 271 | L5-5 | CH$_2$ | 1 | |
| 272 | L5-6 | CH$_2$ | 1 | |
| 273 | L5-7 | CH$_2$ | 1 | |
| 274 | L5-8 | CH$_2$ | 1 | |
| 275 | L5-9 | CH$_2$ | 1 | |
| 276 | L5-10 | CH$_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |

TABLE 6-continued

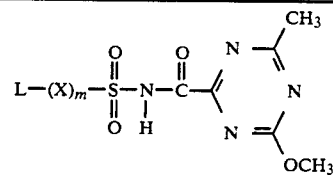

| Example No. | L | X | m | Melting point [°C.] |
|---|---|---|---|---|
| 291 | L5-5 | NH | 1 | |
| 292 | L5-6 | NH | 1 | |
| 293 | L5-7 | NH | 1 | |
| 294 | L5-8 | NH | 1 | |
| 295 | L5-9 | NH | 1 | |
| 296 | L5-10 | NH | 1 | |
| 297 | L1-55 | CH$_2$ | 1 | |
| 298 | L1-56 | CH$_2$ | 1 | |
| 299 | L1-57 | CH$_2$ | 1 | |
| 300 | L1-58 | CH$_2$ | 1 | |
| 301 | L1-59 | CH$_2$ | 1 | |
| 302 | L1-60 | CH$_2$ | 1 | |
| 303 | L1-61 | CH$_2$ | 1 | |
| 304 | L1-62 | CH$_2$ | 1 | |
| 305 | L1-63 | CH$_2$ | 1 | |
| 306 | L1-64 | CH$_2$ | 1 | |
| 307 | L1-65 | CH$_2$ | 1 | |
| 308 | L1-66 | CH$_2$ | 1 | |
| 309 | L1-67 | CH$_2$ | 1 | |
| 310 | L1-68 | CH$_2$ | 1 | |

TABLE 7

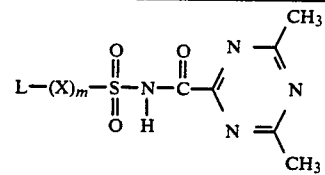

| Example No. | L | X | m | Melting point [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |

TABLE 7-continued

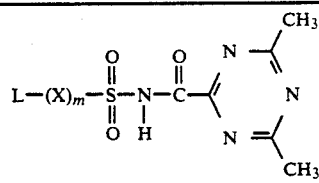

| Example No. | L | X | m | Melting point [°C.] |
|---|---|---|---|---|
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-1 | CH$_2$ | 1 | |
| 56 | L1-2 | CH$_2$ | 1 | |
| 57 | L1-3 | CH$_2$ | 1 | |
| 58 | L1-4 | CH$_2$ | 1 | |
| 59 | L1-5 | CH$_2$ | 1 | |
| 60 | L1-6 | CH$_2$ | 1 | |
| 61 | L1-7 | CH$_2$ | 1 | |
| 62 | L1-8 | CH$_2$ | 1 | |
| 63 | L1-9 | CH$_2$ | 1 | |
| 64 | L1-10 | CH$_2$ | 1 | |
| 65 | L1-11 | CH$_2$ | 1 | |
| 66 | L1-12 | CH$_2$ | 1 | |
| 67 | L1-13 | CH$_2$ | 1 | |
| 68 | L1-14 | CH$_2$ | 1 | |
| 69 | L1-15 | CH$_2$ | 1 | |
| 70 | L1-16 | CH$_2$ | 1 | |
| 71 | L1-17 | CH$_2$ | 1 | |
| 72 | L1-18 | CH$_2$ | 1 | |
| 73 | L1-19 | CH$_2$ | 1 | |
| 74 | L1-20 | CH$_2$ | 1 | |
| 75 | L1-21 | CH$_2$ | 1 | |
| 76 | L1-22 | CH$_2$ | 1 | |
| 77 | L1-23 | CH$_2$ | 1 | |
| 78 | L1-24 | CH$_2$ | 1 | |
| 79 | L1-25 | CH$_2$ | 1 | |
| 80 | L1-26 | CH$_2$ | 1 | |
| 81 | L1-27 | CH$_2$ | 1 | |
| 82 | L1-28 | CH$_2$ | 1 | |
| 83 | L1-29 | CH$_2$ | 1 | |
| 84 | L1-30 | CH$_2$ | 1 | |
| 85 | L1-31 | CH$_2$ | 1 | |
| 86 | L1-32 | CH$_2$ | 1 | |
| 87 | L1-33 | CH$_2$ | 1 | |
| 88 | L1-34 | CH$_2$ | 1 | |
| 89 | L1-35 | CH$_2$ | 1 | |
| 90 | L1-36 | CH$_2$ | 1 | |
| 91 | L1-37 | CH$_2$ | 1 | |
| 92 | L1-38 | CH$_2$ | 1 | |
| 93 | L1-39 | CH$_2$ | 1 | |
| 94 | L1-40 | CH$_2$ | 1 | |
| 95 | L1-41 | CH$_2$ | 1 | |
| 96 | L1-42 | CH$_2$ | 1 | |
| 97 | L1-43 | CH$_2$ | 1 | |
| 98 | L1-44 | CH$_2$ | 1 | |
| 99 | L1-45 | CH$_2$ | 1 | |
| 100 | L1-46 | CH$_2$ | 1 | |
| 101 | L1-47 | CH$_2$ | 1 | |
| 102 | L1-48 | CH$_2$ | 1 | |
| 103 | L1-49 | CH$_2$ | 1 | |
| 104 | L1-50 | CH$_2$ | 1 | |
| 105 | L1-51 | CH$_2$ | 1 | |
| 106 | L1-52 | CH$_2$ | 1 | |
| 107 | L1-53 | CH$_2$ | 1 | |
| 108 | L1-54 | CH$_2$ | 1 | |
| 109 | L1-1 | O | 1 | |

TABLE 7-continued

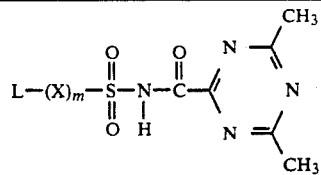

| Example No. | L | X | m | Melting point [°C.] |
|---|---|---|---|---|
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |
| 145 | L1-37 | O | 1 | |
| 146 | L1-38 | O | 1 | |
| 147 | L1-39 | O | 1 | |
| 148 | L1-40 | O | 1 | |
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |

TABLE 7-continued

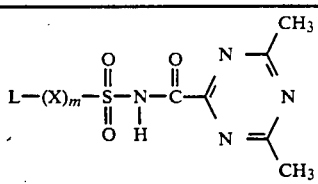

| Example No. | L | X | m | Melting point [°C.] |
|---|---|---|---|---|
| 182 | L1-20 | NH | 1 | |
| 183 | L1-21 | NH | 1 | |
| 184 | L1-22 | NH | 1 | |
| 185 | L1-23 | NH | 1 | |
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | |
| 219 | L3-3 | — | 0 | |
| 220 | L3-4 | — | 0 | |
| 221 | L3-5 | — | 0 | |
| 222 | L3-1 | CH$_2$ | 1 | |
| 223 | L3-2 | CH$_2$ | 1 | |
| 224 | L3-3 | CH$_2$ | 1 | |
| 225 | L3-4 | CH$_2$ | 1 | |
| 226 | L3-5 | CH$_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | |
| 239 | L4-3 | — | 0 | |
| 240 | L4-4 | — | 0 | |
| 241 | L4-5 | — | 0 | |
| 242 | L4-1 | CH$_2$ | 1 | |
| 243 | L4-2 | CH$_2$ | 1 | |
| 244 | L4-3 | CH$_2$ | 1 | |
| 245 | L4-4 | CH$_2$ | 1 | |
| 246 | L4-5 | CH$_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |

TABLE 7-continued

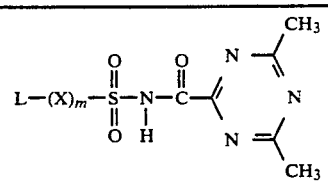

| Example No. | L | X | m | Melting point [°C.] |
|---|---|---|---|---|
| 254 | L4-3 | NH | 1 | |
| 255 | L4-4 | NH | 1 | |
| 256 | L4-5 | NH | 1 | |
| 257 | L5-1 | — | 0 | |
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | CH$_2$ | 1 | |
| 268 | L5-2 | CH$_2$ | 1 | |
| 269 | L5-3 | CH$_2$ | 1 | |
| 270 | L5-4 | CH$_2$ | 1 | |
| 271 | L5-5 | CH$_2$ | 1 | |
| 272 | L5-6 | CH$_2$ | 1 | |
| 273 | L5-7 | CH$_2$ | 1 | |
| 274 | L5-8 | CH$_2$ | 1 | |
| 275 | L5-9 | CH$_2$ | 1 | |
| 276 | L5-10 | CH$_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |
| 291 | L5-5 | NH | 1 | |
| 292 | L5-6 | NH | 1 | |
| 293 | L5-7 | NH | 1 | |
| 294 | L5-8 | NH | 1 | |
| 295 | L5-9 | NH | 1 | |
| 296 | L5-10 | NH | 1 | |
| 297 | L1-55 | CH$_2$ | 1 | |
| 298 | L1-56 | CH$_2$ | 1 | |
| 299 | L1-57 | CH$_2$ | 1 | |
| 300 | L1-58 | CH$_2$ | 1 | |
| 301 | L1-59 | CH$_2$ | 1 | |
| 302 | L1-60 | CH$_2$ | 1 | |
| 303 | L1-61 | CH$_2$ | 1 | |
| 304 | L1-62 | CH$_2$ | 1 | |
| 305 | L1-63 | CH$_2$ | 1 | |
| 306 | L1-64 | CH$_2$ | 1 | |
| 307 | L1-65 | CH$_2$ | 1 | |
| 308 | L1-66 | CH$_2$ | 1 | |
| 309 | L1-67 | CH$_2$ | 1 | |
| 310 | L1-68 | CH$_2$ | 1 | |

TABLE 8

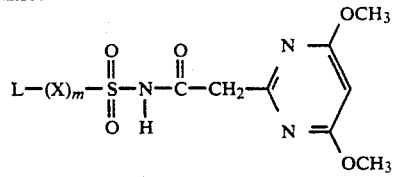

| Example No. | L | X | m | Melting point [°C.] |
|---|---|---|---|---|
| 1 | L1-1 | — | 0 | |
| 2 | L1-2 | — | 0 | 113–115 |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | 97–100 |
| 27 | L1-27 | — | 0 | |
| 28 | L1-28 | — | 0 | 125–129 |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | 84–87 |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-1 | $CH_2$ | 1 | 98–101 |
| 56 | L1-2 | $CH_2$ | 1 | |
| 57 | L1-3 | $CH_2$ | 1 | |
| 58 | L1-4 | $CH_2$ | 1 | |
| 59 | L1-5 | $CH_2$ | 1 | |
| 60 | L1-6 | $CH_2$ | 1 | |
| 61 | L1-7 | $CH_2$ | 1 | |
| 62 | L1-8 | $CH_2$ | 1 | |
| 63 | L1-9 | $CH_2$ | 1 | |
| 64 | L1-10 | $CH_2$ | 1 | |
| 65 | L1-11 | $CH_2$ | 1 | |
| 66 | L1-12 | $CH_2$ | 1 | |
| 67 | L1-13 | $CH_2$ | 1 | |
| 68 | L1-14 | $CH_2$ | 1 | |
| 69 | L1-15 | $CH_2$ | 1 | |
| 70 | L1-16 | $CH_2$ | 1 | |
| 71 | L1-17 | $CH_2$ | 1 | |
| 72 | L1-18 | $CH_2$ | 1 | |

TABLE 8-continued

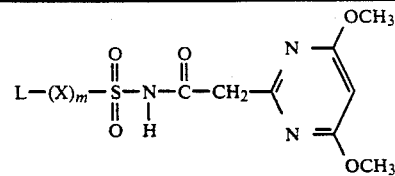

| Example No. | L | X | m | Melting point [°C.] |
|---|---|---|---|---|
| 73 | L1-19 | $CH_2$ | 1 | |
| 74 | L1-20 | $CH_2$ | 1 | |
| 75 | L1-21 | $CH_2$ | 1 | |
| 76 | L1-22 | $CH_2$ | 1 | |
| 77 | L1-23 | $CH_2$ | 1 | |
| 78 | L1-24 | $CH_2$ | 1 | |
| 79 | L1-25 | $CH_2$ | 1 | |
| 80 | L1-26 | $CH_2$ | 1 | |
| 81 | L1-27 | $CH_2$ | 1 | |
| 82 | L1-28 | $CH_2$ | 1 | |
| 83 | L1-29 | $CH_2$ | 1 | |
| 84 | L1-30 | $CH_2$ | 1 | |
| 85 | L1-31 | $CH_2$ | 1 | |
| 86 | L1-32 | $CH_2$ | 1 | |
| 87 | L1-33 | $CH_2$ | 1 | |
| 88 | L1-34 | $CH_2$ | 1 | |
| 89 | L1-35 | $CH_2$ | 1 | |
| 90 | L1-36 | $CH_2$ | 1 | |
| 91 | L1-37 | $CH_2$ | 1 | |
| 92 | L1-38 | $CH_2$ | 1 | |
| 93 | L1-39 | $CH_2$ | 1 | |
| 94 | L1-40 | $CH_2$ | 1 | |
| 95 | L1-41 | $CH_2$ | 1 | |
| 96 | L1-42 | $CH_2$ | 1 | |
| 97 | L1-43 | $CH_2$ | 1 | |
| 98 | L1-44 | $CH_2$ | 1 | |
| 99 | L1-45 | $CH_2$ | 1 | |
| 100 | L1-46 | $CH_2$ | 1 | |
| 101 | L1-47 | $CH_2$ | 1 | |
| 102 | L1-48 | $CH_2$ | 1 | |
| 103 | L1-49 | $CH_2$ | 1 | |
| 104 | L1-50 | $CH_2$ | 1 | |
| 105 | L1-51 | $CH_2$ | 1 | |
| 106 | L1-52 | $CH_2$ | 1 | |
| 107 | L1-53 | $CH_2$ | 1 | |
| 108 | L1-54 | $CH_2$ | 1 | |
| 109 | L1-1 | O | 1 | |
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | 100–102 |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |

TABLE 8-continued

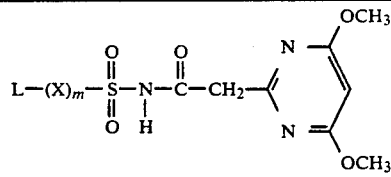

| Example No. | L | X | m | Melting point [°C.] |
|---|---|---|---|---|
| 145 | L1-37 | O | 1 | |
| 146 | L1-38 | O | 1 | |
| 147 | L1-39 | O | 1 | |
| 148 | L1-40 | O | 1 | |
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |
| 184 | L1-22 | NH | 1 | |
| 185 | L1-23 | NH | 1 | |
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |

TABLE 8-continued

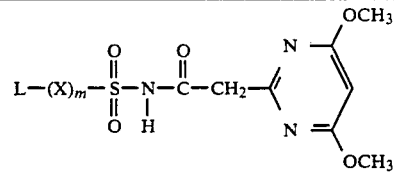

| Example No. | L | X | m | Melting point [°C.] |
|---|---|---|---|---|
| 217 | L3-1 | — | 0 | |
| 218 | L3-2 | — | 0 | |
| 219 | L3-3 | — | 0 | |
| 220 | L3-4 | — | 0 | |
| 221 | L3-5 | — | 0 | 97–99 |
| 222 | L3-1 | CH$_2$ | 1 | |
| 223 | L3-2 | CH$_2$ | 1 | |
| 224 | L3-3 | CH$_2$ | 1 | |
| 225 | L3-4 | CH$_2$ | 1 | |
| 226 | L3-5 | CH$_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | 101–104 |
| 239 | L4-3 | — | 0 | |
| 240 | L4-4 | — | 0 | |
| 241 | L4-5 | — | 0 | |
| 242 | L4-1 | CH$_2$ | 1 | |
| 243 | L4-2 | CH$_2$ | 1 | |
| 244 | L4-3 | CH$_2$ | 1 | |
| 245 | L4-4 | CH$_2$ | 1 | |
| 246 | L4-5 | CH$_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |
| 256 | L4-5 | NH | 1 | |
| 257 | L5-1 | — | 0 | |
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | CH$_2$ | 1 | |
| 268 | L5-2 | CH$_2$ | 1 | |
| 269 | L5-3 | CH$_2$ | 1 | |
| 270 | L5-4 | CH$_2$ | 1 | |
| 271 | L5-5 | CH$_2$ | 1 | |
| 272 | L5-6 | CH$_2$ | 1 | |
| 273 | L5-7 | CH$_2$ | 1 | |
| 274 | L5-8 | CH$_2$ | 1 | |
| 275 | L5-9 | CH$_2$ | 1 | |
| 276 | L5-10 | CH$_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |

TABLE 8-continued

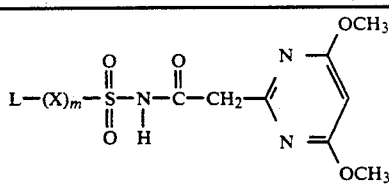

| Example No. | L | X | m | Melting point [°C.] |
|---|---|---|---|---|
| 289 | L5-3 | NH | 1 | |
| 290 | L5-4 | NH | 1 | |
| 291 | L5-5 | NH | 1 | |
| 292 | L5-6 | NH | 1 | |
| 293 | L5-7 | NH | 1 | |
| 294 | L5-8 | NH | 1 | |
| 295 | L5-9 | NH | 1 | |
| 296 | L5-10 | NH | 1 | |

TABLE 9

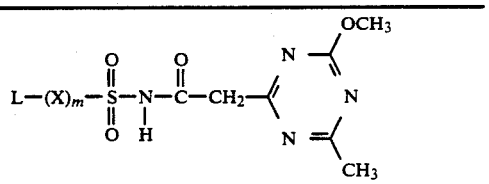

| Example No. | L | X | m | Melting point [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |

TABLE 9-continued

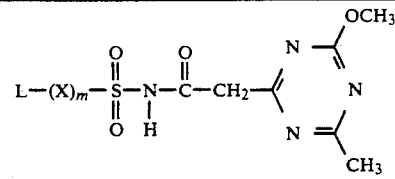

| Example No. | L | X | m | Melting point [°C.] |
|---|---|---|---|---|
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-1 | $CH_2$ | 1 | |
| 56 | L1-2 | $CH_2$ | 1 | |
| 57 | L1-3 | $CH_2$ | 1 | |
| 58 | L1-4 | $CH_2$ | 1 | |
| 59 | L1-5 | $CH_2$ | 1 | |
| 60 | L1-6 | $CH_2$ | 1 | |
| 61 | L1-7 | $CH_2$ | 1 | |
| 62 | L1-8 | $CH_2$ | 1 | |
| 63 | L1-9 | $CH_2$ | 1 | |
| 64 | L1-10 | $CH_2$ | 1 | |
| 65 | L1-11 | $CH_2$ | 1 | |
| 66 | L1-12 | $CH_2$ | 1 | |
| 67 | L1-13 | $CH_2$ | 1 | |
| 68 | L1-14 | $CH_2$ | 1 | |
| 69 | L1-15 | $CH_2$ | 1 | |
| 70 | L1-16 | $CH_2$ | 1 | |
| 71 | L1-17 | $CH_2$ | 1 | |
| 72 | L1-18 | $CH_2$ | 1 | |
| 73 | L1-19 | $CH_2$ | 1 | |
| 74 | L1-20 | $CH_2$ | 1 | |
| 75 | L1-21 | $CH_2$ | 1 | |
| 76 | L1-22 | $CH_2$ | 1 | |
| 77 | L1-23 | $CH_2$ | 1 | |
| 78 | L1-24 | $CH_2$ | 1 | |
| 79 | L1-25 | $CH_2$ | 1 | |
| 80 | L1-26 | $CH_2$ | 1 | |
| 81 | L1-27 | $CH_2$ | 1 | |
| 82 | L1-28 | $CH_2$ | 1 | |
| 83 | L1-29 | $CH_2$ | 1 | |
| 84 | L1-30 | $CH_2$ | 1 | |
| 85 | L1-31 | $CH_2$ | 1 | |
| 86 | L1-32 | $CH_2$ | 1 | |
| 87 | L1-33 | $CH_2$ | 1 | |
| 88 | L1-34 | $CH_2$ | 1 | |
| 89 | L1-35 | $CH_2$ | 1 | |
| 90 | L1-36 | $CH_2$ | 1 | |
| 91 | L1-37 | $CH_2$ | 1 | |
| 92 | L1-38 | $CH_2$ | 1 | |
| 93 | L1-39 | $CH_2$ | 1 | |
| 94 | L1-40 | $CH_2$ | 1 | |
| 95 | L1-41 | $CH_2$ | 1 | |
| 96 | L1-42 | $CH_2$ | 1 | |
| 97 | L1-43 | $CH_2$ | 1 | |
| 98 | L1-44 | $CH_2$ | 1 | |
| 99 | L1-45 | $CH_2$ | 1 | |
| 100 | L1-46 | $CH_2$ | 1 | |
| 101 | L1-47 | $CH_2$ | 1 | |
| 102 | L1-48 | $CH_2$ | 1 | |
| 103 | L1-49 | $CH_2$ | 1 | |
| 104 | L1-50 | $CH_2$ | 1 | |
| 105 | L1-51 | $CH_2$ | 1 | |
| 106 | L1-52 | $CH_2$ | 1 | |
| 107 | L1-53 | $CH_2$ | 1 | |
| 108 | L1-54 | $CH_2$ | 1 | |
| 109 | L1-1 | O | 1 | |
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |

TABLE 9-continued

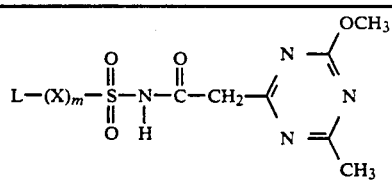

| Example No. | L | X | m | Melting point [°C.] |
|---|---|---|---|---|
| 122 | L1-14 | O | 1 | |
| 123 | L1-15 | O | 1 | |
| 124 | L1-16 | O | 1 | |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |
| 145 | L1-37 | O | 1 | |
| 146 | L1-38 | O | 1 | |
| 147 | L1-39 | O | 1 | |
| 148 | L1-40 | O | 1 | |
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |
| 184 | L1-22 | NH | 1 | |
| 185 | L1-23 | NH | 1 | |
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |

TABLE 9-continued

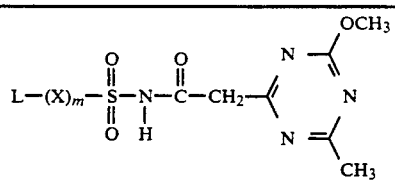

| Example No. | L | X | m | Melting point [°C.] |
|---|---|---|---|---|
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | |
| 219 | L3-3 | — | 0 | |
| 220 | L3-4 | — | 0 | |
| 221 | L3-5 | — | 0 | |
| 222 | L3-1 | CH$_2$ | 1 | |
| 223 | L3-2 | CH$_2$ | 1 | |
| 224 | L3-3 | CH$_2$ | 1 | |
| 225 | L3-4 | CH$_2$ | 1 | |
| 226 | L3-5 | CH$_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | |
| 239 | L4-3 | — | 0 | |
| 240 | L4-4 | — | 0 | |
| 241 | L4-5 | — | 0 | |
| 242 | L4-1 | CH$_2$ | 1 | |
| 243 | L4-2 | CH$_2$ | 1 | |
| 244 | L4-3 | CH$_2$ | 1 | |
| 245 | L4-4 | CH$_2$ | 1 | |
| 246 | L4-5 | CH$_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |
| 256 | L4-5 | NH | 1 | |
| 257 | L5-1 | — | 0 | |
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |

TABLE 9-continued

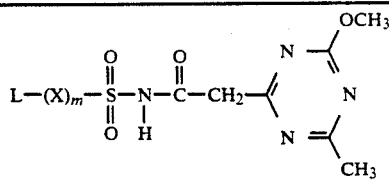

| Example No. | L | X | m | Melting point [°C.] |
|---|---|---|---|---|
| 266 | L5-10 | — | 0 | |
| 267 | L5-1 | CH$_2$ | 1 | |
| 268 | L5-2 | CH$_2$ | 1 | |
| 269 | L5-3 | CH$_2$ | 1 | |
| 270 | L5-4 | CH$_2$ | 1 | |
| 271 | L5-5 | CH$_2$ | 1 | |
| 272 | L5-6 | CH$_2$ | 1 | |
| 273 | L5-7 | CH$_2$ | 1 | |
| 274 | L5-8 | CH$_2$ | 1 | |
| 275 | L5-9 | CH$_2$ | 1 | |
| 276 | L5-10 | CH$_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |
| 291 | L5-5 | NH | 1 | |
| 292 | L5-6 | NH | 1 | |
| 293 | L5-7 | NH | 1 | |
| 294 | L5-8 | NH | 1 | |
| 295 | L5-9 | NH | 1 | |
| 296 | L5-10 | NH | 1 | |

TABLE 10

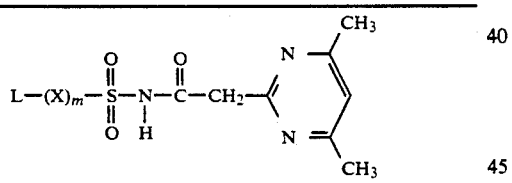

| Example No. | L | X | m | Melting point [°C.] |
|---|---|---|---|---|
| 1 | L1-1 | — | 0 | |
| 2 | L1-2 | — | 0 | |
| 3 | L1-3 | — | 0 | |
| 4 | L1-4 | — | 0 | |
| 5 | L1-5 | — | 0 | |
| 6 | L1-6 | — | 0 | |
| 7 | L1-7 | — | 0 | |
| 8 | L1-8 | — | 0 | |
| 9 | L1-9 | — | 0 | |
| 10 | L1-10 | — | 0 | |
| 11 | L1-11 | — | 0 | |
| 12 | L1-12 | — | 0 | |
| 13 | L1-13 | — | 0 | |
| 14 | L1-14 | — | 0 | |
| 15 | L1-15 | — | 0 | |
| 16 | L1-16 | — | 0 | |
| 17 | L1-17 | — | 0 | |
| 18 | L1-18 | — | 0 | |
| 19 | L1-19 | — | 0 | |
| 20 | L1-20 | — | 0 | |
| 21 | L1-21 | — | 0 | |
| 22 | L1-22 | — | 0 | |
| 23 | L1-23 | — | 0 | |
| 24 | L1-24 | — | 0 | |
| 25 | L1-25 | — | 0 | |
| 26 | L1-26 | — | 0 | |

TABLE 10-continued

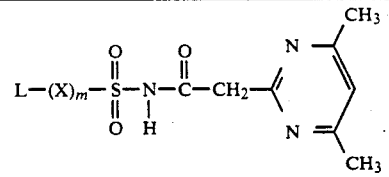

| Example No. | L | X | m | Melting point [°C.] |
|---|---|---|---|---|
| 27 | L1-27 | — | 0 | |
| 28 | L1-28 | — | 0 | |
| 29 | L1-29 | — | 0 | |
| 30 | L1-30 | — | 0 | |
| 31 | L1-31 | — | 0 | |
| 32 | L1-32 | — | 0 | |
| 33 | L1-33 | — | 0 | |
| 34 | L1-34 | — | 0 | |
| 35 | L1-35 | — | 0 | |
| 36 | L1-36 | — | 0 | |
| 37 | L1-37 | — | 0 | |
| 38 | L1-38 | — | 0 | |
| 39 | L1-39 | — | 0 | |
| 40 | L1-40 | — | 0 | |
| 41 | L1-41 | — | 0 | |
| 42 | L1-42 | — | 0 | |
| 43 | L1-43 | — | 0 | |
| 44 | L1-44 | — | 0 | |
| 45 | L1-45 | — | 0 | |
| 46 | L1-46 | — | 0 | |
| 47 | L1-47 | — | 0 | |
| 48 | L1-48 | — | 0 | |
| 49 | L1-49 | — | 0 | |
| 50 | L1-50 | — | 0 | |
| 51 | L1-51 | — | 0 | |
| 52 | L1-52 | — | 0 | |
| 53 | L1-53 | — | 0 | |
| 54 | L1-54 | — | 0 | |
| 55 | L1-1 | CH$_2$ | 1 | |
| 56 | L1-2 | CH$_2$ | 1 | |
| 57 | L1-3 | CH$_2$ | 1 | |
| 58 | L1-4 | CH$_2$ | 1 | |
| 59 | L1-5 | CH$_2$ | 1 | |
| 60 | L1-6 | CH$_2$ | 1 | |
| 61 | L1-7 | CH$_2$ | 1 | |
| 62 | L1-8 | CH$_2$ | 1 | |
| 63 | L1-9 | CH$_2$ | 1 | |
| 64 | L1-10 | CH$_2$ | 1 | |
| 65 | L1-11 | CH$_2$ | 1 | |
| 66 | L1-12 | CH$_2$ | 1 | |
| 67 | L1-13 | CH$_2$ | 1 | |
| 68 | L1-14 | CH$_2$ | 1 | |
| 69 | L1-15 | CH$_2$ | 1 | |
| 70 | L1-16 | CH$_2$ | 1 | |
| 71 | L1-17 | CH$_2$ | 1 | |
| 72 | L1-18 | CH$_2$ | 1 | |
| 73 | L1-19 | CH$_2$ | 1 | |
| 74 | L1-20 | CH$_2$ | 1 | |
| 75 | L1-21 | CH$_2$ | 1 | |
| 76 | L1-22 | CH$_2$ | 1 | |
| 77 | L1-23 | CH$_2$ | 1 | |
| 78 | L1-24 | CH$_2$ | 1 | |
| 79 | L1-25 | CH$_2$ | 1 | |
| 80 | L1-26 | CH$_2$ | 1 | |
| 81 | L1-27 | CH$_2$ | 1 | |
| 82 | L1-28 | CH$_2$ | 1 | |
| 83 | L1-29 | CH$_2$ | 1 | |
| 84 | L1-30 | CH$_2$ | 1 | |
| 85 | L1-31 | CH$_2$ | 1 | |
| 86 | L1-32 | CH$_2$ | 1 | |
| 87 | L1-33 | CH$_2$ | 1 | |
| 88 | L1-34 | CH$_2$ | 1 | |
| 89 | L1-35 | CH$_2$ | 1 | |
| 90 | L1-36 | CH$_2$ | 1 | |
| 91 | L1-37 | CH$_2$ | 1 | |
| 92 | L1-38 | CH$_2$ | 1 | |
| 93 | L1-39 | CH$_2$ | 1 | |
| 94 | L1-40 | CH$_2$ | 1 | |
| 95 | L1-41 | CH$_2$ | 1 | |
| 96 | L1-42 | CH$_2$ | 1 | |
| 97 | L1-43 | CH$_2$ | 1 | |
| 98 | L1-44 | CH$_2$ | 1 | |

TABLE 10-continued

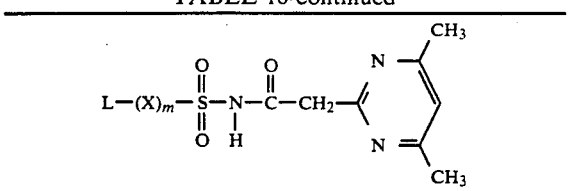

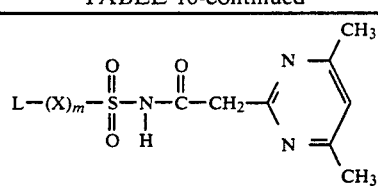

| Example No. | L | X | m | Melting point [°C.] |
|---|---|---|---|---|
| 99 | L1-45 | CH$_2$ | 1 | |
| 100 | L1-46 | CH$_2$ | 1 | |
| 101 | L1-47 | CH$_2$ | 1 | |
| 102 | L1-48 | CH$_2$ | 1 | |
| 103 | L1-49 | CH$_2$ | 1 | |
| 104 | L1-50 | CH$_2$ | 1 | |
| 105 | L1-51 | CH$_2$ | 1 | |
| 106 | L1-52 | CH$_2$ | 1 | |
| 107 | L1-53 | CH$_2$ | 1 | |
| 108 | L1-54 | CH$_2$ | 1 | |
| 109 | L1-1 | O | 1 | |
| 110 | L1-2 | O | 1 | |
| 111 | L1-3 | O | 1 | |
| 112 | L1-4 | O | 1 | |
| 113 | L1-5 | O | 1 | |
| 114 | L1-6 | O | 1 | |
| 115 | L1-7 | O | 1 | |
| 116 | L1-8 | O | 1 | |
| 117 | L1-9 | O | 1 | |
| 118 | L1-10 | O | 1 | |
| 119 | L1-11 | O | 1 | |
| 120 | L1-12 | O | 1 | |
| 121 | L1-13 | O | 1 | |
| 122 | L1-14 | O | 1 | |
| 123 | L1-15 | O | 1 | |
| 124 | L1-16 | O | 1 | |
| 125 | L1-17 | O | 1 | |
| 126 | L1-18 | O | 1 | |
| 127 | L1-19 | O | 1 | |
| 128 | L1-20 | O | 1 | |
| 129 | L1-21 | O | 1 | |
| 130 | L1-22 | O | 1 | |
| 131 | L1-23 | O | 1 | |
| 132 | L1-24 | O | 1 | |
| 133 | L1-25 | O | 1 | |
| 134 | L1-26 | O | 1 | |
| 135 | L1-27 | O | 1 | |
| 136 | L1-28 | O | 1 | |
| 137 | L1-29 | O | 1 | |
| 138 | L1-30 | O | 1 | |
| 139 | L1-31 | O | 1 | |
| 140 | L1-32 | O | 1 | |
| 141 | L1-33 | O | 1 | |
| 142 | L1-34 | O | 1 | |
| 143 | L1-35 | O | 1 | |
| 144 | L1-36 | O | 1 | |
| 145 | L1-37 | O | 1 | |
| 146 | L1-38 | O | 1 | |
| 147 | L1-39 | O | 1 | |
| 148 | L1-40 | O | 1 | |
| 149 | L1-41 | O | 1 | |
| 150 | L1-42 | O | 1 | |
| 151 | L1-43 | O | 1 | |
| 152 | L1-44 | O | 1 | |
| 153 | L1-45 | O | 1 | |
| 154 | L1-46 | O | 1 | |
| 155 | L1-47 | O | 1 | |
| 156 | L1-48 | O | 1 | |
| 157 | L1-49 | O | 1 | |
| 158 | L1-50 | O | 1 | |
| 159 | L1-51 | O | 1 | |
| 160 | L1-52 | O | 1 | |
| 161 | L1-53 | O | 1 | |
| 162 | L1-54 | O | 1 | |
| 163 | L1-1 | NH | 1 | |
| 164 | L1-2 | NH | 1 | |
| 165 | L1-3 | NH | 1 | |
| 166 | L1-4 | NH | 1 | |
| 167 | L1-5 | NH | 1 | |
| 168 | L1-6 | NH | 1 | |
| 169 | L1-7 | NH | 1 | |
| 170 | L1-8 | NH | 1 | |
| 171 | L1-9 | NH | 1 | |
| 172 | L1-10 | NH | 1 | |
| 173 | L1-11 | NH | 1 | |
| 174 | L1-12 | NH | 1 | |
| 175 | L1-13 | NH | 1 | |
| 176 | L1-14 | NH | 1 | |
| 177 | L1-15 | NH | 1 | |
| 178 | L1-16 | NH | 1 | |
| 179 | L1-17 | NH | 1 | |
| 180 | L1-18 | NH | 1 | |
| 181 | L1-19 | NH | 1 | |
| 182 | L1-20 | NH | 1 | |
| 183 | L1-21 | NH | 1 | |
| 184 | L1-22 | NH | 1 | |
| 185 | L1-23 | NH | 1 | |
| 186 | L1-24 | NH | 1 | |
| 187 | L1-25 | NH | 1 | |
| 188 | L1-26 | NH | 1 | |
| 189 | L1-27 | NH | 1 | |
| 190 | L1-28 | NH | 1 | |
| 191 | L1-29 | NH | 1 | |
| 192 | L1-30 | NH | 1 | |
| 193 | L1-31 | NH | 1 | |
| 194 | L1-32 | NH | 1 | |
| 195 | L1-33 | NH | 1 | |
| 196 | L1-34 | NH | 1 | |
| 197 | L1-35 | NH | 1 | |
| 198 | L1-36 | NH | 1 | |
| 199 | L1-37 | NH | 1 | |
| 200 | L1-38 | NH | 1 | |
| 201 | L1-39 | NH | 1 | |
| 202 | L1-40 | NH | 1 | |
| 203 | L1-41 | NH | 1 | |
| 204 | L1-42 | NH | 1 | |
| 205 | L1-43 | NH | 1 | |
| 206 | L1-44 | NH | 1 | |
| 207 | L1-45 | NH | 1 | |
| 208 | L1-46 | NH | 1 | |
| 209 | L1-47 | NH | 1 | |
| 210 | L1-48 | NH | 1 | |
| 211 | L1-49 | NH | 1 | |
| 212 | L1-50 | NH | 1 | |
| 213 | L1-51 | NH | 1 | |
| 214 | L1-52 | NH | 1 | |
| 215 | L1-53 | NH | 1 | |
| 216 | L1-54 | NH | 1 | |
| 217 | L3-1 | — | 0 | |
| 218 | L3-2 | — | 0 | |
| 219 | L3-3 | — | 0 | |
| 220 | L3-4 | — | 0 | |
| 221 | L3-5 | — | 0 | |
| 222 | L3-1 | CH$_2$ | 1 | |
| 223 | L3-2 | CH$_2$ | 1 | |
| 224 | L3-3 | CH$_2$ | 1 | |
| 225 | L3-4 | CH$_2$ | 1 | |
| 226 | L3-5 | CH$_2$ | 1 | |
| 227 | L3-1 | O | 1 | |
| 228 | L3-2 | O | 1 | |
| 229 | L3-3 | O | 1 | |
| 230 | L3-4 | O | 1 | |
| 231 | L3-5 | O | 1 | |
| 232 | L3-1 | NH | 1 | |
| 233 | L3-2 | NH | 1 | |
| 234 | L3-3 | NH | 1 | |
| 235 | L3-4 | NH | 1 | |
| 236 | L3-5 | NH | 1 | |
| 237 | L4-1 | — | 0 | |
| 238 | L4-2 | — | 0 | |
| 239 | L4-3 | — | 0 | |
| 240 | L4-4 | — | 0 | |
| 241 | L4-5 | — | 0 | |
| 242 | L4-1 | CH$_2$ | 1 | |

TABLE 10-continued

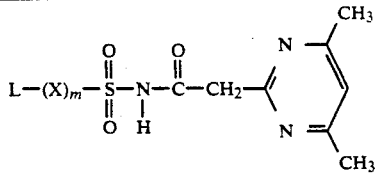

| Example No. | L | X | m | Melting point [°C.] |
|---|---|---|---|---|
| 243 | L4-2 | CH$_2$ | 1 | |
| 244 | L4-3 | CH$_2$ | 1 | |
| 245 | L4-4 | CH$_2$ | 1 | |
| 246 | L4-5 | CH$_2$ | 1 | |
| 247 | L4-1 | O | 1 | |
| 248 | L4-2 | O | 1 | |
| 249 | L4-3 | O | 1 | |
| 250 | L4-4 | O | 1 | |
| 251 | L4-5 | O | 1 | |
| 252 | L4-1 | NH | 1 | |
| 253 | L4-2 | NH | 1 | |
| 254 | L4-3 | NH | 1 | |
| 255 | L4-4 | NH | 1 | |
| 256 | L4-5 | NH | 1 | |
| 257 | L5-1 | — | 0 | |
| 258 | L5-2 | — | 0 | |
| 259 | L5-3 | — | 0 | |
| 260 | L5-4 | — | 0 | |
| 261 | L5-5 | — | 0 | |
| 262 | L5-6 | — | 0 | |
| 263 | L5-7 | — | 0 | |
| 264 | L5-8 | — | 0 | |
| 265 | L5-9 | — | 0 | |
| 266 | L5-10 | — | 0 | |
| 267 | L5-1 | CH$_2$ | 1 | |
| 268 | L5-2 | CH$_2$ | 1 | |
| 269 | L5-3 | CH$_2$ | 1 | |
| 270 | L5-4 | CH$_2$ | 1 | |
| 271 | L5-5 | CH$_2$ | 1 | |
| 272 | L5-6 | CH$_2$ | 1 | |
| 273 | L5-7 | CH$_2$ | 1 | |
| 274 | L5-8 | CH$_2$ | 1 | |
| 275 | L5-9 | CH$_2$ | 1 | |
| 276 | L5-10 | CH$_2$ | 1 | |
| 277 | L5-1 | O | 1 | |
| 278 | L5-2 | O | 1 | |
| 279 | L5-3 | O | 1 | |
| 280 | L5-4 | O | 1 | |
| 281 | L5-5 | O | 1 | |
| 282 | L5-6 | O | 1 | |
| 283 | L5-7 | O | 1 | |
| 284 | L5-8 | O | 1 | |
| 285 | L5-9 | O | 1 | |
| 286 | L5-10 | O | 1 | |
| 287 | L5-1 | NH | 1 | |
| 288 | L5-2 | NH | 1 | |
| 289 | L5-3 | NH | 1 | |
| 290 | L5-4 | NH | 1 | |
| 291 | L5-5 | NH | 1 | |
| 292 | L5-6 | NH | 1 | |
| 293 | L5-7 | NH | 1 | |
| 294 | L5-8 | NH | 1 | |
| 295 | L5-9 | NH | 1 | |
| 296 | L5-10 | NH | 1 | |

TABLE 11

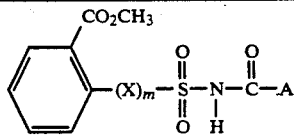

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | CH$_2$ | 1 | A1-5 | |
| 54 | CH$_2$ | 1 | A1-6 | |
| 55 | CH$_2$ | 1 | A1-7 | |
| 56 | CH$_2$ | 1 | A1-8 | |
| 57 | CH$_2$ | 1 | A1-9 | |
| 58 | CH$_2$ | 1 | A1-10 | |
| 59 | CH$_2$ | 1 | A1-11 | |
| 60 | CH$_2$ | 1 | A1-12 | |
| 61 | CH$_2$ | 1 | A1-13 | |
| 62 | CH$_2$ | 1 | A1-14 | |
| 63 | CH$_2$ | 1 | A1-15 | |
| 64 | CH$_2$ | 1 | A1-16 | |
| 65 | CH$_2$ | 1 | A1-17 | |
| 66 | CH$_2$ | 1 | A1-21 | |
| 67 | CH$_2$ | 1 | A1-22 | |
| 68 | CH$_2$ | 1 | A1-23 | |
| 69 | CH$_2$ | 1 | A1-24 | |
| 70 | CH$_2$ | 1 | A1-25 | |
| 71 | CH$_2$ | 1 | A2-1 | |
| 72 | CH$_2$ | 1 | A2-2 | |
| 73 | CH$_2$ | 1 | A2-3 | |
| 74 | CH$_2$ | 1 | A2-4 | |
| 75 | CH$_2$ | 1 | A3-1 | |
| 76 | CH$_2$ | 1 | A3-2 | |
| 77 | CH$_2$ | 1 | A3-3 | |
| 78 | CH$_2$ | 1 | A3-4 | |

TABLE 11-continued

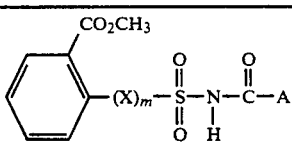

| Ex. No. | X | m | A | M.p. [°C.] |
|---|---|---|---|---|
| 79 | CH$_2$ | 1 | A4-1 | |
| 80 | CH$_2$ | 1 | A4-2 | |
| 81 | CH$_2$ | 1 | A4-3 | |
| 82 | CH$_2$ | 1 | A4-4 | |
| 83 | CH$_2$ | 1 | A5-1 | |
| 84 | CH$_2$ | 1 | A5-2 | |
| 85 | CH$_2$ | 1 | A5-3 | |
| 86 | CH$_2$ | 1 | A5-4 | |
| 87 | CH$_2$ | 1 | A6-1 | |
| 88 | CH$_2$ | 1 | A6-2 | |
| 89 | CH$_2$ | 1 | A7-1 | |
| 90 | CH$_2$ | 1 | A7-2 | |
| 91 | CH$_2$ | 1 | A7-3 | |
| 92 | CH$_2$ | 1 | A7-4 | |
| 93 | CH$_2$ | 1 | A7-5 | |
| 94 | CH$_2$ | 1 | A8-2 | |
| 95 | CH$_2$ | 1 | A8-3 | |
| 96 | CH$_2$ | 1 | A8-4 | |
| 97 | CH$_2$ | 1 | A8-5 | |
| 98 | CH$_2$ | 1 | A8-6 | |
| 99 | CH$_2$ | 1 | A8-7 | |
| 100 | CH$_2$ | 1 | A8-9 | |
| 101 | CH$_2$ | 1 | A8-10 | |
| 102 | CH$_2$ | 1 | A8-11 | |
| 103 | CH$_2$ | 1 | A8-12 | |
| 104 | CH$_2$ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |
| 147 | O | 1. | A8-3 | |
| 148 | O | 1 | A8-4 | |
| 149 | O | 1 | A8-5 | |
| 150 | O | 1 | A8-6 | |
| 151 | O | 1 | A8-7 | |

TABLE 11-continued

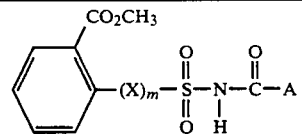

| Ex. No. | X | m | A | M.p. [°C.] |
|---|---|---|---|---|
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 12

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |

TABLE 12-continued

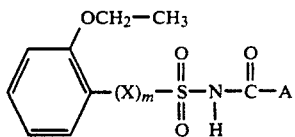

| Ex. No. | X | m | A | M.p. [°C.] |
|---|---|---|---|---|
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |
| 74 | $CH_2$ | 1 | A2-4 | |
| 75 | $CH_2$ | 1 | A3-1 | |
| 76 | $CH_2$ | 1 | A3-2 | |
| 77 | $CH_2$ | 1 | A3-3 | |
| 78 | $CH_2$ | 1 | A3-4 | |
| 79 | $CH_2$ | 1 | A4-1 | |
| 80 | $CH_2$ | 1 | A4-2 | |
| 81 | $CH_2$ | 1 | A4-3 | |
| 82 | $CH_2$ | 1 | A4-4 | |
| 83 | $CH_2$ | 1 | A5-1 | |
| 84 | $CH_2$ | 1 | A5-2 | |
| 85 | $CH_2$ | 1 | A5-3 | |
| 86 | $CH_2$ | 1 | A5-4 | |
| 87 | $CH_2$ | 1 | A6-1 | |
| 88 | $CH_2$ | 1 | A6-2 | |
| 89 | $CH_2$ | 1 | A7-1 | |
| 90 | $CH_2$ | 1 | A7-2 | |
| 91 | $CH_2$ | 1 | A7-3 | |
| 92 | $CH_2$ | 1 | A7-4 | |
| 93 | $CH_2$ | 1 | A7-5 | |
| 94 | $CH_2$ | 1 | A8-2 | |
| 95 | $CH_2$ | 1 | A8-3 | |
| 96 | $CH_2$ | 1 | A8-4 | |
| 97 | $CH_2$ | 1 | A8-5 | |
| 98 | $CH_2$ | 1 | A8-6 | |
| 99 | $CH_2$ | 1 | A8-7 | |
| 100 | $CH_2$ | 1 | A8-9 | |
| 101 | $CH_2$ | 1 | A8-10 | |
| 102 | $CH_2$ | 1 | A8-11 | |
| 103 | $CH_2$ | 1 | A8-12 | |
| 104 | $CH_2$ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |
| 147 | O | 1 | A8-3 | |
| 148 | O | 1 | A8-4 | |
| 149 | O | 1 | A8-5 | |

TABLE 12-continued

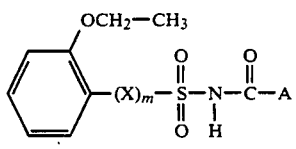

| Ex. No. | X | m | A | M.p. [°C.] |
|---|---|---|---|---|
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 13

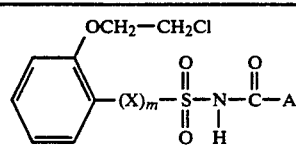

| Ex. No. | X | m | A | M.p. [°C.] |
|---|---|---|---|---|
| 1 | — | 0 | A1-5 | |

TABLE 13-continued

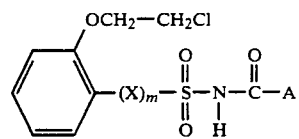

| Ex. No. | X | m | A | M.p. [°C.] |
|---|---|---|---|---|
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |
| 74 | $CH_2$ | 1 | A2-4 | |

TABLE 13-continued

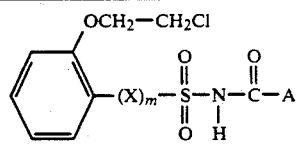

| Ex. No. | X | m | A | M.p. [°C.] |
|---|---|---|---|---|
| 75 | CH₂ | 1 | A3-1 | |
| 76 | CH₂ | 1 | A3-2 | |
| 77 | CH₂ | 1 | A3-3 | |
| 78 | CH₂ | 1 | A3-4 | |
| 79 | CH₂ | 1 | A4-1 | |
| 80 | CH₂ | 1 | A4-2 | |
| 81 | CH₂ | 1 | A4-3 | |
| 82 | CH₂ | 1 | A4-4 | |
| 83 | CH₂ | 1 | A5-1 | |
| 84 | CH₂ | 1 | A5-2 | |
| 85 | CH₂ | 1 | A5-3 | |
| 86 | CH₂ | 1 | A5-4 | |
| 87 | CH₂ | 1 | A6-1 | |
| 88 | CH₂ | 1 | A6-2 | |
| 89 | CH₂ | 1 | A7-1 | |
| 90 | CH₂ | 1 | A7-2 | |
| 91 | CH₂ | 1 | A7-3 | |
| 92 | CH₂ | 1 | A7-4 | |
| 93 | CH₂ | 1 | A7-5 | |
| 94 | CH₂ | 1 | A8-2 | |
| 95 | CH₂ | 1 | A8-3 | |
| 96 | CH₂ | 1 | A8-4 | |
| 97 | CH₂ | 1 | A8-5 | |
| 98 | CH₂ | 1 | A8-6 | |
| 99 | CH₂ | 1 | A8-7 | |
| 100 | CH₂ | 1 | A8-9 | |
| 101 | CH₂ | 1 | A8-10 | |
| 102 | CH₂ | 1 | A8-11 | |
| 103 | CH₂ | 1 | A8-12 | |
| 104 | CH₂ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |
| 147 | O | 1 | A8-3 | |

TABLE 13-continued

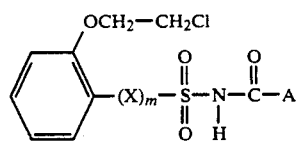

| Ex. No. | X | m | A | M.p. [°C.] |
|---|---|---|---|---|
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 14

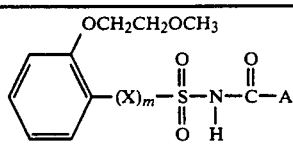

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |
| 74 | $CH_2$ | 1 | A2-4 | |
| 75 | $CH_2$ | 1 | A3-1 | |
| 76 | $CH_2$ | 1 | A3-2 | |
| 77 | $CH_2$ | 1 | A3-3 | |
| 78 | $CH_2$ | 1 | A3-4 | |
| 79 | $CH_2$ | 1 | A4-1 | |
| 80 | $CH_2$ | 1 | A4-2 | |
| 81 | $CH_2$ | 1 | A4-3 | |
| 82 | $CH_2$ | 1 | A4-4 | |
| 83 | $CH_2$ | 1 | A5-1 | |
| 84 | $CH_2$ | 1 | A5-2 | |
| 85 | $CH_2$ | 1 | A5-3 | |
| 86 | $CH_2$ | 1 | A5-4 | |
| 87 | $CH_2$ | 1 | A6-1 | |
| 88 | $CH_2$ | 1 | A6-2 | |
| 89 | $CH_2$ | 1 | A7-1 | |
| 90 | $CH_2$ | 1 | A7-2 | |
| 91 | $CH_2$ | 1 | A7-3 | |
| 92 | $CH_2$ | 1 | A7-4 | |
| 93 | $CH_2$ | 1 | A7-5 | |
| 94 | $CH_2$ | 1 | A8-2 | |
| 95 | $CH_2$ | 1 | A8-3 | |
| 96 | $CH_2$ | 1 | A8-4 | |
| 97 | $CH_2$ | 1 | A8-5 | |
| 98 | $CH_2$ | 1 | A8-6 | |
| 99 | $CH_2$ | 1 | A8-7 | |
| 100 | $CH_2$ | 1 | A8-9 | |
| 101 | $CH_2$ | 1 | A8-10 | |
| 102 | $CH_2$ | 1 | A8-11 | |
| 103 | $CH_2$ | 1 | A8-12 | |
| 104 | $CH_2$ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |

TABLE 14-continued

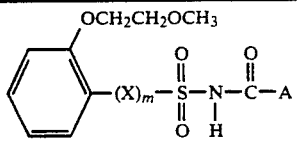

| Ex. No. | X | m | A | M.p. [°C.] |
|---|---|---|---|---|
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 15

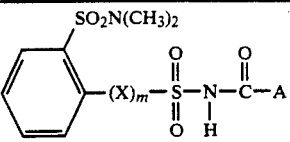

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |

TABLE 15-continued

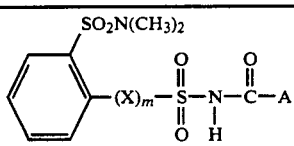

| Ex. No. | X | m | A | M.p. [°C.] |
|---|---|---|---|---|
| 74 | CH$_2$ | 1 | A2-4 | |
| 75 | CH$_2$ | 1 | A3-1 | |
| 76 | CH$_2$ | 1 | A3-2 | |
| 77 | CH$_2$ | 1 | A3-3 | |
| 78 | CH$_2$ | 1 | A3-4 | |
| 79 | CH$_2$ | 1 | A4-1 | |
| 80 | CH$_2$ | 1 | A4-2 | |
| 81 | CH$_2$ | 1 | A4-3 | |
| 82 | CH$_2$ | 1 | A4-4 | |
| 83 | CH$_2$ | 1 | A5-1 | |
| 84 | CH$_2$ | 1 | A5-2 | |
| 85 | CH$_2$ | 1 | A5-3 | |
| 86 | CH$_2$ | 1 | A5-4 | |
| 87 | CH$_2$ | 1 | A6-1 | |
| 88 | CH$_2$ | 1 | A6-2 | |
| 89 | CH$_2$ | 1 | A7-1 | |
| 90 | CH$_2$ | 1 | A7-2 | |
| 91 | CH$_2$ | 1 | A7-3 | |
| 92 | CH$_2$ | 1 | A7-4 | |
| 93 | CH$_2$ | 1 | A7-5 | |
| 94 | CH$_2$ | 1 | A8-2 | |
| 95 | CH$_2$ | 1 | A8-3 | |
| 96 | CH$_2$ | 1 | A8-4 | |
| 97 | CH$_2$ | 1 | A8-5 | |
| 98 | CH$_2$ | 1 | A8-6 | |
| 99 | CH$_2$ | 1 | A8-7 | |
| 100 | CH$_2$ | 1 | A8-9 | |
| 101 | CH$_2$ | 1 | A8-10 | |
| 102 | CH$_2$ | 1 | A8-11 | |
| 103 | CH$_2$ | 1 | A8-12 | |
| 104 | CH$_2$ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 16

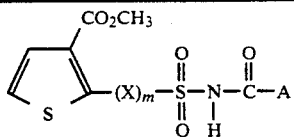

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |
| 74 | $CH_2$ | 1 | A2-4 | |
| 75 | $CH_2$ | 1 | A3-1 | |
| 76 | $CH_2$ | 1 | A3-2 | |
| 77 | $CH_2$ | 1 | A3-3 | |
| 78 | $CH_2$ | 1 | A3-4 | |
| 79 | $CH_2$ | 1 | A4-1 | |
| 80 | $CH_2$ | 1 | A4-2 | |
| 81 | $CH_2$ | 1 | A4-3 | |
| 82 | $CH_2$ | 1 | A4-4 | |
| 83 | $CH_2$ | 1 | A5-1 | |
| 84 | $CH_2$ | 1 | A5-2 | |
| 85 | $CH_2$ | 1 | A5-3 | |
| 86 | $CH_2$ | 1 | A5-4 | |
| 87 | $CH_2$ | 1 | A6-1 | |
| 88 | $CH_2$ | 1 | A6-2 | |
| 89 | $CH_2$ | 1 | A7-1 | |
| 90 | $CH_2$ | 1 | A7-2 | |
| 91 | $CH_2$ | 1 | A7-3 | |
| 92 | $CH_2$ | 1 | A7-4 | |
| 93 | $CH_2$ | 1 | A7-5 | |
| 94 | $CH_2$ | 1 | A8-2 | |
| 95 | $CH_2$ | 1 | A8-3 | |
| 96 | $CH_2$ | 1 | A8-4 | |
| 97 | $CH_2$ | 1 | A8-5 | |
| 98 | $CH_2$ | 1 | A8-6 | |
| 99 | $CH_2$ | 1 | A8-7 | |
| 100 | $CH_2$ | 1 | A8-9 | |
| 101 | $CH_2$ | 1 | A8-10 | |
| 102 | $CH_2$ | 1 | A8-11 | |
| 103 | $CH_2$ | 1 | A8-12 | |
| 104 | $CH_2$ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |

TABLE 16-continued

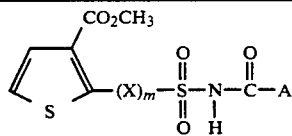

| Ex. No. | X | m | A | M.p. [°C.] |
|---|---|---|---|---|
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 17

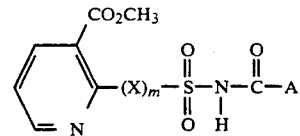

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |

TABLE 17-continued

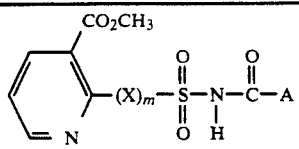

| Ex. No. | X | m | A | M.p. [°C.] |
|---|---|---|---|---|
| 74 | CH₂ | 1 | A2-4 | |
| 75 | CH₂ | 1 | A3-1 | |
| 76 | CH₂ | 1 | A3-2 | |
| 77 | CH₂ | 1 | A3-3 | |
| 78 | CH₂ | 1 | A3-4 | |
| 79 | CH₂ | 1 | A4-1 | |
| 80 | CH₂ | 1 | A4-2 | |
| 81 | CH₂ | 1 | A4-3 | |
| 82 | CH₂ | 1 | A4-4 | |
| 83 | CH₂ | 1 | A5-1 | |
| 84 | CH₂ | 1 | A5-2 | |
| 85 | CH₂ | 1 | A5-3 | |
| 86 | CH₂ | 1 | A5-4 | |
| 87 | CH₂ | 1 | A6-1 | |
| 88 | CH₂ | 1 | A6-2 | |
| 89 | CH₂ | 1 | A7-1 | |
| 90 | CH₂ | 1 | A7-2 | |
| 91 | CH₂ | 1 | A7-3 | |
| 92 | CH₂ | 1 | A7-4 | |
| 93 | CH₂ | 1 | A7-5 | |
| 94 | CH₂ | 1 | A8-2 | |
| 95 | CH₂ | 1 | A8-3 | |
| 96 | CH₂ | 1 | A8-4 | |
| 97 | CH₂ | 1 | A8-5 | |
| 98 | CH₂ | 1 | A8-6 | |
| 99 | CH₂ | 1 | A8-7 | |
| 100 | CH₂ | 1 | A8-9 | |
| 101 | CH₂ | 1 | A8-10 | |
| 102 | CH₂ | 1 | A8-11 | |
| 103 | CH₂ | 1 | A8-12 | |
| 104 | CH₂ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |

TABLE 17-continued

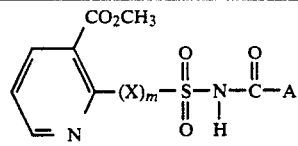

| Ex. No. | X | m | A | M.p. [°C.] |
|---|---|---|---|---|
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 18

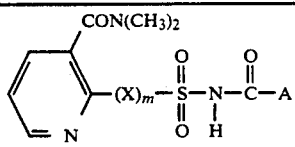

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |
| 74 | $CH_2$ | 1 | A2-4 | |
| 75 | $CH_2$ | 1 | A3-1 | |
| 76 | $CH_2$ | 1 | A3-2 | |
| 77 | $CH_2$ | 1 | A3-3 | |
| 78 | $CH_2$ | 1 | A3-4 | |
| 79 | $CH_2$ | 1 | A4-1 | |
| 80 | $CH_2$ | 1 | A4-2 | |
| 81 | $CH_2$ | 1 | A4-3 | |
| 82 | $CH_2$ | 1 | A4-4 | |
| 83 | $CH_2$ | 1 | A5-1 | |
| 84 | $CH_2$ | 1 | A5-2 | |
| 85 | $CH_2$ | 1 | A5-3 | |
| 86 | $CH_2$ | 1 | A5-4 | |
| 87 | $CH_2$ | 1 | A6-1 | |
| 88 | $CH_2$ | 1 | A6-2 | |
| 89 | $CH_2$ | 1 | A7-1 | |
| 90 | $CH_2$ | 1 | A7-2 | |
| 91 | $CH_2$ | 1 | A7-3 | |
| 92 | $CH_2$ | 1 | A7-4 | |
| 93 | $CH_2$ | 1 | A7-5 | |
| 94 | $CH_2$ | 1 | A8-2 | |
| 95 | $CH_2$ | 1 | A8-3 | |
| 96 | $CH_2$ | 1 | A8-4 | |
| 97 | $CH_2$ | 1 | A8-5 | |
| 98 | $CH_2$ | 1 | A8-6 | |
| 99 | $CH_2$ | 1 | A8-7 | |
| 100 | $CH_2$ | 1 | A8-9 | |
| 101 | $CH_2$ | 1 | A8-10 | |
| 102 | $CH_2$ | 1 | A8-11 | |
| 103 | $CH_2$ | 1 | A8-12 | |
| 104 | $CH_2$ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |

TABLE 18-continued

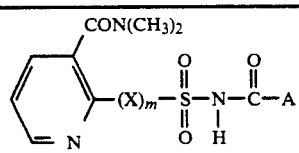

| Ex. No. | X | m | A | M.p. [°C.] |
|---|---|---|---|---|
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 19

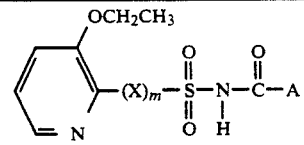

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |

TABLE 19-continued

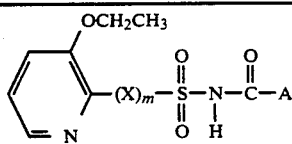

| Ex. No. | X | m | A | M.p. [°C.] |
|---|---|---|---|---|
| 74 | CH₂ | 1 | A2-4 | |
| 75 | CH₂ | 1 | A3-1 | |
| 76 | CH₂ | 1 | A3-2 | |
| 77 | CH₂ | 1 | A3-3 | |
| 78 | CH₂ | 1 | A3-4 | |
| 79 | CH₂ | 1 | A4-1 | |
| 80 | CH₂ | 1 | A4-2 | |
| 81 | CH₂ | 1 | A4-3 | |
| 82 | CH₂ | 1 | A4-4 | |
| 83 | CH₂ | 1 | A5-1 | |
| 84 | CH₂ | 1 | A5-2 | |
| 85 | CH₂ | 1 | A5-3 | |
| 86 | CH₂ | 1 | A5-4 | |
| 87 | CH₂ | 1 | A6-1 | |
| 88 | CH₂ | 1 | A6-2 | |
| 89 | CH₂ | 1 | A7-1 | |
| 90 | CH₂ | 1 | A7-2 | |
| 91 | CH₂ | 1 | A7-3 | |
| 92 | CH₂ | 1 | A7-4 | |
| 93 | CH₂ | 1 | A7-5 | |
| 94 | CH₂ | 1 | A8-2 | |
| 95 | CH₂ | 1 | A8-3 | |
| 96 | CH₂ | 1 | A8-4 | |
| 97 | CH₂ | 1 | A8-5 | |
| 98 | CH₂ | 1 | A8-6 | |
| 99 | CH₂ | 1 | A8-7 | |
| 100 | CH₂ | 1 | A8-9 | |
| 101 | CH₂ | 1 | A8-10 | |
| 102 | CH₂ | 1 | A8-11 | |
| 103 | CH₂ | 1 | A8-12 | |
| 104 | CH₂ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 20

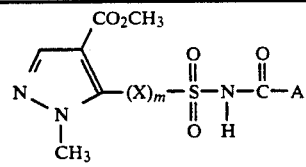

| Ex. No. | X | m | A | M.p. [°C.] |
|---|---|---|---|---|
| 0 | | | | |
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |
| 70 | $CH_2$ | 1 | A1-25 | |
| 71 | $CH_2$ | 1 | A2-1 | |
| 72 | $CH_2$ | 1 | A2-2 | |
| 73 | $CH_2$ | 1 | A2-3 | |
| 74 | $CH_2$ | 1 | A2-4 | |
| 75 | $CH_2$ | 1 | A3-1 | |
| 76 | $CH_2$ | 1 | A3-2 | |
| 77 | $CH_2$ | 1 | A3-3 | |
| 78 | $CH_2$ | 1 | A3-4 | |
| 79 | $CH_2$ | 1 | A4-1 | |
| 80 | $CH_2$ | 1 | A4-2 | |
| 81 | $CH_2$ | 1 | A4-3 | |
| 82 | $CH_2$ | 1 | A4-4 | |
| 83 | $CH_2$ | 1 | A5-1 | |
| 84 | $CH_2$ | 1 | A5-2 | |
| 85 | $CH_2$ | 1 | A5-3 | |
| 86 | $CH_2$ | 1 | A5-4 | |
| 87 | $CH_2$ | 1 | A6-1 | |
| 88 | $CH_2$ | 1 | A6-2 | |
| 89 | $CH_2$ | 1 | A7-1 | |
| 90 | $CH_2$ | 1 | A7-2 | |
| 91 | $CH_2$ | 1 | A7-3 | |
| 92 | $CH_2$ | 1 | A7-4 | |
| 93 | $CH_2$ | 1 | A7-5 | |
| 94 | $CH_2$ | 1 | A8-2 | |
| 95 | $CH_2$ | 1 | A8-3 | |
| 96 | $CH_2$ | 1 | A8-4 | |
| 97 | $CH_2$ | 1 | A8-5 | |
| 98 | $CH_2$ | 1 | A8-6 | |
| 99 | $CH_2$ | 1 | A8-7 | |
| 100 | $CH_2$ | 1 | A8-9 | |
| 101 | $CH_2$ | 1 | A8-10 | |
| 102 | $CH_2$ | 1 | A8-11 | |
| 103 | $CH_2$ | 1 | A8-12 | |
| 104 | $CH_2$ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |

TABLE 20-continued

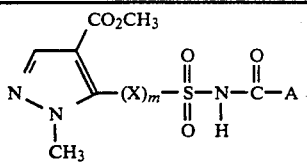

| Ex. No. | X | m | A | M.p. [°C.] |
|---|---|---|---|---|
| 144 | O | 1 | A7-4 | |
| 145 | O | 1 | A7-5 | |
| 146 | O | 1 | A8-2 | |
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 21

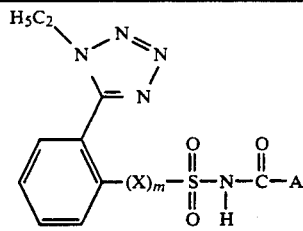

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | $CH_2$ | 1 | A1-5 | |
| 54 | $CH_2$ | 1 | A1-6 | |
| 55 | $CH_2$ | 1 | A1-7 | |
| 56 | $CH_2$ | 1 | A1-8 | |
| 57 | $CH_2$ | 1 | A1-9 | |
| 58 | $CH_2$ | 1 | A1-10 | |
| 59 | $CH_2$ | 1 | A1-11 | |
| 60 | $CH_2$ | 1 | A1-12 | |
| 61 | $CH_2$ | 1 | A1-13 | |
| 62 | $CH_2$ | 1 | A1-14 | |
| 63 | $CH_2$ | 1 | A1-15 | |
| 64 | $CH_2$ | 1 | A1-16 | |
| 65 | $CH_2$ | 1 | A1-17 | |
| 66 | $CH_2$ | 1 | A1-21 | |
| 67 | $CH_2$ | 1 | A1-22 | |
| 68 | $CH_2$ | 1 | A1-23 | |
| 69 | $CH_2$ | 1 | A1-24 | |

TABLE 21-continued

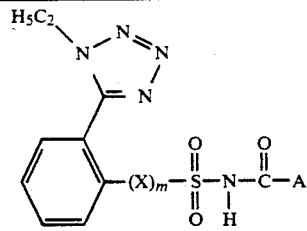

| Ex. No. | X | m | A | M.p. [°C.] |
|---|---|---|---|---|
| 70 | CH₂ | 1 | A1-25 | |
| 71 | CH₂ | 1 | A2-1 | |
| 72 | CH₂ | 1 | A2-2 | |
| 73 | CH₂ | 1 | A2-3 | |
| 74 | CH₂ | 1 | A2-4 | |
| 75 | CH₂ | 1 | A3-1 | |
| 76 | CH₂ | 1 | A3-2 | |
| 77 | CH₂ | 1 | A3-3 | |
| 78 | CH₂ | 1 | A3-4 | |
| 79 | CH₂ | 1 | A4-1 | |
| 80 | CH₂ | 1 | A4-2 | |
| 81 | CH₂ | 1 | A4-3 | |
| 82 | CH₂ | 1 | A4-4 | |
| 83 | CH₂ | 1 | A5-1 | |
| 84 | CH₂ | 1 | A5-2 | |
| 85 | CH₂ | 1 | A5-3 | |
| 86 | CH₂ | 1 | A5-4 | |
| 87 | CH₂ | 1 | A6-1 | |
| 88 | CH₂ | 1 | A6-2 | |
| 89 | CH₂ | 1 | A7-1 | |
| 90 | CH₂ | 1 | A7-2 | |
| 91 | CH₂ | 1 | A7-3 | |
| 92 | CH₂ | 1 | A7-4 | |
| 93 | CH₂ | 1 | A7-5 | |
| 94 | CH₂ | 1 | A8-2 | |
| 95 | CH₂ | 1 | A8-3 | |
| 96 | CH₂ | 1 | A8-4 | |
| 97 | CH₂ | 1 | A8-5 | |
| 98 | CH₂ | 1 | A8-6 | |
| 99 | CH₂ | 1 | A8-7 | |
| 100 | CH₂ | 1 | A8-9 | |
| 101 | CH₂ | 1 | A8-10 | |
| 102 | CH₂ | 1 | A8-11 | |
| 103 | CH₂ | 1 | A8-12 | |
| 104 | CH₂ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |

TABLE 21-continued

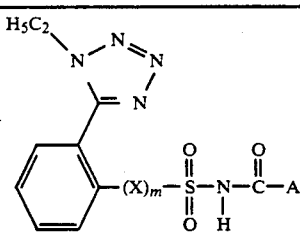

| Ex. No. | X | m | A | M.p. [°C.] |
|---|---|---|---|---|
| 208 | NH | 1 | A8-13 | |

TABLE 22

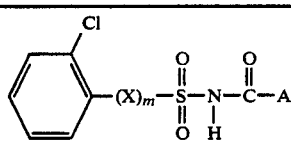

| Ex. No. | X | m | A | M.p. [°C.] |
|---|---|---|---|---|
| 1 | — | 0 | A1-5 | |
| 2 | — | 0 | A1-6 | |
| 3 | — | 0 | A1-7 | |
| 4 | — | 0 | A1-8 | |
| 5 | — | 0 | A1-9 | |
| 6 | — | 0 | A1-10 | |
| 7 | — | 0 | A1-11 | |
| 8 | — | 0 | A1-12 | |
| 9 | — | 0 | A1-13 | |
| 10 | — | 0 | A1-14 | |
| 11 | — | 0 | A1-15 | |
| 12 | — | 0 | A1-16 | |
| 13 | — | 0 | A1-17 | |
| 14 | — | 0 | A1-21 | |
| 15 | — | 0 | A1-22 | |
| 16 | — | 0 | A1-23 | |
| 17 | — | 0 | A1-24 | |
| 18 | — | 0 | A1-25 | |
| 19 | — | 0 | A2-1 | |
| 20 | — | 0 | A2-2 | |
| 21 | — | 0 | A2-3 | |
| 22 | — | 0 | A2-4 | |
| 23 | — | 0 | A3-1 | |
| 24 | — | 0 | A3-2 | |
| 25 | — | 0 | A3-3 | |
| 26 | — | 0 | A3-4 | |
| 27 | — | 0 | A4-1 | |
| 28 | — | 0 | A4-2 | |
| 29 | — | 0 | A4-3 | |
| 30 | — | 0 | A4-4 | |
| 31 | — | 0 | A5-1 | |
| 32 | — | 0 | A5-2 | |
| 33 | — | 0 | A5-3 | |
| 34 | — | 0 | A5-4 | |
| 35 | — | 0 | A6-1 | |
| 36 | — | 0 | A6-2 | |
| 37 | — | 0 | A7-1 | |
| 38 | — | 0 | A7-2 | |
| 39 | — | 0 | A7-3 | |
| 40 | — | 0 | A7-4 | |
| 41 | — | 0 | A7-5 | |
| 42 | — | 0 | A8-2 | |
| 43 | — | 0 | A8-3 | |
| 44 | — | 0 | A8-4 | |
| 45 | — | 0 | A8-5 | |
| 46 | — | 0 | A8-6 | |
| 47 | — | 0 | A8-7 | |
| 48 | — | 0 | A8-9 | |
| 49 | — | 0 | A8-10 | |
| 50 | — | 0 | A8-11 | |
| 51 | — | 0 | A8-12 | |
| 52 | — | 0 | A8-13 | |
| 53 | CH$_2$ | 1 | A1-5 | |
| 54 | CH$_2$ | 1 | A1-6 | |
| 55 | CH$_2$ | 1 | A1-7 | |

TABLE 22-continued

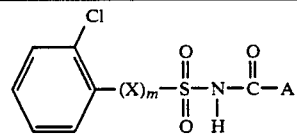

| Ex. No. | X | m | A | M.p. [°C.] |
|---|---|---|---|---|
| 56 | CH$_2$ | 1 | A1-8 | |
| 57 | CH$_2$ | 1 | A1-9 | |
| 58 | CH$_2$ | 1 | A1-10 | |
| 59 | CH$_2$ | 1 | A1-11 | |
| 60 | CH$_2$ | 1 | A1-12 | |
| 61 | CH$_2$ | 1 | A1-13 | |
| 62 | CH$_2$ | 1 | A1-14 | |
| 63 | CH$_2$ | 1 | A1-15 | |
| 64 | CH$_2$ | 1 | A1-16 | |
| 65 | CH$_2$ | 1 | A1-17 | |
| 66 | CH$_2$ | 1 | A1-21 | |
| 67 | CH$_2$ | 1 | A1-22 | |
| 68 | CH$_2$ | 1 | A1-23 | |
| 69 | CH$_2$ | 1 | A1-24 | |
| 70 | CH$_2$ | 1 | A1-25 | |
| 71 | CH$_2$ | 1 | A2-1 | |
| 72 | CH$_2$ | 1 | A2-2 | |
| 73 | CH$_2$ | 1 | A2-3 | |
| 74 | CH$_2$ | 1 | A2-4 | |
| 75 | CH$_2$ | 1 | A3-1 | |
| 76 | CH$_2$ | 1 | A3-2 | |
| 77 | CH$_2$ | 1 | A3-3 | |
| 78 | CH$_2$ | 1 | A3-4 | |
| 79 | CH$_2$ | 1 | A4-1 | |
| 80 | CH$_2$ | 1 | A4-2 | |
| 81 | CH$_2$ | 1 | A4-3 | |
| 82 | CH$_2$ | 1 | A4-4 | |
| 83 | CH$_2$ | 1 | A5-1 | |
| 84 | CH$_2$ | 1 | A5-2 | |
| 85 | CH$_2$ | 1 | A5-3 | |
| 86 | CH$_2$ | 1 | A5-4 | |
| 87 | CH$_2$ | 1 | A6-1 | |
| 88 | CH$_2$ | 1 | A6-2 | |
| 89 | CH$_2$ | 1 | A7-1 | |
| 90 | CH$_2$ | 1 | A7-2 | |
| 91 | CH$_2$ | 1 | A7-3 | |
| 92 | CH$_2$ | 1 | A7-4 | |
| 93 | CH$_2$ | 1 | A7-5 | |
| 94 | CH$_2$ | 1 | A8-2 | |
| 95 | CH$_2$ | 1 | A8-3 | |
| 96 | CH$_2$ | 1 | A8-4 | |
| 97 | CH$_2$ | 1 | A8-5 | |
| 98 | CH$_2$ | 1 | A8-6 | |
| 99 | CH$_2$ | 1 | A8-7 | |
| 100 | CH$_2$ | 1 | A8-9 | |
| 101 | CH$_2$ | 1 | A8-10 | |
| 102 | CH$_2$ | 1 | A8-11 | |
| 103 | CH$_2$ | 1 | A8-12 | |
| 104 | CH$_2$ | 1 | A8-13 | |
| 105 | O | 1 | A1-5 | |
| 106 | O | 1 | A1-6 | |
| 107 | O | 1 | A1-7 | |
| 108 | O | 1 | A1-8 | |
| 109 | O | 1 | A1-9 | |
| 110 | O | 1 | A1-10 | |
| 111 | O | 1 | A1-11 | |
| 112 | O | 1 | A1-12 | |
| 113 | O | 1 | A1-13 | |
| 114 | O | 1 | A1-14 | |
| 115 | O | 1 | A1-15 | |
| 116 | O | 1 | A1-16 | |
| 117 | O | 1 | A1-17 | |
| 118 | O | 1 | A1-21 | |
| 119 | O | 1 | A1-22 | |
| 120 | O | 1 | A1-23 | |
| 121 | O | 1 | A1-24 | |
| 122 | O | 1 | A1-25 | |
| 123 | O | 1 | A2-1 | |
| 124 | O | 1 | A2-2 | |
| 125 | O | 1 | A2-3 | |
| 126 | O | 1 | A2-4 | |
| 127 | O | 1 | A3-1 | |
| 128 | O | 1 | A3-2 | |

TABLE 22-continued

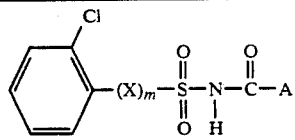

| Ex. No. | X | m | A | M.p. [°C.] |
|---|---|---|---|---|
| 129 | O | 1 | A3-3 | |
| 130 | O | 1 | A3-4 | |
| 131 | O | 1 | A4-1 | |
| 132 | O | 1 | A4-2 | |
| 133 | O | 1 | A4-3 | |
| 134 | O | 1 | A4-4 | |
| 135 | O | 1 | A5-1 | |
| 136 | O | 1 | A5-2 | |
| 137 | O | 1 | A5-3 | |
| 138 | O | 1 | A5-4 | |
| 139 | O | 1 | A6-1 | |
| 140 | O | 1 | A6-2 | |
| 141 | O | 1 | A7-1 | |
| 142 | O | 1 | A7-2 | |
| 143 | O | 1 | A7-3 | |
| 144 | O | 1 | A7-4 | |
| 145 | O | 1 | A7-5 | |
| 146 | O | 1 | A8-2 | |
| 147 | O | 1 | A8-3 | |
| 148 | O | 1 | A8-4 | |
| 149 | O | 1 | A8-5 | |
| 150 | O | 1 | A8-6 | |
| 151 | O | 1 | A8-7 | |
| 152 | O | 1 | A8-9 | |
| 153 | O | 1 | A8-10 | |
| 154 | O | 1 | A8-11 | |
| 155 | O | 1 | A8-12 | |
| 156 | O | 1 | A8-13 | |
| 157 | NH | 1 | A1-5 | |
| 158 | NH | 1 | A1-65 | |
| 159 | NH | 1 | A1-7 | |
| 160 | NH | 1 | A1-8 | |
| 161 | NH | 1 | A1-9 | |
| 162 | NH | 1 | A1-10 | |
| 163 | NH | 1 | A1-11 | |
| 164 | NH | 1 | A1-12 | |
| 165 | NH | 1 | A1-13 | |
| 166 | NH | 1 | A1-14 | |
| 167 | NH | 1 | A1-15 | |
| 168 | NH | 1 | A1-16 | |
| 169 | NH | 1 | A1-17 | |
| 170 | NH | 1 | A1-21 | |
| 171 | NH | 1 | A1-22 | |
| 172 | NH | 1 | A1-23 | |
| 173 | NH | 1 | A1-24 | |
| 174 | NH | 1 | A1-25 | |
| 175 | NH | 1 | A2-1 | |
| 176 | NH | 1 | A2-2 | |
| 177 | NH | 1 | A2-3 | |
| 178 | NH | 1 | A2-4 | |
| 179 | NH | 1 | A3-1 | |
| 180 | NH | 1 | A3-2 | |
| 181 | NH | 1 | A3-3 | |
| 182 | NH | 1 | A3-4 | |
| 183 | NH | 1 | A4-1 | |
| 184 | NH | 1 | A4-2 | |
| 185 | NH | 1 | A4-3 | |
| 186 | NH | 1 | A4-4 | |
| 187 | NH | 1 | A5-1 | |
| 188 | NH | 1 | A5-2 | |
| 189 | NH | 1 | A5-3 | |
| 190 | NH | 1 | A5-4 | |
| 191 | NH | 1 | A6-1 | |
| 192 | NH | 1 | A6-2 | |
| 193 | NH | 1 | A7-1 | |
| 194 | NH | 1 | A7-2 | |
| 195 | NH | 1 | A7-3 | |
| 196 | NH | 1 | A7-4 | |
| 197 | NH | 1 | A7-5 | |
| 198 | NH | 1 | A8-2 | |
| 199 | NH | 1 | A8-3 | |
| 200 | NH | 1 | A8-4 | |
| 201 | NH | 1 | A8-5 | |

TABLE 22-continued

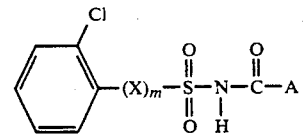

| Ex. No. | X | m | A | M.p. [°C.] |
|---|---|---|---|---|
| 202 | NH | 1 | A8-6 | |
| 203 | NH | 1 | A8-7 | |
| 204 | NH | 1 | A8-9 | |
| 205 | NH | 1 | A8-10 | |
| 206 | NH | 1 | A8-11 | |
| 207 | NH | 1 | A8-12 | |
| 208 | NH | 1 | A8-13 | |

TABLE 23

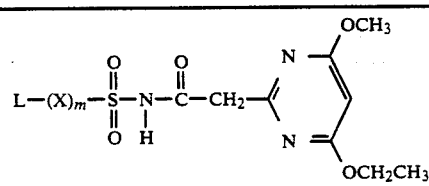

| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |

TABLE 24
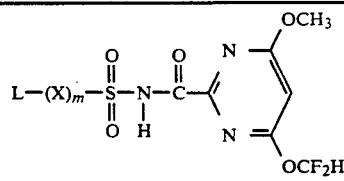
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 25
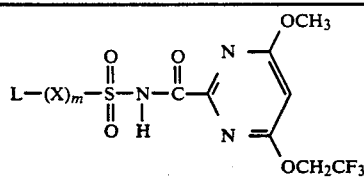
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 26
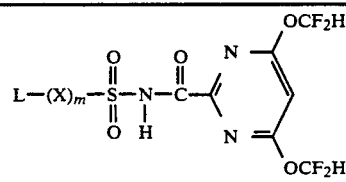
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |

TABLE 26-continued
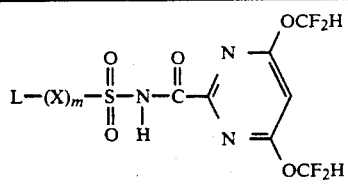
| Ex. No. | X | m | L | M.p. [°C.] |
|---|---|---|---|---|
| 37 | — | 0 | L5-6 | |
| 38 | — | 0 | L5-8 | |
| 39 | — | 0 | L5-9 | |
TABLE 27
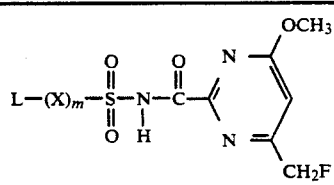
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 28
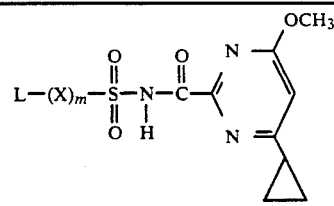
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 29
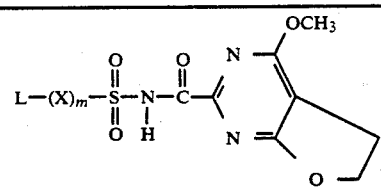
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |

TABLE 29-continued

L—(X)$_m$—S(O)(O)—N(H)—C(O)— [pyrimidine with OCH$_3$ group and fused ring with O]

| Ex. No. | X | m | L | M.p. [°C.] |
|---|---|---|---|---|
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |

TABLE 30

L—(X)$_m$—S(O)(O)—N(H)—C(O)— [pyrimidine with CH$_3$ group and fused ring with O]

| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |

TABLE 31

L—(X)$_m$—S(O)(O)—N(H)—C(O)— [pyrimidine with OCH$_3$ group and fused cyclopentane ring]

| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |

TABLE 32
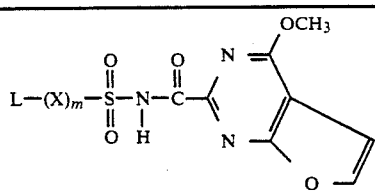
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 33
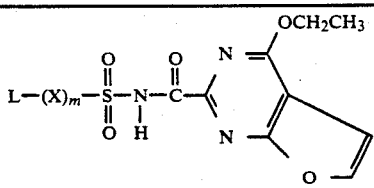
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
TABLE 33-continued
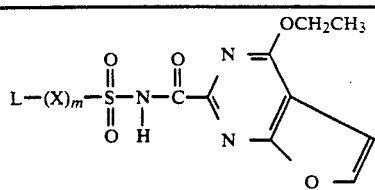
| Ex. No. | X | m | L | M.p. [°C.] |
|---|---|---|---|---|
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 34
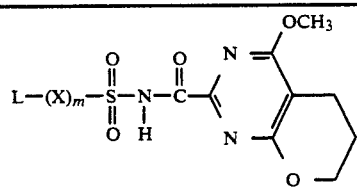
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |

TABLE 34-continued

L—(X)$_m$—SO$_2$—N(H)—C(=N—)—... (structure with OCH$_3$, N, O ring)

| Ex. No. | X | m | L | M.p. [°C.] |
|---|---|---|---|---|
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |

TABLE 35

L—(X)$_m$—SO$_2$—N(H)—C(=N—)—... (structure with CH$_3$, N, O ring)

| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |

TABLE 36

L—(X)$_m$—SO$_2$—N(H)—C(=O)—... (structure with N—N(CH$_3$), OCH$_3$)

| Ex. No. | X | m | L | M.p. [°C.] |
|---|---|---|---|---|
| 1 | — | 0 | L1-2 | |

TABLE 36-continued

| Ex. No. | X | m | L | M.p. [°C.] |
|---|---|---|---|---|
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |

TABLE 37

L—(X)$_m$—SO$_2$—N(H)—C(=O)—... (structure with N—N(CH$_3$), CH$_3$)

| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |

TABLE 37-continued
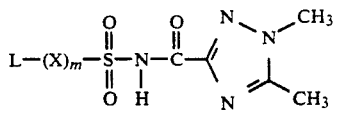
| Ex. No. | X | m | L | M.p. [°C.] |
|---|---|---|---|---|
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 38
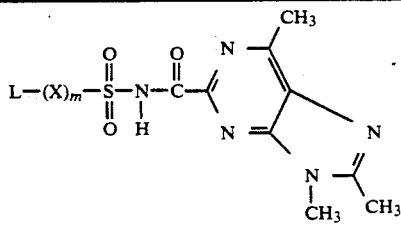
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 39
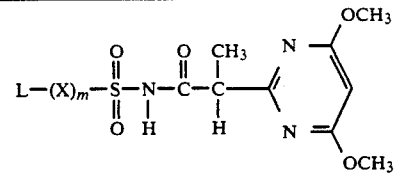
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 40
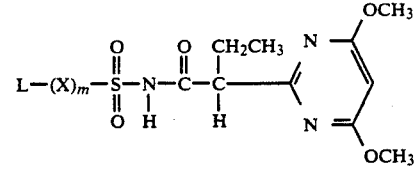
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |

TABLE 40-continued
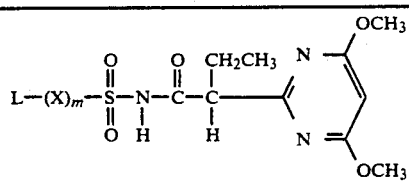
| Ex. No. | X | m | L | M.p. [°C.] |
|---|---|---|---|---|
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 41
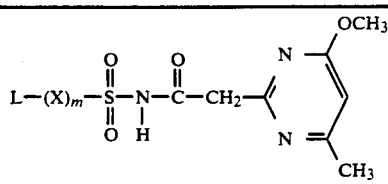
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
TABLE 41-continued
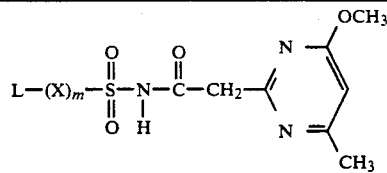
| Ex. No. | X | m | L | M.p. [°C.] |
|---|---|---|---|---|
| 37 | — | 0 | L5-6 | |
| 38 | — | 0 | L5-8 | |
| 39 | — | 0 | L5-9 | |
TABLE 42
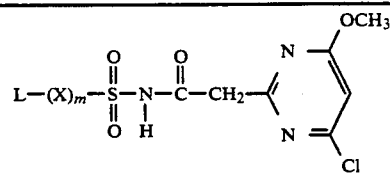
| Ex. No. | X | m | L | M.p. [°C.] |
|---|---|---|---|---|
| 1 | — | 0 | L1-2 | |
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |
TABLE 43
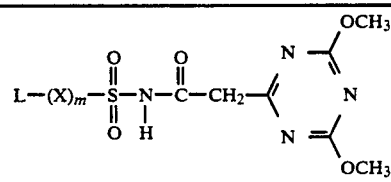
| Ex. No. | X | m | L | M.p. [°C.] |
|---|---|---|---|---|
| 1 | — | 0 | L1-2 | |

TABLE 43-continued $$L-(X)_m-\underset{\underset{O}{\|}}{\overset{\overset{O}{\|}}{S}}-\underset{H}{N}-\overset{\overset{O}{\|}}{C}-CH_2-\underset{N=\!\!\!\!=\!\!\!\!<_{OCH_3}}{\overset{N=\!\!\!\!=\!\!\!\!<^{OCH_3}}{\diagup}}$$

| Ex. No. | X | m | L | M.p. [°C.] |
|---|---|---|---|---|
| 2 | — | 0 | L1-4 | |
| 3 | — | 0 | L1-5 | |
| 4 | — | 0 | L1-6 | |
| 5 | — | 0 | L1-7 | |
| 6 | — | 0 | L1-8 | |
| 7 | — | 0 | L1-10 | |
| 8 | — | 0 | L1-11 | |
| 9 | — | 0 | L1-12 | |
| 10 | — | 0 | L1-14 | |
| 11 | — | 0 | L1-20 | |
| 12 | — | 0 | L1-22 | |
| 13 | — | 0 | L1-24 | |
| 14 | — | 0 | L1-25 | |
| 15 | — | 0 | L1-28 | |
| 16 | — | 0 | L1-34 | |
| 17 | — | 0 | L1-35 | |
| 18 | — | 0 | L1-37 | |
| 19 | — | 0 | L1-39 | |
| 20 | — | 0 | L1-40 | |
| 21 | — | 0 | L1-41 | |
| 22 | — | 0 | L1-45 | |
| 23 | — | 0 | L1-46 | |
| 24 | — | 0 | L1-48 | |
| 25 | — | 0 | L1-50 | |
| 26 | — | 0 | L1-51 | |
| 27 | — | 0 | L1-52 | |
| 28 | — | 0 | L1-53 | |
| 29 | — | 0 | L3-2 | |
| 30 | — | 0 | L3-3 | |
| 31 | — | 0 | L3-4 | |
| 32 | — | 0 | L4-2 | |
| 33 | — | 0 | L4-3 | |
| 34 | — | 0 | L5-2 | |
| 35 | — | 0 | L5-4 | |
| 36 | — | 0 | L5-5 | |
| 37 | — | 0 | L5-6 | |
| 38 | — | 0 | L5-8 | |
| 39 | — | 0 | L5-9 | |

BIOLOGICAL EXAMPLES

The damage on the weed plants and the tolerance by crop plants were scored using a key where numbers from 0 to 5 express the effectiveness. In the key 0 denotes no action
1 denotes 0–20% action or damage
2 denotes 20–40% action or damage
3 denotes 40–60% action or damage
4 denotes 60–80% action or damage
5 denotes 80–100% action or damage 1. Pre-emergence action on weeds Seeds or rhizome pieces of monocotyledon and dicotyledon weed plants were placed in plastic pots containing sandy loam and covered with soil. Various dosages of aqueous suspensions or emulsions of the compounds according to the invention formulated as wettable powders or emulsion concentrates were then applied to the surface of the cover soil, at an application rate of water of 600–800 l/ha (converted).

After the treatment, the pots were placed in the greenhouse and maintained at good growth conditions for the weeds. Visual scoring of the damage to plants or the emergence damage was carried out after the emergence of the test plants after a trial period of 3–4 weeks, comparing them to untreated control plants. As shown by the score data in Table 41, the compounds according to the invention have good herbicidal pre-emergence activity against a broad range of grass weeds and broadleaf weeds.

2. Post-emergence action weeds

Seeds or rhizome pieces of monocotyledon and dicotyledon weeds were placed in plastic pots in sandy loam ground, covered with soil and grown in the greenhouse under good growth conditions. Three weeks after sowing, the test plants were treated in the three-leaf stage.

Various dosages of the compounds according to the invention formulated as wettable powders or emulsion concentrates were sprayed onto the green parts of the plants, at an application rate of water of 600–800 l/ha (converted), and the results were scored visually after the rest plants had remained in the greenhouse for about 3–4 weeks under optimum growth conditions, comparing them to untreated control plants.

The agents according to the invention exhibit a good herbicidal activity against a broad range of economically important grass weeds and broad leaf-weeds, also in the post-emergence treatment (Table 42).

TABLE 41

Pre-emergence action of the compounds according to the invention

| Table | Ex. No. | Dosage (kg of a.i./ha) | SIA | CRS | STM | LOM | ECG | AS |
|---|---|---|---|---|---|---|---|---|
| 1 | 26 | 0.3 | 5 | 3 | 2 | 2 | 1 | 1 |
| 1 | 38 | 0.3 | 5 | 0 | 1 | 1 | 1 | 0 |
| 1 | 1 | 0.3 | 5 | 5 | 5 | 5 | 5 | 2 |
| 1 | 2 | 0.3 | 5 | 3 | 5 | 2 | 2 | 1 |
| 1 | 55 | 0.3 | 5 | 5 | 5 | 5 | 5 | 5 |
| 1 | 19 | 0.3 | 5 | 2 | 4 | 1 | 2 | 0 |
| 1 | 124 | 0.3 | 5 | 5 | 4 | 2 | 3 | 2 |
| 1 | 109 | 0.3 | 5 | 2 | 3 | 2 | 2 | 2 |
| 1 | 28 | 0.3 | 5 | 3 | 3 | 1 | 2 | 1 |
| 1 | 238 | 0.3 | 5 | 4 | 4 | 2 | 2 | 2 |
| 8 | 26 | 0.3 | 5 | 5 | 2 | 1 | 1 | 1 |
| 8 | 221 | 0.3 | 5 | 5 | 2 | 0 | 1 | 1 |
| 8 | 55 | 0.3 | 5 | 5 | 5 | 1 | 4 | 1 |
| 8 | 38 | 0.3 | 2 | 2 | 2 | 2 | 2 | 1 |
| 8 | 28 | 0.3 | 5 | 5 | 5 | 2 | 4 | 3 |
| 1 | 35 | 0.3 | 5 | 3 | 2 | 2 | 3 | 2 |
| 1 | 194 | 0.3 | 3 | 0 | 0 | 0 | 0 | 2 |
| 1 | 82 | 0.3 | 5 | 5 | 4 | 3 | 5 | 3 |
| 1 | 15 | 0.3 | 5 | 2 | 2 | 1 | 1 | 1 |
| 1 | 44 | 0.3 | 5 | 4 | 4 | 2 | 2 | 1 |
| 1 | 16 | 0.3 | 5 | 3 | 5 | 3 | 3 | 3 |
| 1 | 170 | 0.3 | 5 | 5 | 5 | 3 | 2 | 2 |
| 1 | 178 | 0.3 | 5 | 5 | 5 | 3 | 2 | 2 |
| 1 | 45 | 0.3 | 2 | 0 | 0 | 0 | 0 | 1 |
| 1 | 80 | 0.3 | 5 | 5 | 5 | 3 | 2 | 1 |
| 1 | 89 | 0.3 | 5 | 4 | 2 | 0 | 0 | 1 |
| 1 | 79 | 0.3 | 3 | 0 | 1 | 0 | 0 | 1 |
| 1 | 32 | 0.3 | 5 | 0 | 0 | 0 | 1 | 1 |
| 1 | 257 | 0.3 | 5 | 2 | 5 | 2 | 2 | 1 |
| 1 | 62 | 0.3 | 5 | 5 | 5 | 4 | 5 | 3 |
| 1 | 206 | 0.3 | 3 | 0 | 0 | 0 | 0 | 1 |
| 1 | 25 | 0.3 | 5 | 3 | 3 | 1 | 1 | 1 |
| 1 | 237 | 0.3 | 3 | 1 | 0 | 0 | 1 | 1 |
| 1 | 37 | 0.3 | 5 | 5 | 4 | 0 | 1 | 1 |
| 1 | 218 | 0.3 | 3 | 0 | 0 | 0 | 0 | 0 |
| 1 | 306 | 0.3 | 5 | 4 | 4 | 1 | 0 | 1 |
| 1 | 88 | 0.3 | 1 | 1 | 2 | 1 | 0 | 0 |
| 2 | 26 | 0.3 | 5 | 2 | 5 | 0 | 0 | 1 |
| 2 | 38 | 0.3 | 5 | 1 | 5 | 1 | 1 | 0 |
| 3 | 62 | 0.3 | 5 | 5 | 5 | 5 | 5 | 5 |
| 1 | 233 | 0.3 | 1 | 2 | 0 | 0 | 2 | 1 |
| 2 | 1 | 0.3 | 5 | 5 | 5 | 5 | 5 | 5 |
| 2 | 55 | 0.3 | 5 | 5 | 5 | 5 | 5 | 4 |
| 1 | 47 | 0.3 | 5 | 1 | 0 | 1 | 1 | 3 |
| 3 | 8 | 0.3 | 3 | 0 | 0 | 0 | 0 | 2 |
| 2 | 62 | 0.3 | 5 | 5 | 5 | 5 | 5 | 5 |
| 2 | 8 | 0.3 | 5 | 3 | 5 | 3 | 2 | 2 |
| 1 | 116 | 0.3 | 5 | 5 | 5 | 2 | 4 | 3 |
| 1 | 78 | 0.3 | 5 | 5 | 5 | 4 | 4 | 4 |

TABLE 41-continued

Pre-emergence action of the compounds according to the invention

| Table | Ex. No. | Dosage (kg of a.i./ha) | SIA | CRS | STM | LOM | ECG | AS |
|---|---|---|---|---|---|---|---|---|
| 1 | 70 | 0.3 | 5 | 5 | 5 | 4 | 5 | 3 |
| 1 | 297 | 0.3 | 5 | 5 | 5 | 4 | 4 | 4 |
| 1 | 69 | 0.3 | 5 | 5 | 5 | 4 | 5 | 4 |

TABLE 42

Post-emergence action of the compounds according to the invention

| Table | Ex. No. | Dosage (kg of a.i./ha) | SIA | CRS | STM | LOM | ECG | AS |
|---|---|---|---|---|---|---|---|---|
| 1 | 26 | 0.3 | 5 | 4 | 3 | 2 | 2 | 1 |
| 1 | 38 | 0.3 | 4 | 2 | 2 | 2 | 2 | 2 |
| 1 | 1 | 0.3 | 5 | 3 | 5 | 2 | 2 | 2 |
| 1 | 2 | 0.3 | 5 | 2 | 5 | 2 | 2 | 2 |
| 1 | 55 | 0.3 | 5 | 5 | 5 | 4 | 5 | 4 |
| 1 | 19 | 0.3 | 5 | 2 | 4 | 3 | 2 | 2 |
| 1 | 124 | 0.3 | 5 | 4 | 2 | 1 | 2 | 2 |
| 1 | 109 | 0.3 | 4 | 2 | 3 | 2 | 2 | 2 |
| 1 | 28 | 0.3 | 5 | 2 | 5 | 2 | 3 | 2 |
| 1 | 238 | 0.3 | 5 | 2 | 2 | 2 | 1 | 1 |
| 8 | 26 | 0.3 | 5 | 5 | 4 | 2 | 2 | 1 |
| 8 | 221 | 0.3 | 4 | 2 | 3 | 2 | 2 | 1 |
| 8 | 55 | 0.3 | 5 | 5 | 3 | 2 | 3 | 1 |
| 8 | 38 | 0.3 | 3 | 2 | 1 | 1 | 2 | 1 |
| 8 | 28 | 0.3 | 5 | 5 | 5 | 3 | 2 | 3 |
| 1 | 35 | 0.3 | 5 | 3 | 5 | 3 | 3 | 3 |
| 1 | 194 | 0.3 | 3 | 3 | 2 | 3 | 3 | 2 |
| 1 | 82 | 0.3 | 5 | 4 | 5 | 4 | 4 | 3 |
| 1 | 15 | 0.3 | 5 | 2 | 2 | 1 | 1 | 2 |
| 1 | 44 | 0.3 | 5 | 3 | 5 | 3 | 2 | 2 |
| 1 | 16 | 0.3 | 5 | 3 | 5 | 2 | 3 | 3 |
| 1 | 170 | 0.3 | 5 | 5 | 5 | 3 | 4 | 1 |
| 1 | 178 | 0.3 | 5 | 5 | 5 | 4 | 2 | 2 |
| 1 | 45 | 0.3 | 3 | 1 | 1 | 0 | 2 | 0 |
| 1 | 80 | 0.3 | 5 | 5 | 5 | 1 | 4 | 2 |
| 1 | 89 | 0.3 | 5 | 5 | 5 | 2 | 2 | 1 |
| 1 | 79 | 0.3 | 5 | 5 | 5 | 3 | 2 | 0 |
| 1 | 32 | 0.3 | 5 | 3 | 4 | 2 | 3 | 2 |
| 1 | 257 | 0.3 | 5 | 5 | 5 | 2 | 5 | 2 |
| 1 | 62 | 0.3 | 5 | 5 | 5 | 5 | 5 | 4 |
| 1 | 206 | 0.3 | 3 | 1 | 2 | 2 | 1 | 2 |
| 1 | 25 | 0.3 | 5 | 1 | 3 | 1 | 1 | 1 |
| 1 | 237 | 0.3 | 3 | 2 | 0 | 0 | 1 | 0 |
| 1 | 37 | 0.3 | 5 | 4 | 5 | 2 | 3 | 1 |
| 1 | 218 | 0.3 | 5 | 0 | 0 | 0 | 0 | 0 |
| 1 | 306 | 0.3 | 5 | 5 | 4 | 1 | 2 | 0 |
| 1 | 88 | 0.3 | 5 | 2 | 4 | 0 | 0 | 0 |
| 2 | 26 | 0.3 | 4 | 0 | 3 | 0 | 0 | 1 |
| 2 | 38 | 0.3 | 5 | 3 | 5 | 1 | 0 | 0 |
| 3 | 62 | 0.3 | 5 | 5 | 5 | 4 | 4 | 2 |
| 1 | 233 | 0.3 | 2 | 0 | 0 | 0 | 0 | 0 |
| 2 | 1 | 0.3 | 5 | 4 | 5 | 5 | 5 | 3 |
| 2 | 55 | 0.3 | 5 | 4 | 5 | 4 | 4 | 3 |
| 1 | 47 | 0.3 | 2 | 0 | 0 | 0 | 0 | 0 |
| 2 | 62 | 0.3 | 5 | 5 | 5 | 3 | 4 | 2 |
| 2 | 8 | 0.3 | 5 | 1 | 5 | 0 | 2 | 1 |
| 1 | 116 | 0.3 | 5 | 5 | 4 | 1 | 3 | 1 |
| 1 | 78 | 0.3 | 5 | 5 | 5 | 3 | 4 | 2 |
| 1 | 70 | 0.3 | 5 | 5 | 5 | 2 | 4 | 2 |
| 1 | 297 | 0.3 | 5 | 5 | 5 | 3 | 2 | 2 |
| 1 | 69 | 0.3 | 5 | 5 | 5 | 2 | 4 | 2 |

Abbreviations:
SIA = Sinapis alba
CRS = Chrysanthemum segetum
STM = Stellaria media
LOM = Lolium multiflorum
ECG = Echinochloa crus-galli
AS = Avena sativa
a.i. = active substance

We claim:
1. A compound of the formula I or a salt thereof

$$L-(X)_m-\underset{\underset{O}{\|}}{\overset{\overset{O}{\|}}{S}}-\underset{R^1}{N}-\overset{\overset{W}{\|}}{C}-\left(\underset{R^3}{\overset{R^2}{\underset{|}{C}}}\right)_n-A \qquad (I)$$

wherein $R^1$ is hydrogen, $(C_1-C_4)$-alkyl, $(C_2-C_6)$-alkenyl or $(C_2-C_6)$-alkynyl;

$R^2$ and $R^3$ independently of one another are hydrogen, $(C_1-C_3)$-alkyl or phenyl;

W is O, S, $NR^4$ or $NOR^4$;

$R^4$ is hydrogen, $(C_1-C_3)$-alkyl, $(C_1-C_3)$-haloalkyl or phenyl;

X is $CHR^2$, O, $NR^4$ or $NOR^4$;

L is a heterocyclic or isocyclic radical of the formulae (L1)-(L5)

(L1)     (L2)     (L3)

(L4)     (L5)

A is a heterocyclic radical of the formula (A1) or (A8)

(A1)     (A2)

Z is O or $S(O)_q$;

$E^1$ is O or $S(O)_b$;

$R^5$ is hydrogen, halogen, $NO_2$, CN, $(C_1-C_4)$-alkyl which is unsubstituted or monosubstituted or polysubstituted by F, Cl or Br or monosubstituted by CN, $OCH_3$ or $SCH_3$, or is $(C_2-C_4)$-alkenyl which is unsubstituted or monosubstituted or polysubstituted by F, Cl or Br or monosubstituted by $OCH_3$; or is $(C_2-C_4)$-alkynyl which is unsubstituted or monosubstituted or polysubstituted by F, Cl or Br or monosubstituted by $OCH_3$ or $Si(CH_3)_3$; or is $(C_3-C_6)$-cycloalkyl which is unsubstituted or monosubstituted or polysubstituted by F, Cl or $CH_3$; or is —$C(O)R^{10}$, —$OCH_2CH_2OR^{10}$, —OH, —$C(R^{10})$ $(OR^{11})$ $(OR^{12})$; —$CO_2R^{13}$, —C-

(O)NR$^{14}$R$^{15}$, —N$_3$, —SO$_2$NR$^{14}$R$^{15}$, —SO$_3$R$^{16}$, —OSO$_2$R$^{17}$, phenyl which is unsubstituted or monosubstituted or polysubstituted by F, Cl, Br, CH$_3$ or OCH$_3$; or is —E$^1$R$^{18}$ or —(CH$_2$)$_s$G;

R$^6$ is hydrogen or halogen; CN; NO$_2$; (C$_1$-C$_4$)-alkyl which is unsubstituted or monosubstituted or polysubstituted by halogen or monosubstituted to disubstituted by CO$_2$R$^{13}$, —SO$_2$NR$^{14}$R$^{15}$, —NR$^{14}$R$^{15}$, (C$_1$-C$_2$)-alkoxy, —E$^1$R$^{19}$, (C$_1$-C$_2$)-haloalkoxy, (C$_1$-C$_2$)-alkylthio, (C$_1$-C$_2$)-haloalkylthio, CN, OH, or SH; or is —CO$_2$R$^{13}$, —SO$_2$NR$^{14}$R$^{15}$, —NR$^{14}$R$^{15}$ or —E$^1$R$^{19}$;

R$^7$ radicals, independently of one another, are hydrogen, (C$_1$-C$_4$)-alkyl, (C$_1$-C$_4$)-haloalkyl, (C$_2$-C$_4$)-alkenyl, phenyl or phenyl which is monosubstituted or polysubstituted by halogen or —E$^1$R$^{19}$; or is —E$^1$R$^{19}$ or halogen;

R$^8$ is hydrogen, (C$_1$-C$_4$)-alkyl, (C$_1$-C$_4$)-haloalkyl, halogen, —CO$_2$R$^{13}$, —SO$_2$NR$^{14}$R$^{15}$, —OSO$_2$R$^{17}$, —S(O)$_2$R$^{18}$, CN or NO$_2$;

R$^9$ is hydrogen, (C$_1$-C$_4$)-alkyl which is unsubstituted or monosubstituted or polysubstituted by halogen or monosubstituted by phenyl; or is (C$_2$-C$_4$)-alkenyl; or is phenyl or phenyl which is monosubstituted or polysubstituted by halogen, (C$_1$-C$_4$)-alkyl, NO$_2$, CN or (C$_1$-C$_4$)-alkoxy;

R$^{10}$ is hydrogen, (C$_1$-C$_4$)-alkyl, (C$_1$-C$_4$)-alkyl which is monosubstituted or polysubstituted by F, Cl, Br or OCH$_3$; or is (C$_3$-C$_6$)-cycloalkyl which is unsubstituted or monosubstituted or polysubstituted by F, Cl, Br or CH$_3$; or is (C$_2$-C$_4$)-alkenyl or (C$_2$-C$_4$)-alkynyl;

R$^{11}$ and R$^{12}$ independently of one another are (C$_1$-C$_4$)-alkyl, or R$^{11}$ and R$^{12}$ together are —CH$_2$CH$_2$—, —CH$_2$OCH$_2$— or —CH$_2$C(CH$_3$)$_2$CH$_2$—;

R$^{13}$ is hydrogen, (C$_1$-C$_4$)-alkyl which is unsubstituted or monosubstituted or polysubstituted by halogen or monosubstituted to disubstituted by CN, CO$_2$R$^{10}$, NR$^{14}$R$^{15}$, OR$^{10}$ or Si(CH$_3$)$_3$; or is (C$_2$-C$_4$)-alkynyl which is unsubstituted or substituted by CH$_3$ or Si(CH$_3$)$_3$; or is (C$_3$-C$_6$)-cycloalkyl, (C$_3$-C$_6$)-cycloalkyl-(C$_1$-C$_4$)alkyl, (C$_1$-C$_4$)-alkoxy or Si(CH$_3$)$_3$;

R$^{14}$ is hydrogen or (C$_1$-C$_4$)-alkyl, or R$^{14}$ and R$^{15}$ together are —(CH$_2$)$_2$(CH$_2$)$_a$(CH$_2$)$_2$— or —(CH$_2$)$_2$O(CH$_2$)$_2$—;

R$^{15}$ is hydrogen, (C$_1$-C$_4$)-alkyl, (C$_1$-C$_4$)-alkoxy, (C$_2$-C$_4$)-alkenyl, or R$^{14}$ and R$^{15}$ together are —(CH$_2$)$_2$(CH$_2$)$_a$(CH$_2$)$_2$— or —(CH$_2$)$_2$O(CH$_2$)$_2$—;

R$^{16}$ is (C$_1$-C$_4$)-alkyl or (C$_1$-C$_4$)-haloalkyl;

R$^{17}$ is (C$_1$-C$_4$)-alkyl or NR$^{14}$R$^{15}$;

R$^{18}$ is (C$_1$-C$_4$)-alkyl, (C$_1$-C$_4$)-haloalkyl, (C$_2$-C$_4$)-alkoxyalkyl, (C$_2$-C$_4$)-alkenyl, (C$_3$-C$_4$)-alkynyl, phenyl or phenyl which is monosubstituted or polysubstituted by halogen, (C$_1$-C$_3$)-alkyl, (C$_1$-C$_3$)-alkoxy or (C$_1$-C$_3$)-haloalkyl;

R$^{19}$ is (C$_1$-C$_4$)-alkyl or (C$_1$-C$_4$)-alkyl which is monosubstituted or polysubstituted by F or Cl or monosubstituted by OR$^{16}$;

R$^{20}$ and R$^{21}$ independently of one another are hydrogen, halogen, (C$_1$-C$_6$)-alkyl, (C$_1$-C$_6$)-alkoxy or (C$_1$-C$_6$)-alkylthio, it being possible for the three abovementioned radicals to be monosubstituted or polysubstituted by halogen or monosubstituted or disubstituted by (C$_1$-C$_4$)-alkoxy or (C$_1$-C$_4$)-alkylthio; or are NR$^{14}$R$^{15}$, (C$_3$-C$_6$)-cycloalkyl, —OCHR$^{14}$—CO$_2$R$^{13}$, (C$_2$-C$_5$)-alkenyl, (C$_2$-C$_4$)-alkynyl, (C$_3$-C$_5$)-alkenyloxy or (C$_3$-C$_5$)-alkynyloxy;

R$^{26}$ is hydrogen or (C$_1$-C$_3$)-alkyl;

G is a heterocyclic radical ( G 1)–(G 25),

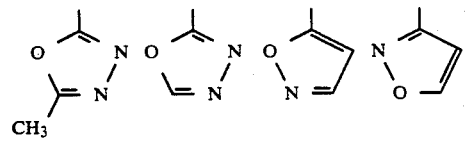

(G1)    (G2)    (G3)    (G4)

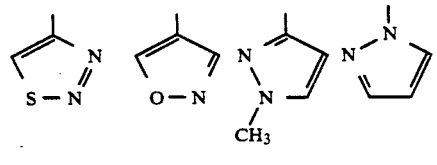

(G5)    (G6)    (G7)    (G8)

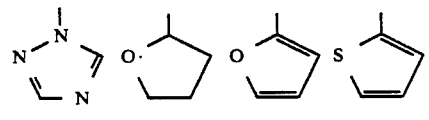

(G9)    (G10)    (G11)    (G12)

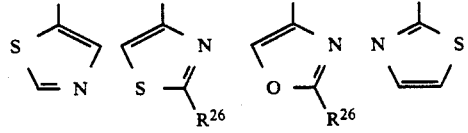

(G13)    (G14)    (G15)    (G16)

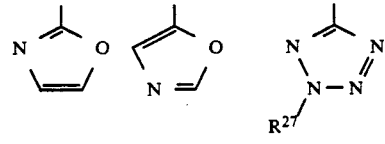

(G17)    (G18)    (G19)

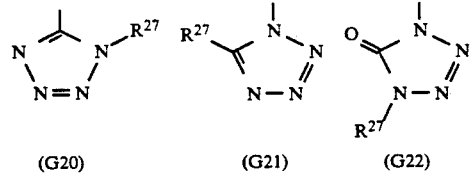

(G20)    (G21)    (G22)

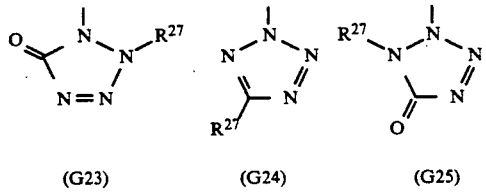

(G23)    (G24)    (G25)

R$^{27}$ is hydrogen, (C$_1$-C$_3$)-alkyl or (C$_2$-C$_4$)-alkenyl;

a, m, n, p, r and s, independently of one another are 0 or 1;

and b and q, independently of one another, are 0, 1 or 2.

2. A compound as claimed in claim 1, wherein in formula I,

L is a radical of the formula (L1), (L3), (L4) or (L5);
X is $CH_2$, $CH(CH_3)$, O, NH, $NCH_3$, $NC_2H_5$ OR $NOCH_3$;
W is oxygen;
$R^1$ is hydrogen;
$R^2$ and $R^3$ independently of one another are hydrogen or $(C_1-C_3)$-alkyl;
$R^5$ is halogen, $NO_2$, CN, $(C_1-C_3)$-alkyl which is unsubstituted or substituted by F, Cl, Br, CN, $OCH_3$ or $SCH_3$; or is $(C_3)$-alkenyl which is unsubstituted or substituted by F, Cl or Br; or is $(C_3)$-alkynyl, $(C_3)$-cycloalkyl, which is unsubstituted or substituted by F, Cl or $CH_3$, or is $-C(O)R^{10}$, $-OCH_2CH_2OR^{10}$, OH, $-C(R^{10})(OR^{11})(OR^{12})$, $-CO_2R^{13}$, $-C(O)NR^{14}R^{15}$, $N_3$, $-SO_2NR^{14}R^{15}$, $-OSO_2R^{17}$, $-E^1R^{18}$ or $-(CH_2)_sG$;
$R^6$ is hydrogen, halogen, CH, $NO_2$, $CH_3$, $CF_3$, $-E^1R^{19}$ or $(C_1-C_2)$-alkoxy-$(C_1-C_2)$-alkyl, $(C_1-C_2)$-haloalkoxy, $(C_1-C_2)$-alkylthio, $(C_1-C_2)$-haloalkylthio, CN, $-CO_2R^{13}$ or $-SO_2NR^{14}R^{15}$;
$R^7$ is hydrogen;
$R^{10}$ is $(C_1-C_3)$-alkyl, cyclopropyl or $(C_3)$-alkenyl;
$R^{11}$ and $R^{12}$ are $(C_1-C_2)$-alkyl, or $R^{11}$ and $R^{12}$ together are $-CH_2CH_2-$;
$R^{13}$ is $(C_1-C_3)$-alkyl, $(C_3)$-alkenyl, $-CH_2CH_2F$, $-CH_2CH_2Cl$, $-CH_2CH_2OCH_3$ or cyclopropylmethyl;
$R^{14}$ is hydrogen or $CH_3$, or $R^{14}$ and $R^{15}$ together are $-(CH_2)_4-$, $-(CH_2)_5-$ or $-(CH_2)_2O(CH_2)_2-$;
$R^{15}$ is $CH_3$, $CH_2CH_3$ or $OCH_3$, or $R^{14}$ and $R^{15}$ together are $-(CH_2)_4-$, $-(CH_2)_5-$ or $-(CH_2)_2O(CH_2)_2-$;
$R^{18}$ is $(C_1-C_3)$-alkyl, $(C_1-C_3)$-haloalkyl, $(C_2-C_3)$-alkoxyalkyl, allyl, propargyl or $(C_2-C_3)$-haloalkenyl;
$R^{19}$ is $(C_1-C_2)$-alkyl which is unsubstituted or substituted by F, Cl or $OCH_3$;
$R^{20}$ and $R^{21}$ independently of one another are hydrogen, $(C_1-C_2)$-alkyl, $(C_1-C_2)$-alkoxy, $-CH_2OCH_3$, Cl, F, Br, I, $-CH_2OCH_2CH_3$ $-NHCH_3$, $-N(OCH_3)CH_3$, $-N(CH_3)_2$, $-CF_3$, $-SCH_3$, $-CH(OCH_3)_2$, $-OCH_2CH=CH_2$; $-OCH_2C\equiv CH$; $-OCH_2CH_2CH_2-OCH_3$, $-CH_2SCH_3$, $-OCHF_2$, $-SCHF_2$, cyclopropyl, $-C\equiv CH$ or $-C\equiv C-CH_3$;
m is 0 or 1;
n is 0 or 1;
s is zero; and
$E^1$ is O or S.

3. A compound as claimed in claim 1, wherein A is a radical or the formula (A1).

4. A compound as claimed in claim 2, wherein A is a radical of the formula (A1).

5. A compound as claimed in claim 1, wherein L is a group of the formula (L1).

6. A compound as claimed in claim 2, wherein L is a group of the formula (L1).

7. A compound as claimed in claim 1, wherein L is a group of the formula (L3).

8. A compound as claimed in claim 1, wherein L is a group of the formula (L4).

9. A compound as claimed in claim 1, wherein L is a group of the formula (L5).

10. A herbicidal or plant growth-regulating composition, containing an effective amount of a compound of the formula I of claim 1 or a slat thereof and inert additives.

11. A herbicidal or plant growth-regulating composition, containing an effective amount of a compound of the formula I of claim 2 or a salt thereof and inert 12. A method of controlling undesired plants or for regulating the growth of plants, which comprises applying an effective amount of a compound of the formula I or a salt thereof, of claim 1, to these plants or the cropping area.

13. A method of controlling undesired plants or regulating the growth of plants, which comprises applying an effective amount of a compound of the formula I or a salt thereof, of claim 2, to these plants or the cropping areas.

* * * * *